US012583822B2

(12) United States Patent
Xiao et al.

(10) Patent No.: US 12,583,822 B2
(45) Date of Patent: Mar. 24, 2026

(54) BENZYLAMINE DERIVATIVE, PREPARATION METHOD THEREFOR AND USE THEREOF

(71) Applicant: ACADEMY OF MILITARY MEDICAL SCIENCES, Beijing (CN)

(72) Inventors: Junhai Xiao, Beijing (CN); Song Li, Beijing (CN); Jialin Guo, Beijing (CN); Wu Zhong, Beijing (CN); Longlong Luo, Beijing (CN); Zhibing Zheng, Beijing (CN); Xinbo Zhou, Beijing (CN); Xingzhou Li, Beijing (CN); Ruiyuan Cao, Beijing (CN); Shiyong Fan, Beijing (CN); Dian Xiao, Beijing (CN); Fei Xie, Beijing (CN); Wei Li, Beijing (CN)

(73) Assignee: Academy of Military Medical Sciences, Beijing (CN)

( * ) Notice: Subject to any disclaimer, the term of this patent is extended or adjusted under 35 U.S.C. 154(b) by 400 days.

(21) Appl. No.: 18/020,923

(22) PCT Filed: Jul. 28, 2021

(86) PCT No.: PCT/CN2021/108826
§ 371 (c)(1),
(2) Date: Feb. 10, 2023

(87) PCT Pub. No.: WO2022/033303
PCT Pub. Date: Feb. 17, 2022

(65) Prior Publication Data

US 2023/0303494 A1 Sep. 28, 2023

(30) Foreign Application Priority Data

Aug. 11, 2020 (CN) ......................... 202010801978.3

(51) Int. Cl.

| | |
|---|---|
| ***C07D 213/85*** | (2006.01) |
| ***A61P 35/00*** | (2006.01) |
| ***C07C 229/22*** | (2006.01) |
| ***C07C 255/54*** | (2006.01) |
| ***C07D 213/30*** | (2006.01) |
| ***C07D 213/74*** | (2006.01) |
| ***C07D 319/18*** | (2006.01) |
| ***C07D 401/12*** | (2006.01) |
| ***C07D 405/12*** | (2006.01) |

(52) U.S. Cl.
CPC ............ *C07D 213/85* (2013.01); *A61P 35/00* (2018.01); *C07C 229/22* (2013.01); *C07C 255/54* (2013.01); *C07D 213/30* (2013.01); *C07D 213/74* (2013.01); *C07D 319/18* (2013.01); *C07D 401/12* (2013.01); *C07D 405/12* (2013.01)

(58) Field of Classification Search
CPC .................................................... C07D 213/85
See application file for complete search history.

(56) References Cited

U.S. PATENT DOCUMENTS

| | | | |
|---|---|---|---|
| 8,039,513 | B2 | 10/2011 | Kang et al. |
| 2017/0174671 | A1 | 6/2017 | Wu et al. |
| 2018/0273519 | A1 | 9/2018 | Wu et al. |
| 2019/0016681 | A1 | 1/2019 | Dömling |
| 2021/0032270 | A1 | 2/2021 | Yang et al. |

FOREIGN PATENT DOCUMENTS

| | | | |
|---|---|---|---|
| CN | 107417564 | A | 12/2017 |
| CN | 107417572 | A | 12/2017 |
| CN | 108698995 | A | 10/2018 |

(Continued)

OTHER PUBLICATIONS

Cheng et al., "Discovery of Novel Resorcinol Dibenzyl Ethers Targeting the Programmed Cell Death-1/Programmed Cell-Death Ligand 1 Interaction as Potential Anticancer Agents," Journal of Medicinal Chemistry, Jul. 15, 2020. (92 pages).

(Continued)

*Primary Examiner* — Golam M Shameem

(74) *Attorney, Agent, or Firm* — Seed IP Law Group LLP

(57) ABSTRACT

The present invention relates to a benzylamine derivative, a preparation method therefor and use thereof, and in particular, to a benzylamine derivative as represented by general formula (I), or a pharmaceutically acceptable stereoisomer, salt, solvate or prodrug thereof, which has a strong binding capability with human PD-L1, can obviously inhibit the interaction of PD-1/PD-L1, and has significant anti-tumor efficacy in vivo. Therefore, the present invention also relates to a preparation method for the benzylamine derivative and use thereof in preparing a drug for treating PD-1/PD-L1-related diseases.

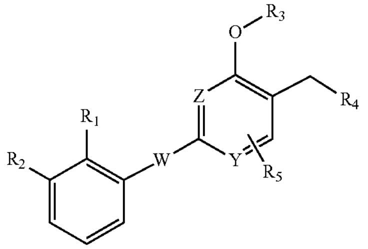

W = 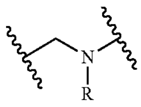 or

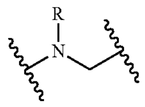

12 Claims, 1 Drawing Sheet

(56) References Cited

FOREIGN PATENT DOCUMENTS

| | | | |
|---|---|---|---|
| CN | 109721527 | A | 5/2019 |
| CN | 110092745 | A | 8/2019 |
| WO | 2015/034820 | A1 | 3/2015 |
| WO | 2015/160641 | A2 | 10/2015 |
| WO | 2017/066227 | A1 | 4/2017 |
| WO | 2017/202273 | A1 | 11/2017 |
| WO | 2017/202274 | A1 | 11/2017 |
| WO | 2017/202275 | A1 | 11/2017 |
| WO | 2017/202276 | A1 | 11/2017 |
| WO | 2017/202277 | A1 | 11/2017 |
| WO | 2018/044963 | A1 | 3/2018 |
| WO | 2018/118848 | A1 | 6/2018 |
| WO | 2018/119221 | A1 | 6/2018 |
| WO | 2018/183171 | A1 | 10/2018 |
| WO | 2018/195321 | A1 | 10/2018 |
| WO | 2019/149183 | A1 | 8/2019 |
| WO | 2019/191624 | A1 | 10/2019 |
| WO | 2020/011209 | A1 | 1/2020 |

OTHER PUBLICATIONS

Guo et al., "Designs, Synthesis, and Biological Evaluation of Linear Aliphatic Amine-Linked Triaryl Derivatives as Potent Small-Molecule Inhibitors of the Programmed Cell Death-1/Programmed Cell Death-Ligand 1 interaction with Promising Antitumor Effects in Vivo," Journal of Medicinal Chemistry 63:13825-13850, 2020. https://dx.doi.org/10.1021/acs.jmedchem.0c01329.

Guzik et al., "Small-molecule inhibitors of the Programmed Cell Death-1/Programmed Death ligand 1 (PD-1/PD-L1) interaction via transiently-induced protein states and dimerization of PD- L1," Journal of Medicinal Chemistry, Jun. 14, 2017. (39 pages).

Nagano et al., "7.1 The Foundation of Lead Compound Creation and Optimization," Pharmaceutical Chemistry, First Edition, pp. 133-136, Feb. 27, 2004 [with English Translation]. (12 pages).

Nozaki et al., "5.2.2 Biological Equivalence (Bioisoterism Principle)," Drug Discovery Chemistry, First Edition, pp. 98-99, Jul. 1, 1995 [with English Translation]. (6 pages).

Patani et al., "Bioisosterism: A Rational Approach in Drug Design," Chem. Rev. 96(8):3147-3176, Dec. 19, 1996. (30 pages).

BENZYLAMINE DERIVATIVE, PREPARATION METHOD THEREFOR AND USE THEREOF

The present application is based on the application with the CN application number of 202010801978.3 and the filing date of Aug. 11, 2020, and claims its priority. The disclosure of the CN application is hereby incorporated into the present application in its entirety.

TECHNICAL FIELD

The present invention belongs to the technical field of biomedicine, relates to a benzylamine derivative capable of blocking the interaction of PD-1/PD-L1, and also relates to a preparation method for the compound and use thereof in the manufacture of a medicament for the treatment of a disease associated with PD-1/PD-LL.

BACKGROUND ART

In recent years, significant progress has been made in tumor immunotherapy; and unlike traditional therapies such as chemoradiotherapy and targeted therapy, it mainly kills tumors by overcoming the immunosuppression in the patient and reactivating the patient's own immune cells.

At present, immune checkpoint PD-1/PD-L1 inhibitors are one of the most prominent achievements in tumor immunotherapy. PD-1 (programmed cell death protein 1) is expressed in T cells, B cells, NK cells and monocytes. The ligand PD-L1 (programmed cell death protein-ligand 1) of PD-1 is abundantly expressed on the surface of tumor cells, which can bind to PD-1 on the surface of T cells. The binding of PD-1 and PD-L1 generates a negative regulatory signal, which inhibits the immune activity of T cells, resulting in the escape of tumor cells from the recognition and attack of immune system, allowing immune escape and surviving. A large number of preclinical studies and the listing of monoclonal antibodies have fully proved that blocking the interaction of PD-1/PD-L1 can effectively restore the immune function of T cells, thereby realizing the recognition and elimination of tumor cells by the immune system, and inhibiting the tumor growth.

During 2014 to 2017, there were five monoclonal antibody PD-1/PD-L1 inhibitors on the market worldwide: Pembrolizumab (Keytruda®), Nivolumab (Opdivo®), Atezolizumab (Tecentriq™), Avelumab (Bavencio®) and Durvalumab (Imfinzi®). In December 2018, the PD-1 inhibitor (Toripalimab) of domestic Junshi Biosciences and the PD-1 inhibitor (Sintilimab) of Innovent Biologics were successively approved by the CFDA for marketing. In December 2019, the PD-1 inhibitor Tislelizumab of BeiGene was approved for marketing. According to the FDA clinical trial website (www.clinicaltrials.gov), as of September 2018, there were 2,250 clinical trials for monoclonal antibody PD-1/PD-L1 inhibitors worldwide to study their efficacy in combination with other anti-tumor drugs or expand their indications.

However, the high price of antibody drugs caused by high production cost, easy to cause immune-related side effects, poor stability, requiring low temperature storage and transportation, inconvenient in administration (oral administration is ineffective, and intravenous injection is required), inappropriate PK (low distribution volume, and long elimination half-life) and low effective rate (only 20% to 40% effective rate in most solid tumors), etc. seriously limit the clinical application of PD-1/PD-L1 inhibitors.

Small-molecule drugs have the advantages like low price, effective oral administration, good stability, low immune side effects, and easy penetration into tumors to improve the efficiency and so on. Compared with monoclonal antibodies, small molecule drugs have wider clinical application values.

At present, the research work on PD-1/PD-L1 small molecule inhibitors has just started, and most of the reported compounds are in the preclinical research stage, and there are no drugs on the market. Whether the existing compounds can successfully solve the shortcomings of the clinical application of monoclonal antibodies is still unknown. Therefore, efficient and novel small molecule inhibitors of PD-1/PD-L1 still require continuous research and development.

Contents of the Present Invention

One object of the present application is to provide a benzylamine derivative or pharmaceutically acceptable stereoisomer, salt, solvate or prodrug thereof that blocks the interaction of PD-1/PD=L1, and a pharmaceutical composition comprising any of the aforementioned components, a preparation method for the benzylamine derivative, and use thereof in the manufacture of a medicament for the prevention and treatment of a disease associated with PD-1/PD-L1.

In one aspect, the present application provides a benzylamine derivative of general Formula (I), or a pharmaceutically acceptable stereoisomer, salt, solvate or prodrug thereof, Formula (I)

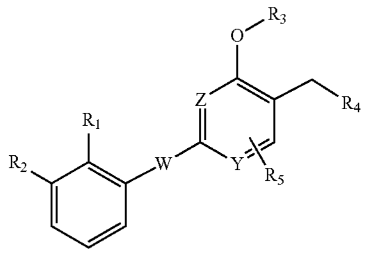

W = 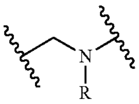 or 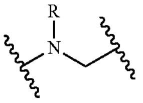

wherein,

R is selected from the group consisting of hydrogen and C1-C8 alkyl;

$R_1$ is selected from the group consisting of hydrogen, deuterium, halogen, C1-C4 alkyl, deuterated C1-C4 alkyl, halogenated C1-C4 alkyl and C1-C4 alkoxy;

$R_2$ is selected from the group consisting of

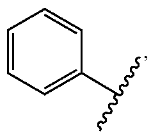, 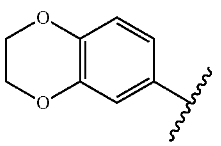 and

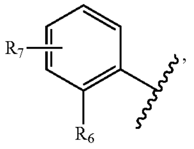, wherein $R_6$ is selected from the group consisting of halogen, C1-C4 alkyl, deuterated C1-C4 alkyl, halogenated C1-C4 alkyl and C1-C4 alkoxy, $R_7$ is at the meta or ortho position of $R_6$ and $R_7$ is selected from the group consisting of hydrogen, $—O—(CH_2)_n—R_0$, $—CONH—R_0$ and $—(CH_2)_n—R_0$, wherein n is an integer of 1-4, $R_0$ is cyano, hydroxyl, carboxyl, amino or a heteroatom-containing linear or cyclic hydrophilic substituent;

$R_3$ is selected from $R_8—CH_2—$, wherein $R_8$ is selected from the group consisting of hydrogen, cyano, C1-C4 alkyl, halogenated C1-C4 alkyl, C2-C4 alkenyl, $—NR_9R_{10}$, $—CONR_9R_{10}$, 3- to 6-membered cycloalkyl, 3- to 6-membered heterocycloalkyl, 6- to 10-membered aryl and 5- to 10-membered heteroaryl, optionally, the C1-C4 alkyl, halogenated C1-C4 alkyl, C2-C4 alkenyl, $—NR_9R_{10}$, $—CONR_9R_{10}$, 3- to 6-membered cycloalkyl, 3- to 6-membered heterocycloalkyl, 6- to 10-membered aryl, and 5- to 10-membered heteroaryl that are each independently substituted with one or more substituents selected from the group consisting of cyano, halogen, carboxyl, C1-C4 alkyl, C1-C4 alkoxy, C1-C4 alkylsulfonyl, 3- to 6-membered cycloalkyl, hydroxyl-substituted 3 to 6-membered cycloalkyl, 3- to 6-membered heterocycloalkyl, hydroxyl-substituted 3- to 6-membered heterocycloalkyl, $—CONR_9R_{10}$ and $—NR_9COR_{10}$, wherein $R_9$ and $R_{10}$ at each occurrence are each independently selected from the group consisting of hydrogen, deuterium and C1-C4 alkyl;

$R_4$ is selected from the group consisting of hydroxyl, carboxyl, fragment of amino acid (preferably hydrophilic amino acid) and $—NR_{10}R_{11}$, wherein $R_{10}$ and Ru are each independently selected from the group consisting of hydrogen, deuterium, C1-C6 alkyl and 3- to 6-membered cycloalkyl, optionally, the C1-C6 alkyl and 3- to 6-membered cycloalkyl are each independently substituted with one or more substituents selected from the group consisting of mercapto group, hydroxyl, carboxyl, hydroxyl-substituted C1-C6 alkyl, C1-C6 amido and 3- to 6-membered nitrogen-containing heterocycloalkyl; or, $R_{10}$ and Rn together with the N atom connected therewith form a 5- to 6-membered heterocycloalkyl, optionally, the 5- to 6-membered heterocycloalkyl is substituted with one or more groups selected from the group consisting of amino, hydroxyl, carboxyl, mercapto group and hydroxyl-substituted C1-C6 alkyl;

$R_5$ is selected from the group consisting of hydrogen, deuterium, cyano, halogen, C1-C4 alkyl, C2-C4 alkenyl, deuterated C1-C4 alkyl, halogenated C1-C4 alkyl and C1-C4 alkoxy;

Y and Z are each independently selected from the group consisting of carbon and nitrogen.

In some embodiments, the benzylamine derivative is as shown by Formula (I-A):

Formula (I-A)

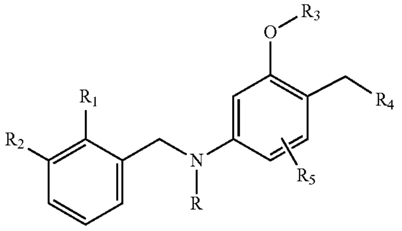

wherein, R, $R_1$, $R_2$, $R_3$, $R_4$ and $R_5$ are as described above, and $R_5$ is at the para or meta position of $—OR_3$. In some preferred embodiments, $R_5$ is at the para position of $—OR_3$.

In some embodiments, the structure of the benzylamine derivative is as shown by Formula (I-B):

Formula (I-B)

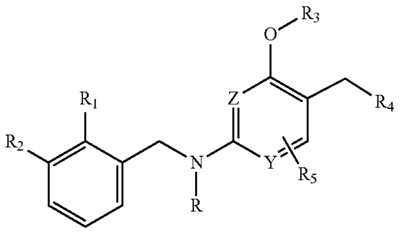

wherein, R, $R_1$, $R_2$, $R_3$, $R_4$ and $R_5$ are as described above, at least one of Z and Y is nitrogen, and $R_5$ is located at the para or meta position of $—OR_3$.

In some embodiments, the above-mentioned benzylamine derivative has a structure represented by Formula (I-C):

Formula (I-C)

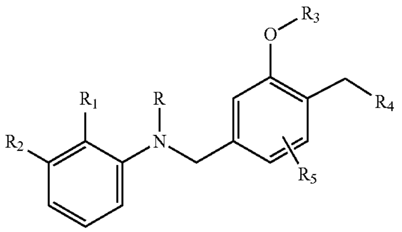

Wherein, R, $R_1$, $R_2$, $R_3$, $R_4$ and $R_5$ are as described above, and $R_5$ is located at the para or meta position of $—OR_3$.

In some embodiments, R in any of Formulas I, I-A, I-B and I-C is selected from the group consisting of hydrogen and methyl.

In some preferred embodiments, R in any of Formulas I, I-A, I-B, and I-C is hydrogen.

In some embodiments, $R_1$ in any of Formulas I, I-A, I-B and I-C is selected from the group consisting of halogen, C1-C2 alkyl and halogenated C1-C2 alkyl.

In some embodiments, $R_1$ in any of Formulas I, I-A, I-B and I-C is bromo, methyl, or trifluoromethyl.

In some embodiments, $R_1$ in any of Formulas I, I-A, I-B and I-C is selected from the group consisting of halogen and C1-C2 alkyl.

In some preferred embodiments, $R_1$ in any of Formulas I, I-A, I-B and I-C is bromo or methyl.

In some embodiments, $R_1$ in any of Formulas I, I-A, I-B and I-C is selected from the group consisting of fluoro, chloro, bromo, iodo, methoxy, methyl, cyano, deuterated methyl, and halogenated methyl.

In some embodiments, $R_2$ in any of Formulas I, I-A, I-B and I-C is selected from the group consisting of

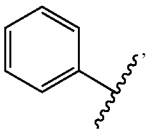,
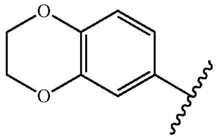
and
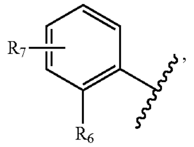, wherein $R_6$ is selected from the group consisting of hydrogen, deuterium, fluorine, chlorine, bromine, iodine, methoxy, methyl, cyano, deuterated methyl and halogenated methyl, $R_7$ is at the meta or ortho position of $R_6$ and $R_7$ is selected from the group consisting of hydrogen, —O—$(CH_2)_n$—$R_0$, —CONH—$R_0$ and —$(CH_2)_n$—$R_0$, wherein n is an integer of 1-4, $R_0$ is selected from the group consisting of cyano, hydroxyl, carboxyl, amino and a heteroatom-containing linear or cyclic hydrophilic substituent.

In some embodiments, $R_2$ in any of Formulas I, I-A, I-B and I-C is selected from

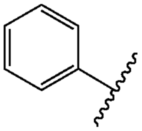
and
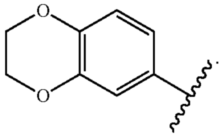.

In some embodiments, $R_3$ in any of Formulas I, I-A, I-B and I-C is selected from $R_8$—$CH_2$—, wherein $R_5$ is selected from the group consisting of hydrogen, C1-C2 alkyl, phenyl, and 5- to 6-membered heteroaryl, optionally, the C1-C2 alkyl, phenyl and 5- to 6-membered heteroaryl are each independently substituted with one cyano.

In some embodiments, $R_3$ in any of Formulas I, I-A, I-B, and I-C is selected from the group consisting of methyl, ethyl,

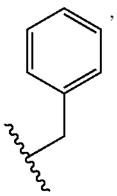,
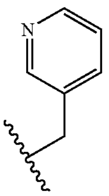,
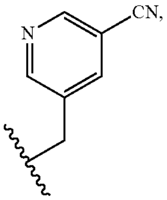
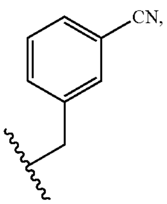
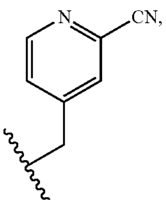
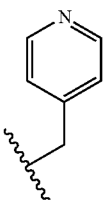,

-continued

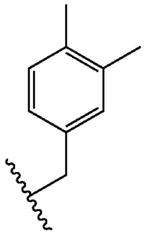,
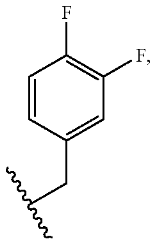
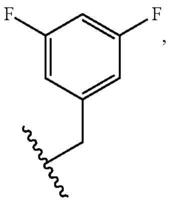,
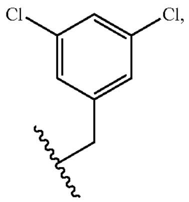
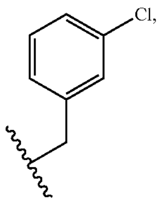
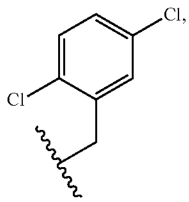
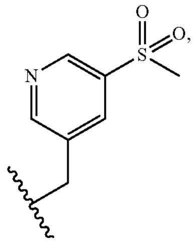
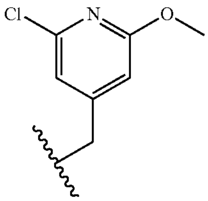,
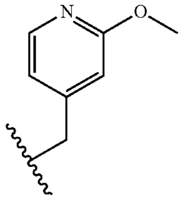,
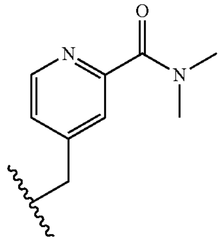,
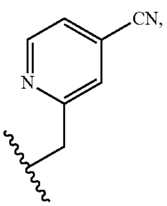
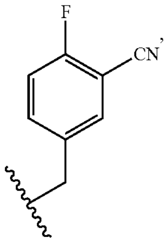,
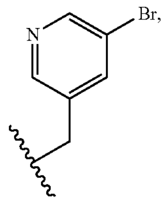
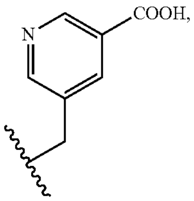
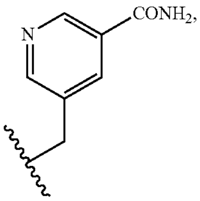
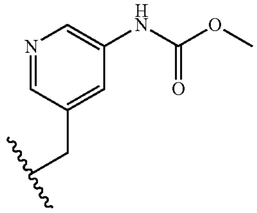,
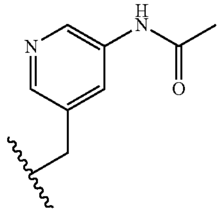, -continued

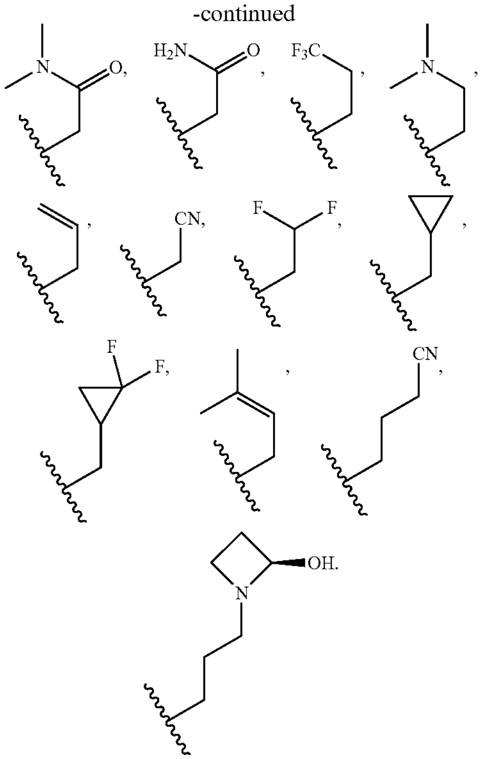

In some embodiments, $R_3$ in any of Formulas I, I-A, I-B and I-C is selected from the group consisting of methyl, ethyl,

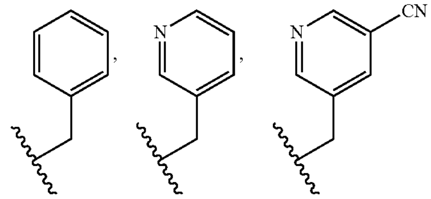

and

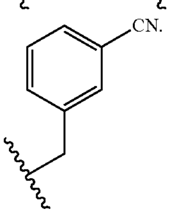

In some embodiments, $R_4$ in any of Formulas I, I-A, I-B and I-C is selected from the group consisting of the fragment of amino acid and —$NR_{10}R_{11}$, wherein $R_{10}$ and Ru are each independently selected from the group consisting of hydrogen, deuterium and C1-C6 alkyl, optionally, the C1-C6 alkyl is substituted with one or more substituents selected from the group consisting of mercapto group, hydroxyl, carboxyl, hydroxyl-substituted C1-C4 alkyl, C1-C4 amido, and 5- to 6-membered nitrogen-containing heterocycloalkyl; or, $R_{10}$ and Ru together with the N atom connected therewith form a 5- to 6-membered heterocycloalkyl, optionally, the 5- to 6-membered heterocycloalkyl is substituted with one or more groups selected from the group consisting of amino, hydroxyl, carboxyl, mercapto group and hydroxyl-substituted C1-C4 alkyl; the fragment of amino acid is selected from the fragment obtained by losing one hydrogen of the amino that shares a carbon atom with the carboxyl. In some preferred embodiments, the amino acid is selected from the group consisting of glycine, alanine, proline, hydroxyproline, serine, threonine, aspartic acid, asparagine, glutamic acid, glutamine, cysteine histidine, lysine, arginine, pyroglutamic acid,

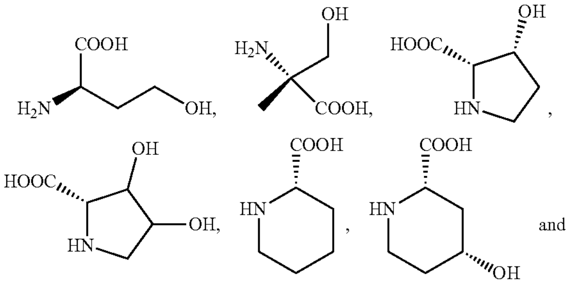

and

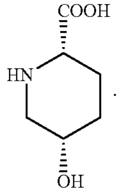

In some preferred embodiments, the amino acid is selected from serine, hydroxyproline and asparagine.

In some embodiments, $R_4$ in any of Formulas I, I-A, I-B and I-C is selected from the group consisting of amino, hydroxyl, carboxyl,

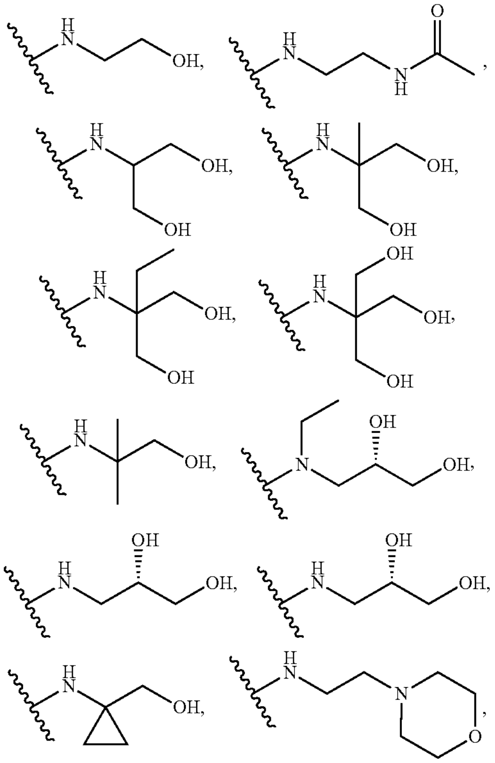

-continued

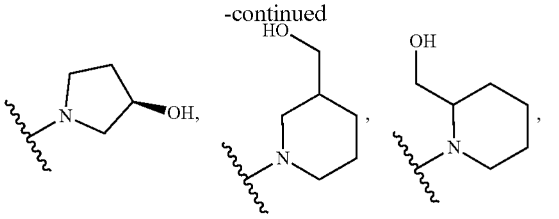

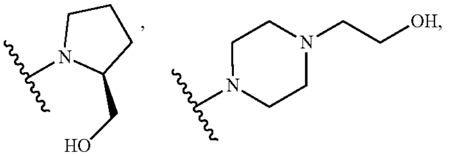

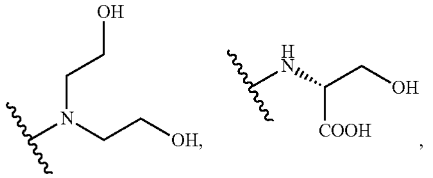

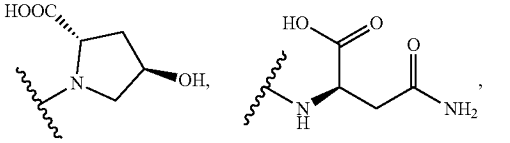

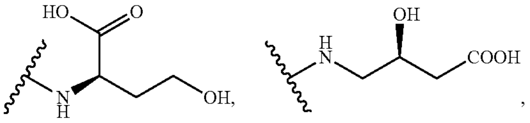

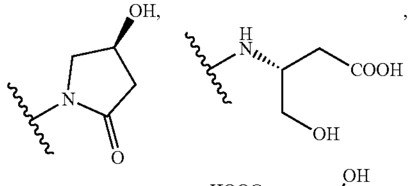

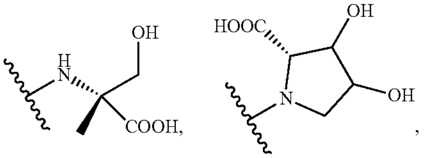

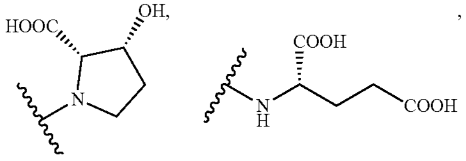

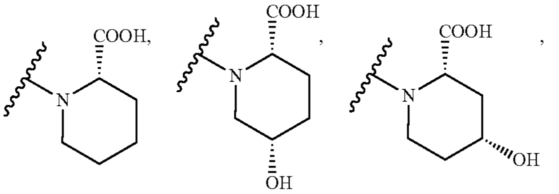

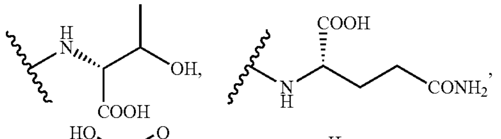

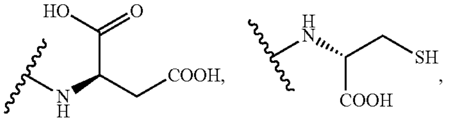

-continued

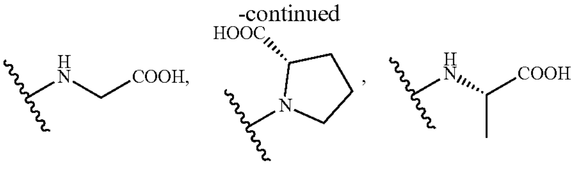

and stereoisomers of the above structures.

In some embodiments, $R_4$ in any of Formulas I, I-A, I-B and I-C is selected from the group-consisting of

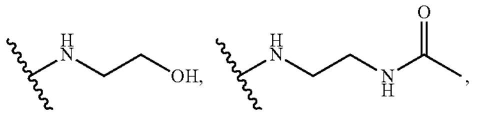

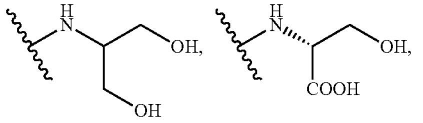

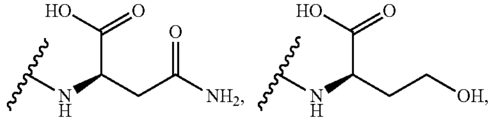

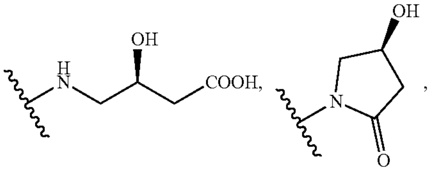

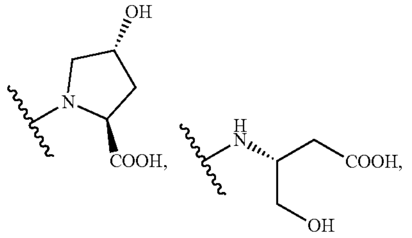

and stereoisomers of the above structures.

In some embodiments, $R_5$ in any of Formulas I, I-A, I-B and I-C is selected from the group consisting of hydrogen, deuterium, halogen, C1-C2 alkyl and C1-C2 alkoxy, such as hydrogen, chlorine, methoxy or methyl.

In some embodiments, $R_5$ in any of Formulas I, I-A, I-B and I-C is selected from the group consisting of fluorine, chlorine, bromine, iodine, methoxy, methyl, cyano, deuterated methyl, halogenated methyl, ethyl, vinyl and ethoxy.

In some embodiments, $R_5$ in any of Formulas I, I-A, I-B and I-C is selected from the group consisting of hydrogen, deuterium, halogen, and C1-C2 alkyl, such as hydrogen, chlorine, or methyl.

In some embodiments, in any of Formulas I, I-A, I-B and I-C, R is hydrogen; $R_5$ is selected from the group consisting of hydrogen, chlorine, and methyl, and $R_5$ is in the para position of —$OR_3$.

In some embodiments, in any of Formulas I, I-A, I-B, and I-C,

R is selected from hydrogen and C1-C8 alkyl;

$R_1$ is selected from halogen and C1-C4 alkyl;

$R_2$ is selected from the group consisting of

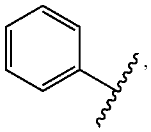,
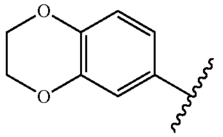
and
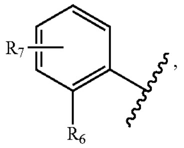, wherein $R_6$ is selected from the group consisting of halogen, C1-C4 alkyl, deuterated C1-C4 alkyl, halogenated C1-C4 alkyl and C1-C4 alkoxy, $R_7$ is at the meta or ortho position of $R_6$ and $R_7$ is selected from the group consisting of hydrogen, $-O-(CH_2)_n-R_0$, $-CONH-R_0$ and $-(CH_2)_n-R_0$, wherein n is an integer of 1-4, $R_0$ is cyano, hydroxyl, carboxyl, amino or a heteroatom-containing linear or cyclic hydrophilic substituent;

$R_3$ is selected from $R_8-CH_2-$, wherein $R_8$ is selected from the group consisting of 6- to 10-membered aryl substituted with one or more cyano groups and 5- to 10-membered heteroaryl optionally substituted with one or more cyano groups;

$R_4$ is selected from the group consisting of

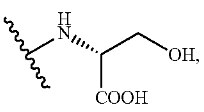
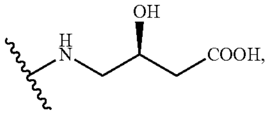
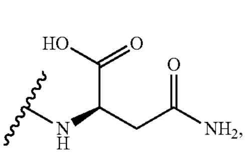
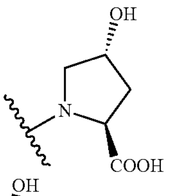
and
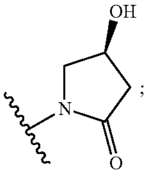

$R_5$ is selected from the group consisting of halogen and C1-C4 alkyl, and $R_5$ is at the para position of $-OR_3$;

Y and Z are each independently selected from the group consisting of carbon and nitrogen.

In some embodiments, in Formula I-A,

R is selected from the group consisting of hydrogen and methyl;

$R_1$ is selected from the group consisting of halogen and C1-C2 alkyl;

$R_2$ is selected from the group consisting of

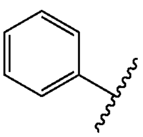
or
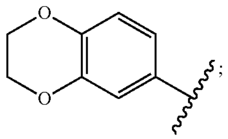

$R_3$ is selected from the group consisting of

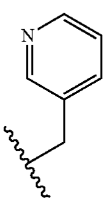
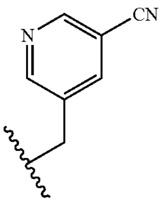
and
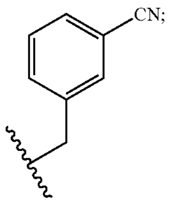

$R_4$ is selected from the group consisting of

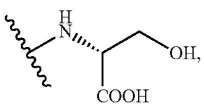
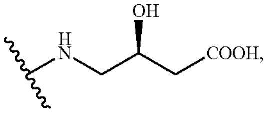
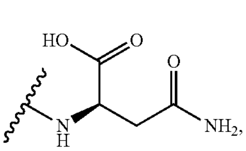
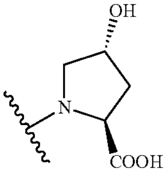
and
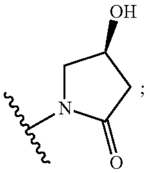

$R_5$ is selected from the group consisting of halogen and C1-C4 alkyl, and $R_5$ is at the para position of $-OR_3$.

In some embodiments, in any of Formulas I, I-A, I-B and I-C,

R is hydrogen;

$R_1$ is bromine or methyl;

$R_2$ is

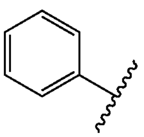
or
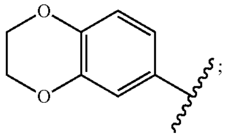

$R_3$ is selected from the group consisting of methyl,

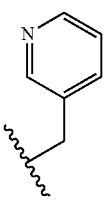
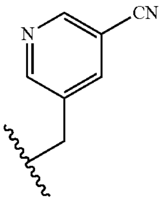
and
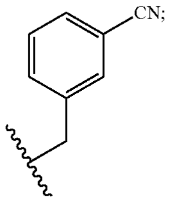

$R_4$ is selected from
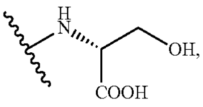
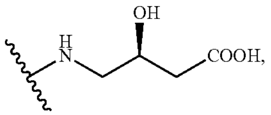
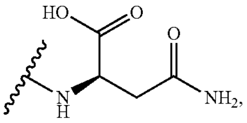
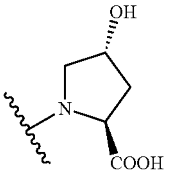
and
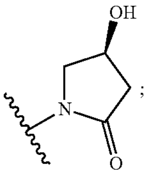
$R_5$ is selected from the group consisting of hydrogen, chlorine and methyl, and $R_5$ is at the para position of $-OR_3$.
In some embodiments, the benzylamine derivative is selected from:
1
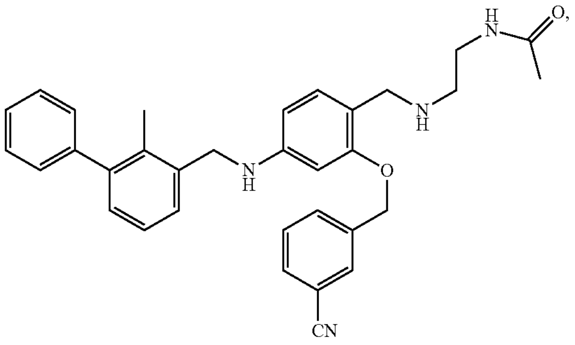
2
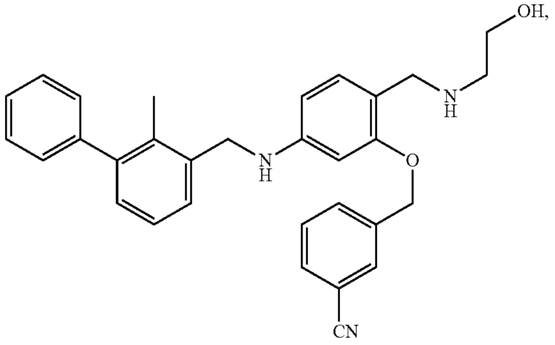
-continued
3
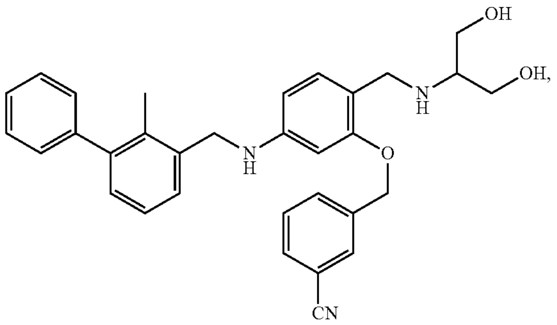
4
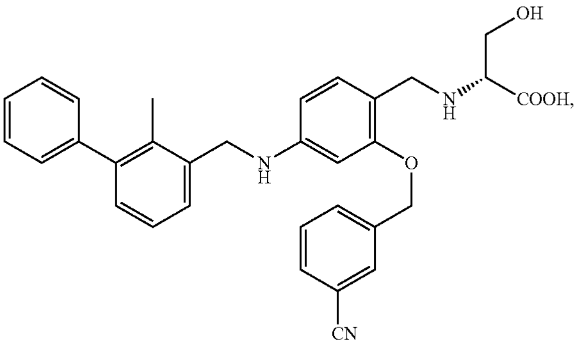
5
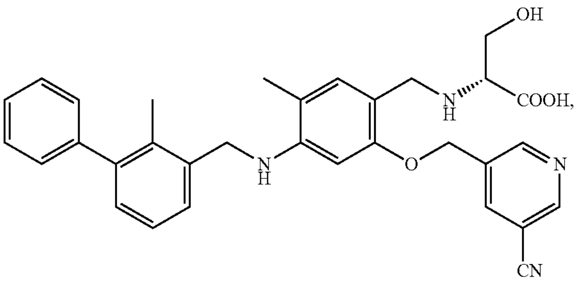
6
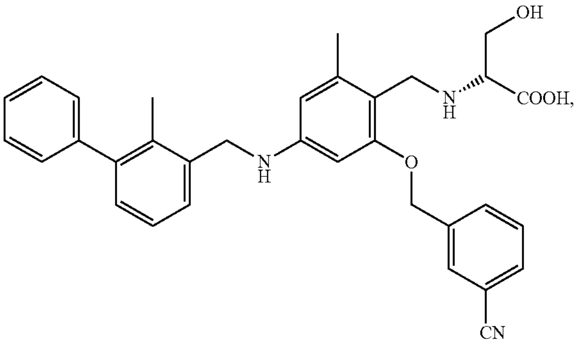

-continued
7
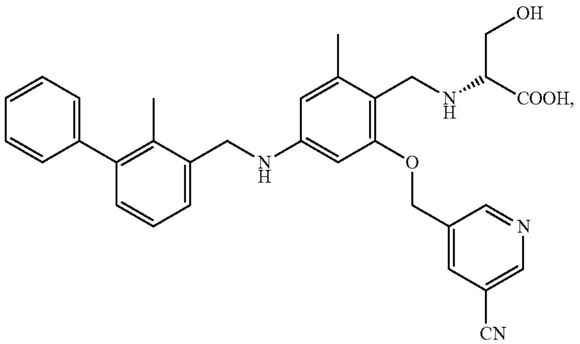
8
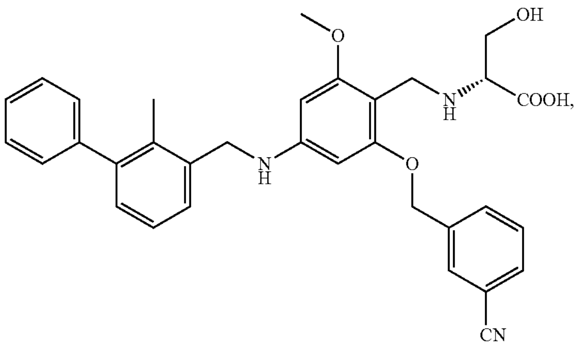
9
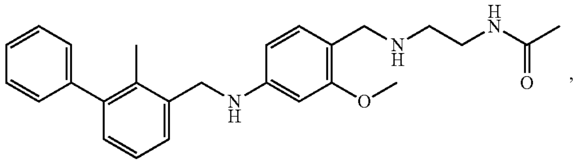
10
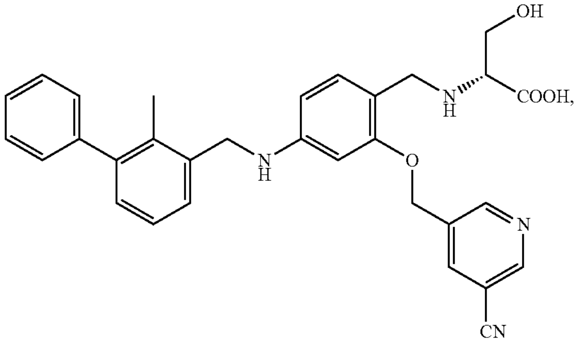
11
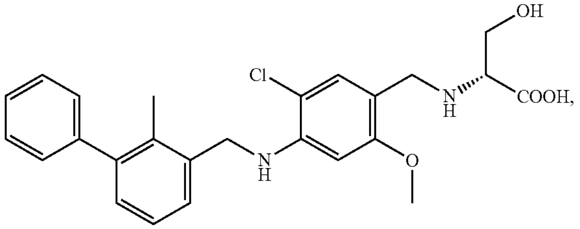
-continued
12
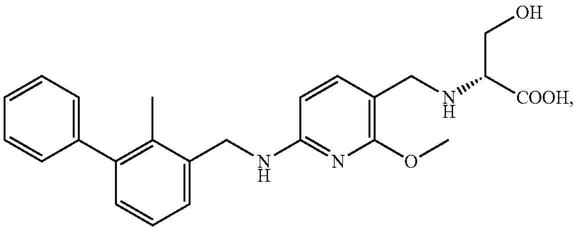
13
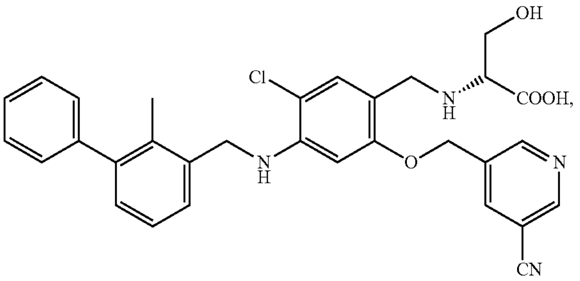
14
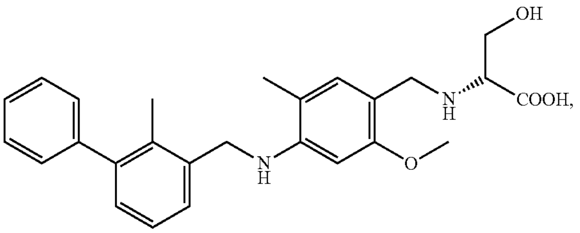
15
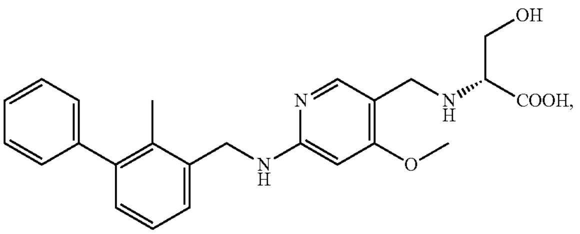
16
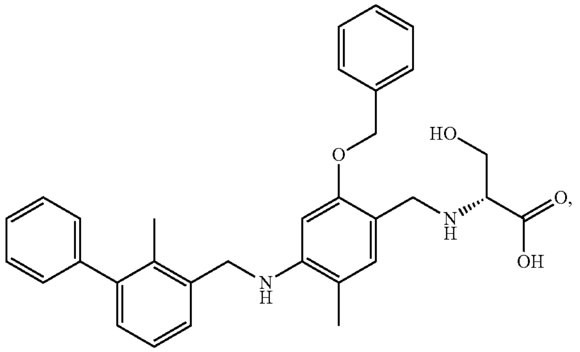

-continued
17
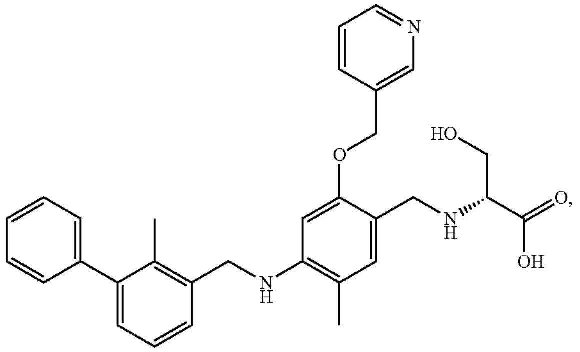
18
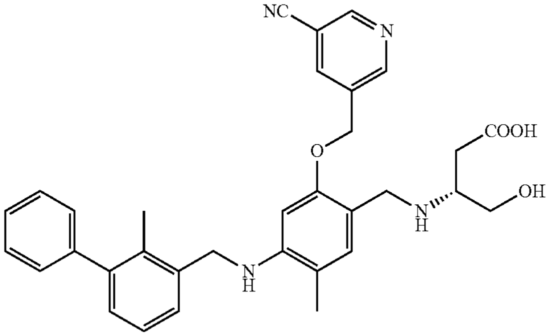
19
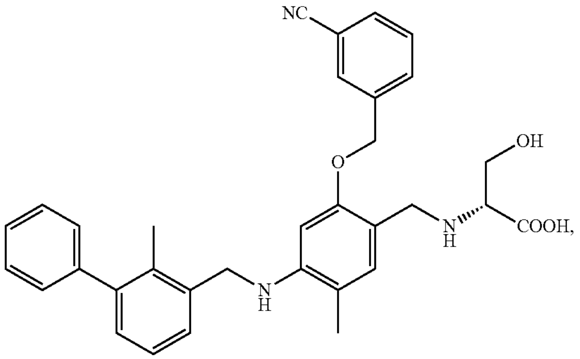
20
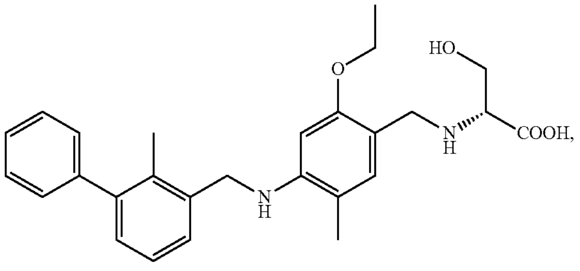
-continued
21
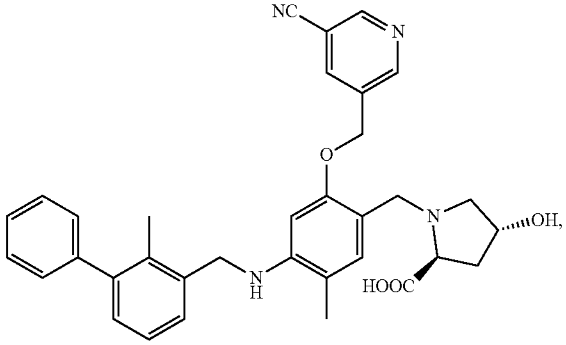
22
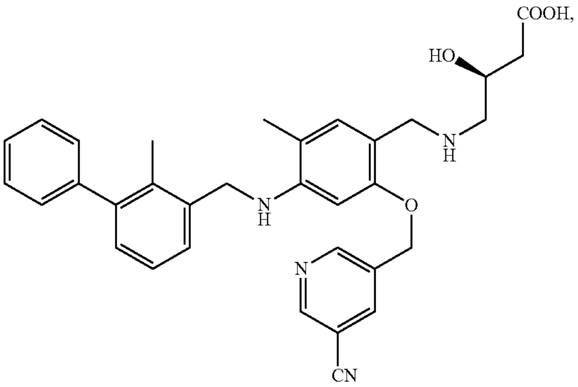
23
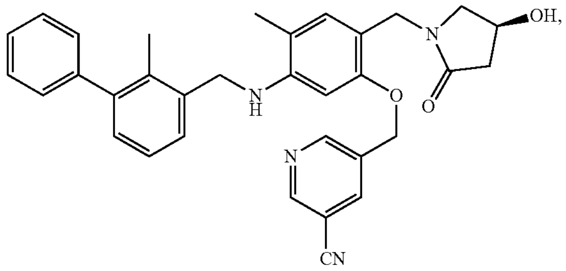
24
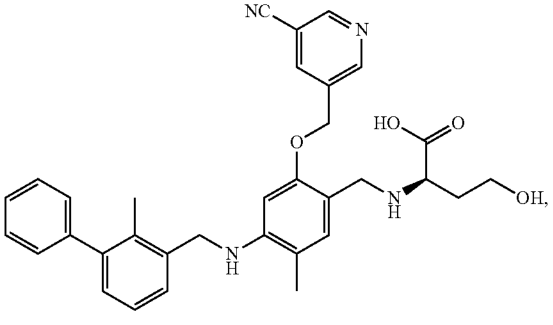

-continued
25
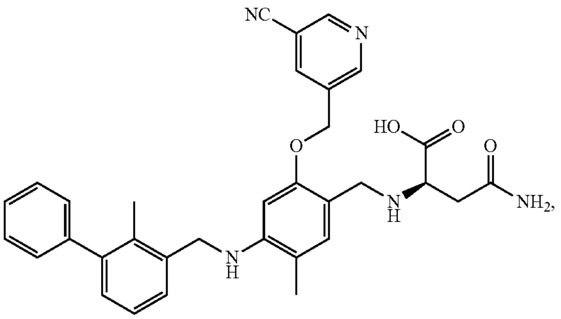
26
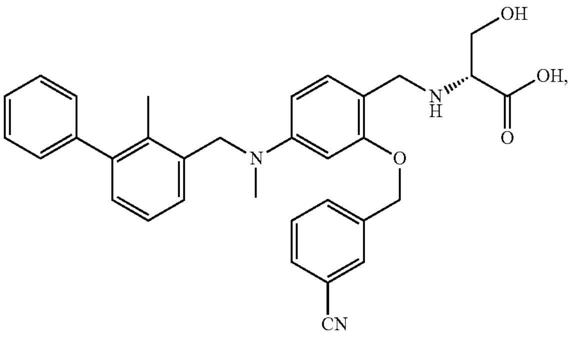
27
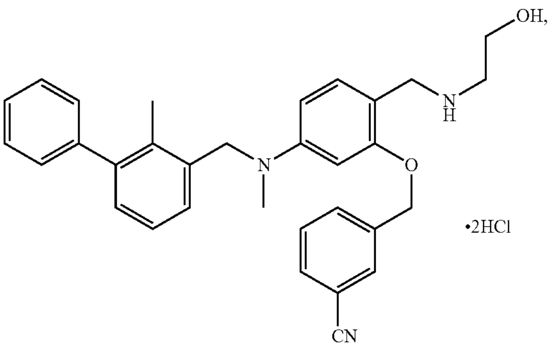
•2HCl
28
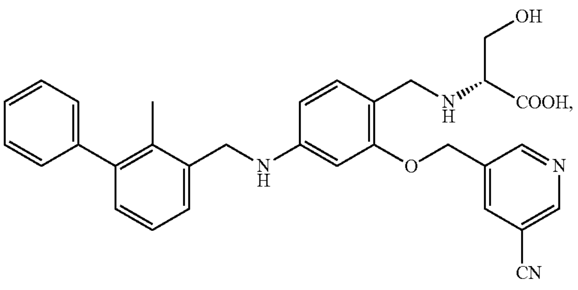
-continued
29
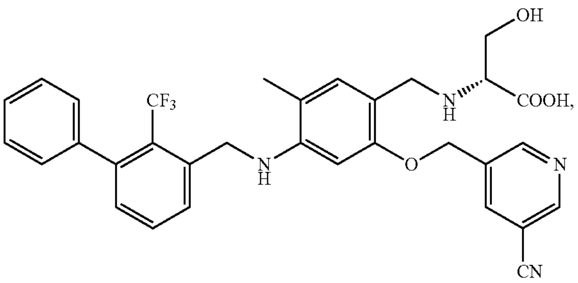
30
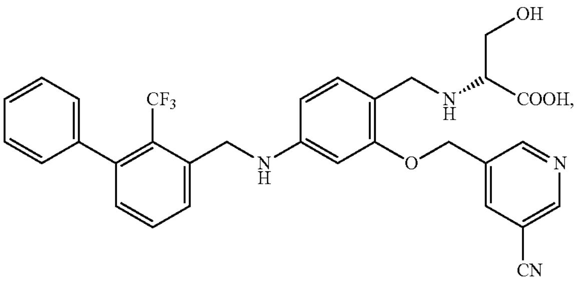
31
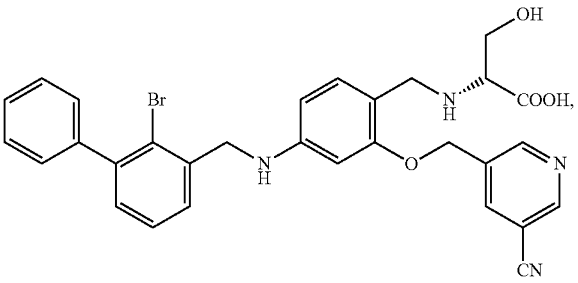
32
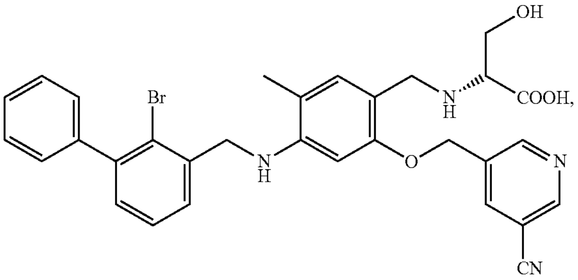
33
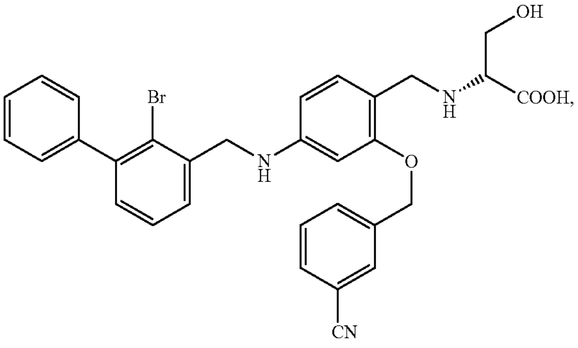

-continued

34

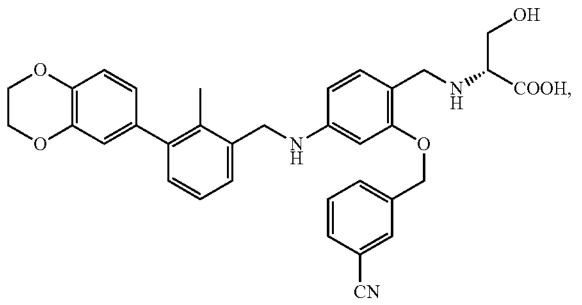

35

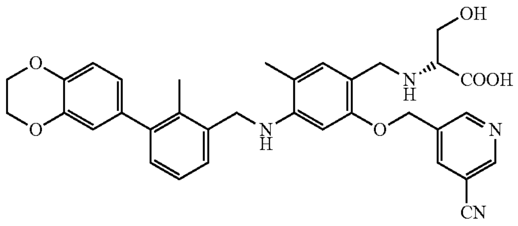

and

36

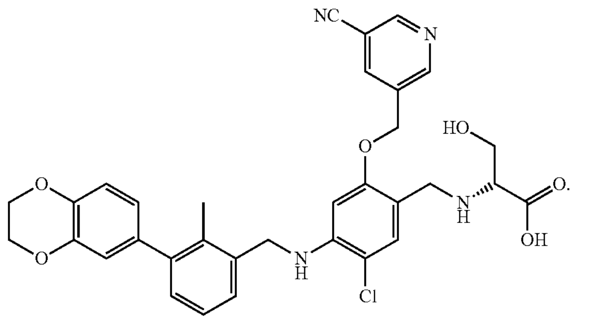

In some embodiments, the pharmaceutically acceptable salt of the benzylamine derivative is selected from the group consisting of a salt formed with an organic or inorganic acid (e.g., hydrochloride, sulfate, phosphate, hydrobromide, hydroiodide, nitrate, bisulfate, oxalate, formate, acetate, citrate, tartrate, sulfonate, benzoate, trifluoroacetate, maleate or citrate, etc.), a salt formed with an alkali metal or alkaline earth metal (e.g., lithium salt, sodium salt, potassium salt, magnesium salt and calcium salt or ammonium salt, etc.), and a salt formed with an organic base (e.g., methylamine salt, ethylamine salt, triethylamine salt, piperidine salt, morpholine salt, etc.). In some embodiments, the pharmaceutically acceptable salt of the benzylamine derivative is a hydrochloride salt thereof.

As used herein, the term "halogen" refers to fluorine, chlorine, bromine and iodine.

As used herein, the term "C1-C8 alkyl" refers to straight or branched alkyl containing 1-8 carbon atoms, including C1-C6 alkyl, C1-C5 alkyl, C1-C4 alkyl and C1-C2 alkyl and so on. Typical examples thereof are methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, etc.

As used herein, the term "C1-C4 alkoxy" refers to a group formed in the form of C1-C4 alkyl-O—, wherein "C1-C4 alkyl" is as defined above, for example C1-C3 alkoxy and C1-C2 alkoxy, etc. Typical examples are methoxy, ethoxy, propoxy, isopropoxy, butoxy, isobutoxy, tert-butoxy and the like.

As used herein, the term "C2-C4 alkenyl" refers to a straight or branched hydrocarbonyl containing 2-4 carbon atoms with at least one carbon-carbon double bond. Typical examples thereof are vinyl, propenyl, 2-propenyl, butenyl, 2-butenyl, butadienyl and the like.

As used herein, the term "deuterated" refers to a group obtained by substituting at least one hydrogen atom in a group with isotope deuterium, for example, a deuterated C1-C4 alkyl.

As used herein, the term "halogenated" refers to a group obtained by substituting at least one hydrogen atom in the group with a halogen as previously described, for example, halogenated C1-C4 alkyl, halogenated C1-C4 alkoxy, etc. Typical example thereof is trifluoromethyl.

As used herein, the term "hydrophilic substituent" refers to a group that is prone to bind with water, the hydrophilic group typically comprises at least one hydrophilic functional group, such as hydroxyl, amino, carboxyl, sulfonic acid group, phosphoric acid group, etc. In some embodiments, the hydrophilic substituent is a heteroatom-containing linear or cyclic hydrophilic substituent. Specific examples include, but are not limited to

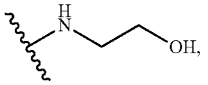 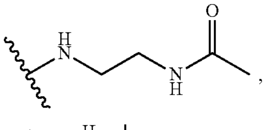

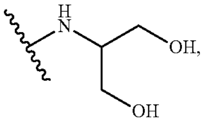 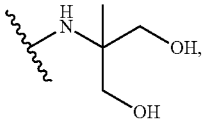

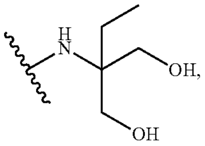 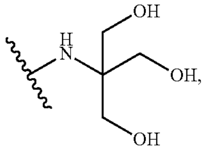

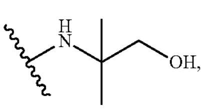 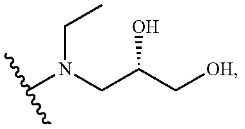

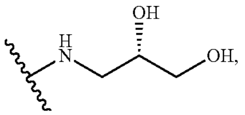 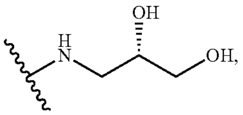

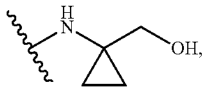 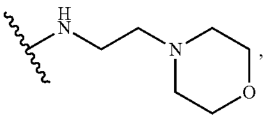

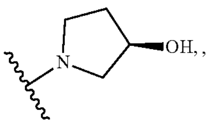 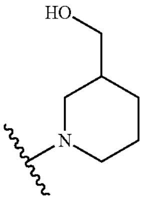 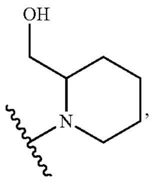

-continued

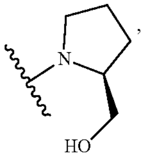

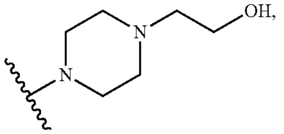

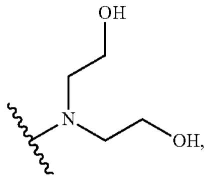

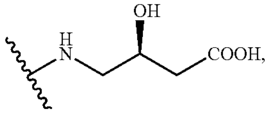

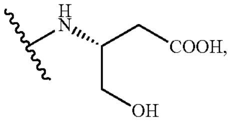

and the like.

As used herein, the term “3- to 6-membered cycloalkyl” refers to a saturated cyclic hydrocarbonyl containing 3 to 6 ring-forming carbon atoms, for example, 3-membered cycloalkyl, 4-membered cycloalkyl, 5-membered cycloalkyl or 6-membered cycloalkyl. Typical examples include cyclopropyl, cyclobutyl, cyclopentyl, cyclohexyl, and the like.

As used herein, the term “3- to 6-membered heterocycloalkyl” refers to a saturated cyclic hydrocarbonyl containing 3 to 6 ring members, wherein at least one (e.g., 1, 2, 3 or 4) ring members are heteroatoms selected from the group consisting of N, O and S. For example, 3-membered heterocycloalkyl, 4-membered heterocycloalkyl, 5-membered heterocycloalkyl or 6-membered heterocycloalkyl. For example, 3- to 6-membered nitrogen-containing heterocycloalkyl. Typical examples thereof include ethylene oxide, butylene oxide, pyrrolidinyl, tetrahydrofuranyl, imidazolidinyl, pyrazolidinyl, thiazolidinyl, isothiazolidinyl, isoxazolidinyl, morpholinyl, thiomorpholinyl, piperazinyl, piperidinyl, oxazinyl, etc.

As used herein, the term “6- to 10-membered aryl” refers to an aromatic group composed of 6 to 10 ring-forming carbon atoms, such as phenyl or naphthyl.

As used herein, the term “5- to 10-membered heteroaryl” refers to an aromatic group containing 5-10 ring members, wherein at least one (e.g., 1, 2, 3, or 4) ring members is a heteroatom selected from the group consisting of N, O and S, the heteroaryl may be a monocyclic heteroaryl, bicyclic heteroaryl or polycyclic heteroaryl. For example, 5- to 6-membered heteroaryl and the like. Typical examples are furyl, thienyl, pyrrolyl, thiazolyl, isothiazolyl, thiadiazolyl, oxazolyl, isoxazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,2,3-triazinyl and the like.

As used herein, the term “C1-C4 alkylsulfonyl” refers to a group formed in the form of C1-C4 alkyl-$SO_2$—, wherein “C1-C4 alkyl” is as previously defined, for example C1-C3 alkylsulfonyl and C1-C2 alkylsulfonyl, etc. Typical examples are methanesulfonyl and the like.

As used herein, the term “C1-C6 amido” refers to a group formed in the form of C1-C5 alkyl-CONH—, wherein “C1-C5 alkyl” is as previously defined, for example C1-C4 alkyl amido and C1-C2 alkyl amide, etc. Typical examples are formamido, acetamido, and the like.

As used herein, the term “stereoisomer” refers to an isomer resulting from difference in the spatial arrangement of atoms in a molecule, including cis-trans isomer, enantiomer, and diastereomer. The stereoisomer of the present invention comprises any of the above-mentioned stereoisomer of the benzylamine derivative, and a mixture formed with one or more stereoisomers in any ratio.

As used herein, the term “solvate” refers to a stably existing complex formed by interaction between the benzylamine derivative described herein and a solvent (e.g., organic solvents such as methanol or ethanol, or water) to form stably existing complexes. In some embodiments, the solvent may serve as a structural element of the crystal lattice of the benzylamine derivative. In some embodiments, the solvent may be present in a stoichiometric or non-stoichiometric ratio.

As used herein, the term “prodrug” refers to a derivative of the benzylamine derivative described herein that contains a biologically reactive functional group, which could generate the benzylamine derivative by cleavage or other biochemical reaction under biochemical reaction conditions, comprising but not limited to phosphate, ester, amide and ureide of the benzylamine derivative described herein that are hydrolyzable under biochemical conditions.

In another aspect, the present invention provides a method for preparing the compound described in the first aspect, specifically as follows:

when the benzylamine derivative of general Formula (I) has a structure represented by Formula (I-A), the method for preparing the same is selected from the following Methods I to III:

Method I

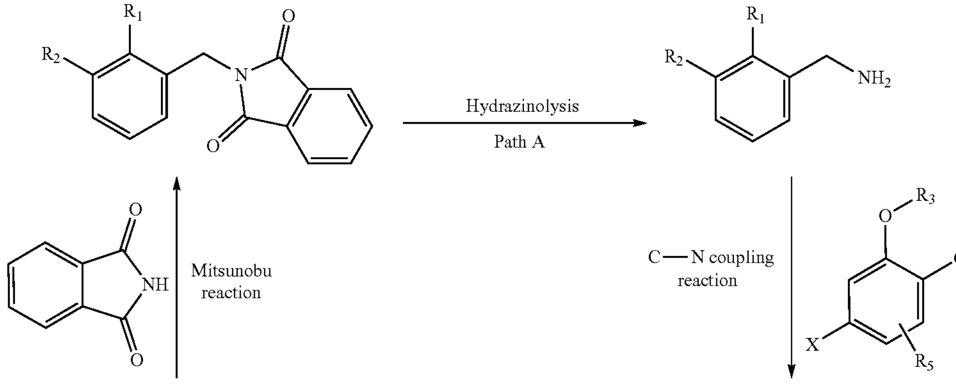

-continued
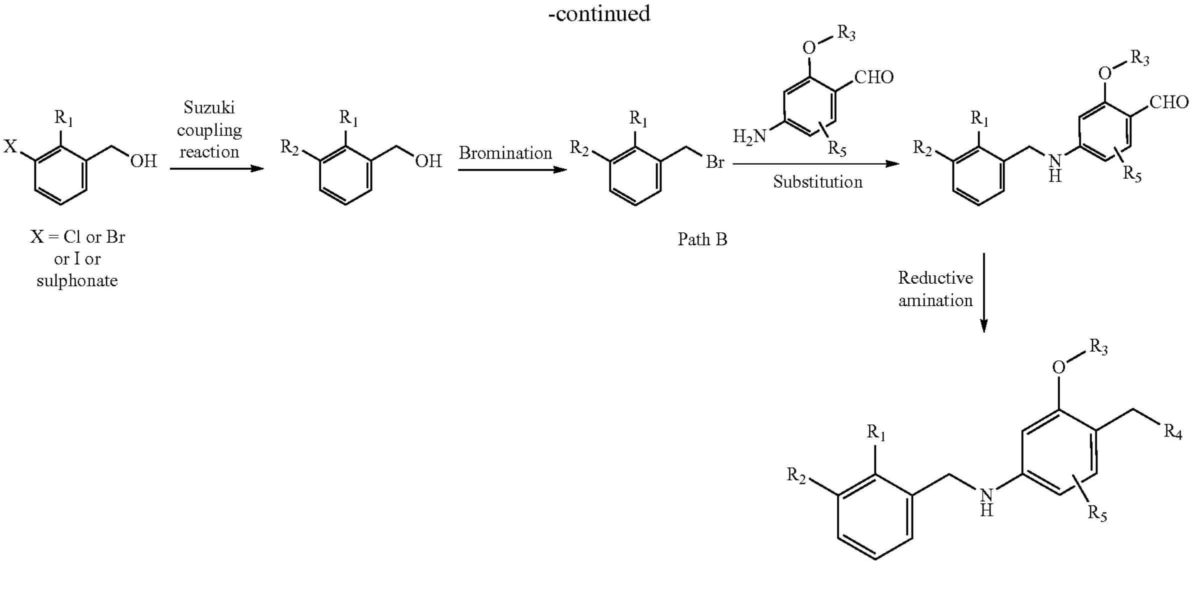
Method II
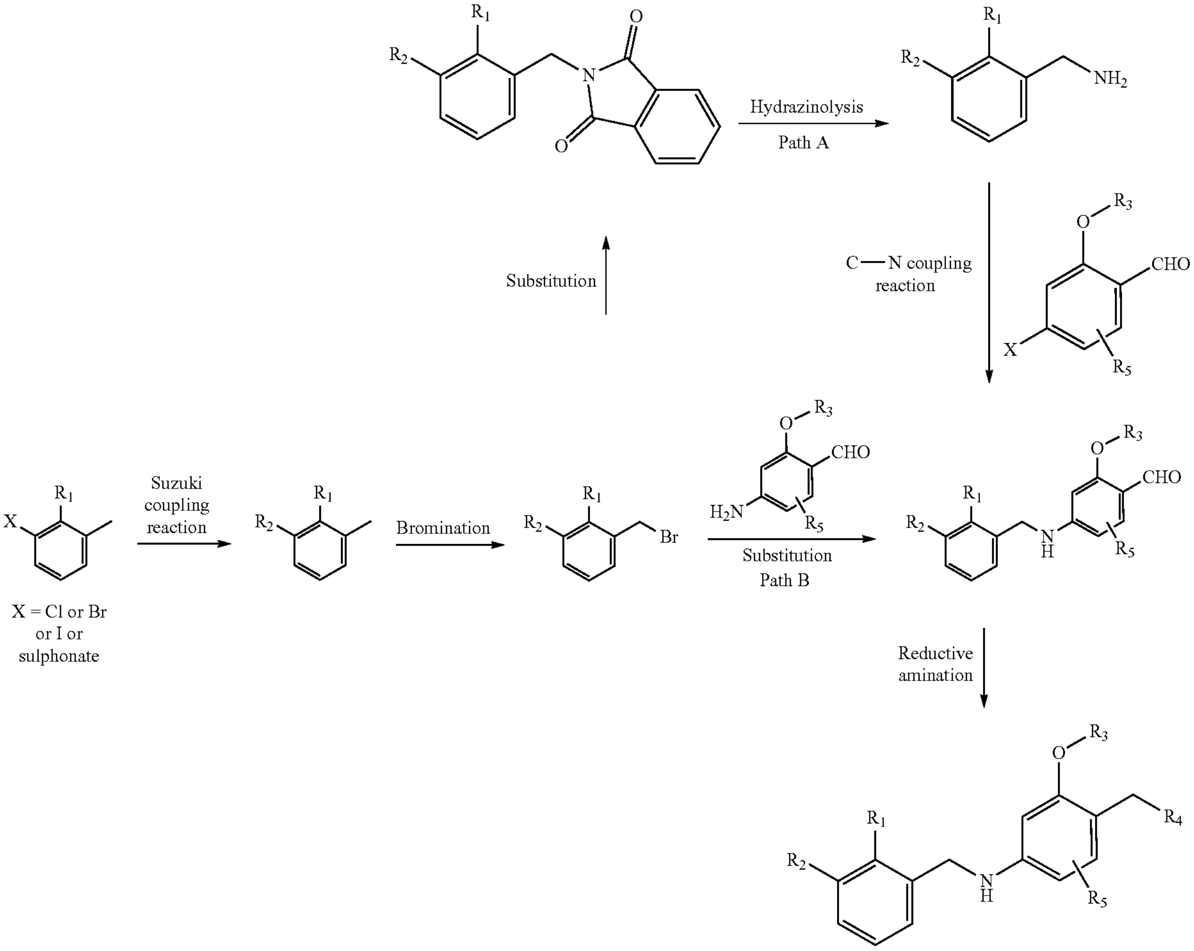

Method III

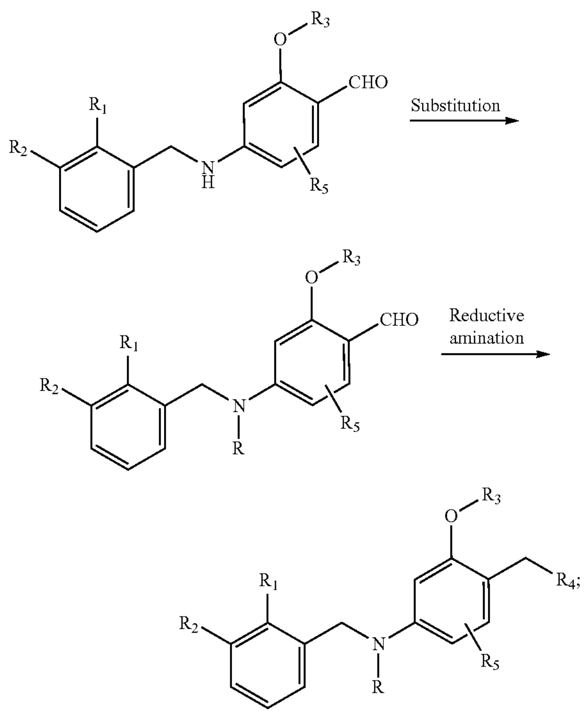

when the benzylamine derivative of the general Formula (I) has the structure represented by Formula (I-B), the method for preparing the same is selected from the following Method IV or V:

Method IV

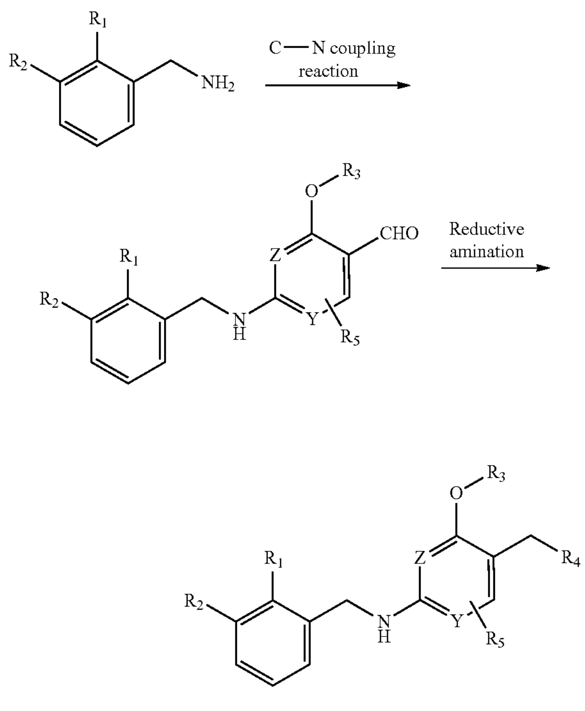

Method V

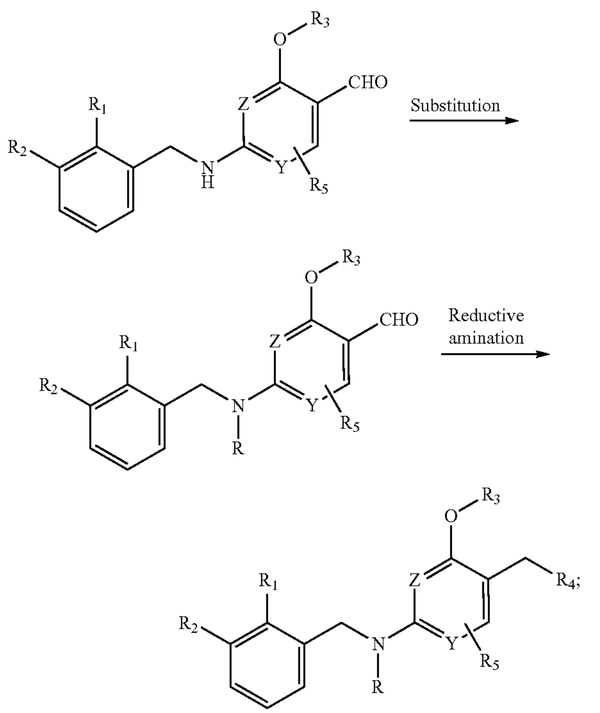

when the benzylamine derivative of the general Formula (I) has the structure represented by Formula (I-C), the method for preparing the same is selected from the following Method VI or VII:

Method VI

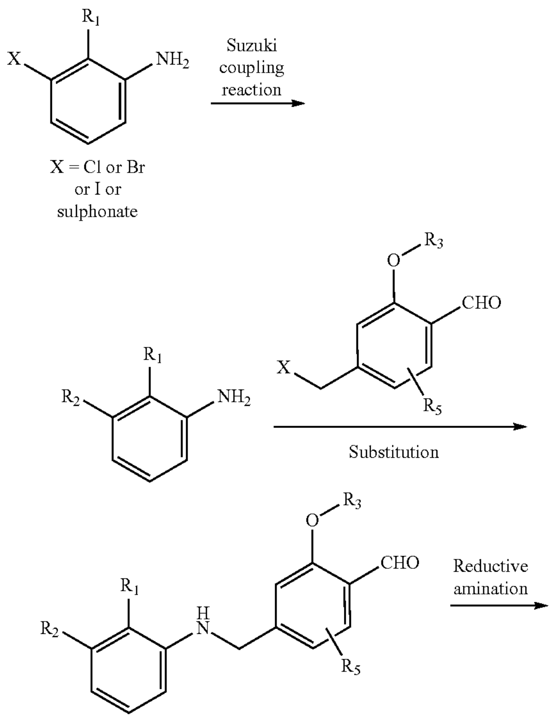

-continued

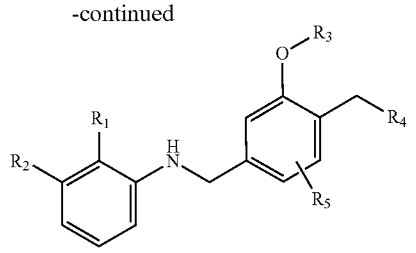

Method VII

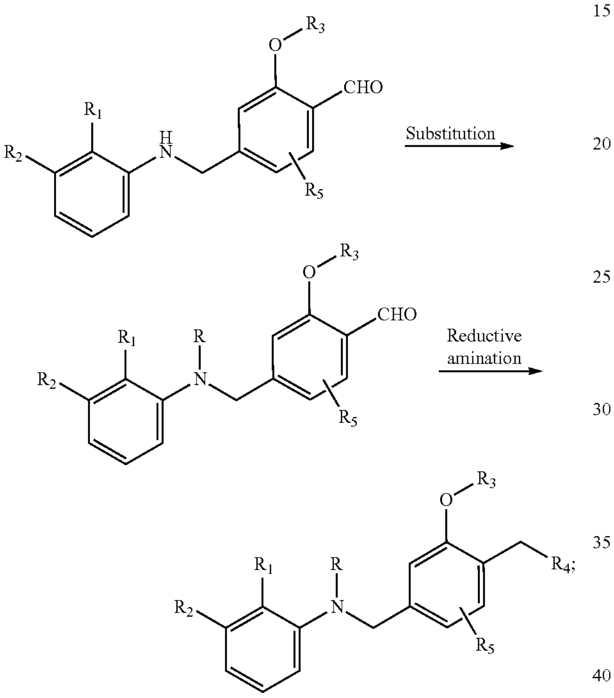

unless otherwise specified, the substituents appeared in the above compounds are as described in any one of the first aspect of the present invention.

In another aspect, the present invention provides a pharmaceutical composition comprising the benzylamine derivative, or pharmaceutically acceptable stereoisomer, salt, solvate or prodrug thereof, according to any one of the first aspect of the present invention, and one or more pharmaceutically acceptable carriers or excipients.

The carriers refer to substances used to improve the selectivity, efficacy and/or safety of the drug during delivery. It is mainly used to control drug release, and can also be used to improve the pharmacokinetic properties, especially bioavailability, of the drug. The excipients refer to substances other than the active ingredient in the pharmaceutical formulation, which is mainly used for improving long-term stability, filling solid preparation (hence, also often used to specifically refer to "filler") or enhancing the efficacy of product (e.g., promoting absorption, reducing viscosity or increasing solubility, etc.). Depending on the route of administration or form of administration, those skilled in the art can select suitable carriers and excipients on the basis of known theory and experience. In some embodiments, the carrier or excipient includes, but is not limited to, magnesium stearate, alumina, glycerol, lecithin, serum albumin, cellulosic material, PEG, beeswax, lanolin, potassium sorbate, lactose, starch, coconut oil and vegetable oil, etc.

The pharmaceutical composition of the present invention can be prepared into various forms according to different routes of administration.

In some embodiments, the pharmaceutical composition can be administered in any of the following ways: oral administration, inhalation spray, rectal administration, nasal administration, buccal administration, vaginal administration, topical administration, parenteral administration such as subcutaneous administration, intravenous administration, intramuscular administration, intraperitoneal administration, intrathecal administration, intraventricular administration, intrasternal and intracranial injection or infusion, or administered via an explanted reservoir. Of these, oral, intraperitoneal or intravenous administration is preferred.

For oral administration, the benzylamine derivative, or a pharmaceutically acceptable stereoisomer, salt, solvate or prodrug thereof, can be made into any orally acceptable preparation, including but not limited to tablets, capsules, aqueous solution or suspension. Among them, the commonly used carriers for tablet include lactose and corn starch, and lubricant such as magnesium stearate may also be added. Commonly used diluents for capsules include lactose and dried cornstarch. Aqueous suspension is usually prepared by mixing the active ingredient with suitable emulsifying agents and suspending agents. If desired, some sweetening, flavoring or coloring agents may also be added to the above oral preparations.

For rectal administration, the benzylamine derivative, or a pharmaceutically acceptable stereoisomer, salt, solvate or prodrug thereof, can generally be made into the form of suppository, which is prepared by mixing the drug with a suitable non-irritating excipient. The excipient is solid at room temperature, but melts at rectal temperature to release the drug. Such excipient includes cocoa butter, beeswax and polyethylene glycol.

For topical administration, especially when treating affected surfaces or organs easily accessible by topical administration, such as eye, skin or lower intestinal neurological diseases, the benzylamine derivative, or pharmaceutically acceptable stereoisomer, salt, solvate or prodrug thereof, can be made into different topical preparations according to different affected surfaces or organs, and the specific instructions are as follows:

For topical administration to the eye, the benzylamine derivative, or a pharmaceutically acceptable stereoisomer, salt, solvate or prodrug thereof, can be formulated into the form of a micronized suspension or solution, the carrier used is isotonic sterile saline with a certain pH, which may or may not be added with a preservative such as benzyl alkoxide chloride. In addition, for ophthalmic use, the compound can be formulated into the form of an ointment such as petrolatum ointment.

For topical administration to the skin, the benzylamine derivative, or a pharmaceutically acceptable stereoisomer, salt, solvate or prodrug thereof, can be made into the form of a suitable ointment, lotion or cream, in which the active ingredient is suspended or dissolved in one or more carriers. The carriers that can be used in ointment here include, but are not limited to: mineral oil, liquid petrolatum, white petrolatum, propylene glycol, polyethylene oxide, polypropylene oxide, emulsified wax and water; the carriers that can be used in lotion or cream include, but are not limited to: mineral oil, sorbitan monostearate, Tween 60, cetyl ester wax, cetenylaryl alcohol, 2-octyldodecanol, benzyl alcohol and water.

For topical administration to the lower intestinal tract, the benzylamine derivative, or a pharmaceutically acceptable stereoisomer, salt, solvate or prodrug thereof, can be made into the above-mentioned rectal suppository preparation or suitable form of enema preparation. In addition, topical transdermal patches can also be used.

The benzylamine derivative, or a pharmaceutically acceptable stereoisomer, salt, solvate or prodrug thereof, can also be administered in the form of sterile injectable preparation, including sterile injectable aqueous or oil suspension, or sterile injectable solution. Among them, the carriers and solvents that can be used are water, Ringer's solution and isotonic sodium chloride solution. In addition, sterile non-volatile oil such as monoglyceride or diglyceride can also be used as a solvent or suspending medium.

The drug of the above-mentioned various dosage forms can be prepared according to the conventional methods in the pharmaceutical field.

In another aspect, the present invention provides use of the benzylamine derivative, or a pharmaceutically acceptable stereoisomer, salt, solvate or prodrug thereof, or the pharmaceutical composition in the manufacture of a medicament for prevention or treatment of a disease associated with PD-1/PD-L1.

In another aspect, the present invention provides the benzylamine derivative, or a pharmaceutically acceptable stereoisomer, salt, solvate or prodrug thereof, or the pharmaceutical composition, for use in the prevention or treatment of a disease associated with PD-1/PD-LL.

In another aspect, the present invention provides a method for preventing or treating a disease associated with PD-1/PD-L1, comprising a step of administering to a subject in need thereof an effective amount of the benzylamine derivative, or a pharmaceutically acceptable stereoisomer, salt, solvate or prodrug thereof, or the pharmaceutical composition.

In another aspect, the present invention provides a method for inhibiting PD-1/PD-L1 interaction, comprising a step of administering to a subject in need thereof an effective amount of the benzylamine derivative, or a pharmaceutically acceptable stereoisomer, salt, solvate or prodrug thereof, or the pharmaceutical composition.

In another aspect, the present invention provides a method for increasing an immune response comprising a step of administering to a subject in need thereof an effective amount of the benzylamine derivative, or a pharmaceutically acceptable stereoisomer, salt, solvate or prodrug thereof, or the pharmaceutical composition.

The disease associated with PD-1/PD-L1 described herein comprises tumor, infectious disease, and autoimmune disease.

In some embodiments, the tumor is one or more selected from the group consisting of tumor of digestive system, tumor of urinary system, hematological tumor, tumor of nervous system, tumor of reproductive system, skin cancer, lung cancer, breast cancer, head and neck cancer, brain tumor, glioma, nasopharyngeal tumor and so on.

In some embodiments, the infectious disease is selected from one or more infections caused by microorganisms. In some embodiments, the infection is an infection caused by bacteria and viruses.

In some embodiments, the autoimmune disease is selected from the group consisting of chronic lymphocytic thyroiditis, hyperthyroidism, insulin-dependent diabetes mellitus, myasthenia gravis, ulcerative colitis, pernicious anemia accompanied with chronic atrophic gastritis, pulmonary hemorrhagic nephritis syndrome, pemphigus (e.g., pemphigus vulgaris), pemphigoid, primary biliary cirrhosis, multiple cerebral sclerosis, acute idiopathic polyneuritis, etc., systemic lupus erythematosus, rheumatoid arthritis, systemic vasculitis, scleroderma, dermatomyositis, mixed connective tissue disease, autoimmune hemolytic anemia, thyroid autoimmune disease, Sjogren's syndrome, ankylosing spondylitis, polyarteritis nodosa and Wegener's granulomatosis, etc.

As used herein, the term "therapeutically effective amount" or "prophylactically effective amount" refers to an amount sufficient to treat or prevent a disease in a patient but low enough to avoid a serious side effect (at a reasonable benefit/risk ratio) within the scope of sound medical judgment. The therapeutically effective amount of a compound will depend on factors such as the particular compound selected (e.g., the potency, effectiveness and half-life of the compound may be taken into consideration), the route of administration selected, the disease being treated, the severity of the disease being treated, the age, size, body-weight and physical ailment of the patient being treated, the medical history of the patient being treated, the duration of treatment, the nature of concurrent therapy, the desired therapeutic effect, and the like, but can still be routinely determined by those skilled in the art.

In addition, it should be pointed out that the specific dosage and usage of the benzylamine derivative, or a pharmaceutically acceptable stereoisomer, salt, solvate or prodrug thereof for different patients depends on many factors, including the age, body weight, gender, natural health status, nutritional status of the patient, the active strength, administration time, metabolic rate of drug, severity of disease, and the subjective judgment of the treating physician. It is preferred to use a dose between 0.001 and 1000 mg/kg body weight/day.

Beneficial Effects of Invention

The compounds involved in the present invention have strong binding ability to human PD-L1, have the activity of significantly inhibiting the interaction of PD-1/PD-L1, and have significant anti-tumor efficacy in vivo.

BRIEF DESCRIPTION OF THE DRAWINGS

The drawings described herein are used to further elucidate the present invention, and constitute a part of the present application. The exemplary examples of the present invention and their descriptions are used to explain the present invention and do not constitute an improper limitation of the present invention. In the attached drawings.

SPECIFIC MODELS FOR CARRYING OUT THE PRESENT INVENTION

Figure 1:
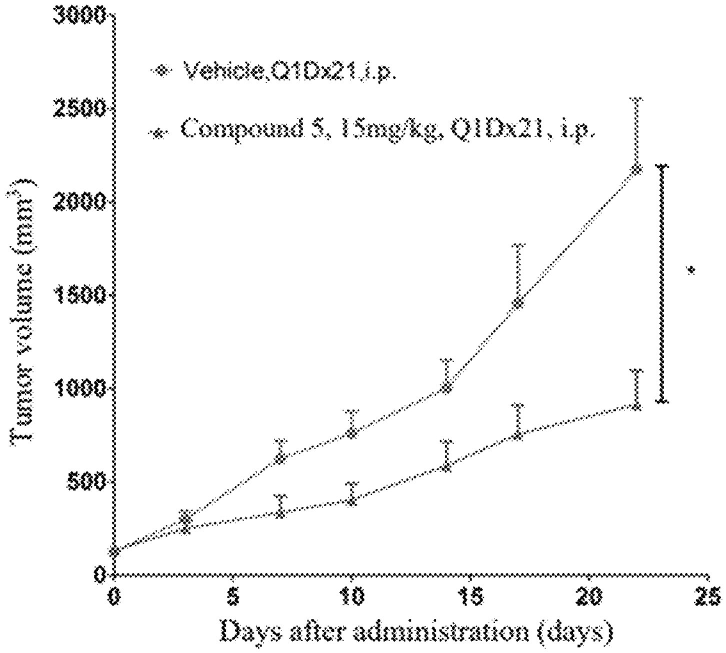
FIG. 1 shows the tumor proliferation curve over time after 15 mg/kg of Compound 5 was administered by intraperitoneal injection to PD-1 humanized mice.

The technical solutions in the examples of the present invention will be clearly and completely described below with reference to the accompanying drawings in the examples of the present invention. Obviously, the described examples are only a part of the examples of the present invention, but not all of the examples. The following description of at least one exemplary examples is merely illustrative in nature and is in no way intended to limit the present invention, its application, or uses in any way. Based on the examples of the present invention, all other examples obtained by those of ordinary skill in the art without creative efforts shall fall within the protection scope of the present invention.

Example 1

(1) Synthesis of Intermediate 1-1

1-1

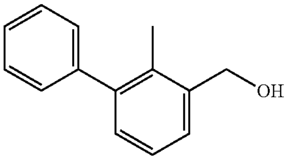

3-Bromo-2-methylbenzyl alcohol (2.51 g, 12.5 mmol), phenylboronic acid (2.29 g, 18.75 mmol), cesium acetate (5.99 g, 31.25 mmol), $PdCl_2$(dppf) (0.917 g, 1.25 mmol) were reacted at reflux in 40 mL of THF under the protection of argon for 23 h, cooled, and concentrated. The residue was added with water and DCM, extracted three times. The organic phase was washed three times with water, concentrated and purified by column chromatography to obtain 2.44 g of a brown solid with a yield of 98%. $^1H$ NMR (400 MHz, $CDCl_3$): δ 7.44-7.32 (m, 4H), 7.32-7.27 (m, 2H), 7.26-7.23 (m, 1H), 7.20 (dd, J=7.6, 1.2 Hz, 1H), 4.77 (s, 2H), 2.24 (s, 3H), 1.70 (s, 1H). ESI-MS: m/z=181.11 $[M-OH]^+$.

(2) Synthesis of Intermediate 1-2

1-2

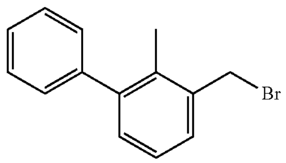

1-1 (1.51 g, 7.62 mmol) was dissolved in 30 mL of DCM, cooled to 0° C. in an ice bath, added dropwise with $PBR_3$ (0.36 mL, 3.81 mmol). After the addition, the resulting mixture was continued to react for 20 min. The reaction was then quenched by adding crushed ice. Extraction was conducted three times with DCM. The organic phase was washed with saturated sodium bicarbonate solution once, and then washed to neutral with water, dried over anhydrous $Na_2SO_4$, suction filtration was conducted, the filtrate was concentrated to dryness to obtain 1.32 g of a colorless oil with a yield of 66%, which was directly used in the next step without purification. $^1H$ NMR (400 MHz, $CDCl_3$): δ 7.44-7.39 (m, 2H), 7.38-7.32 (m, 2H), 7.32-7.27 (m, 2H), 7.22 (d, J=2.8 Hz, 1H), 7.21 (s, 1H), 4.60 (s, 2H), 2.30 (s, 3H). ESI-MS: m/z=181.10 $[M-Br]^+$.

(3) Synthesis of Intermediate 1-3

1-3

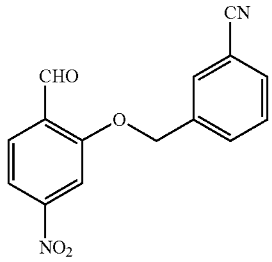

2-Hydroxy-p-nitrobenzaldehyde (4.81 g, 28.78 mmol) was dissolved in 40 mL of DMF, followed by an addition of $K_2CO_3$ (5.97 g, 43.20 mmol), m-cyanobenzyl bromide (6.21 g, 31.68 mmol) and tetrabutylammonium iodide (50 mg, 0.14 mmol), the resulting mixture was reacted at room temperature for 4 h, the reaction solution was poured into 900 mL of ice water, suction filtration was conducted, the filter cake was washed with water to neutral, and then dispersed in cyclohexane after being dried, subjected to sonication and suction filtration, and 8.05 g of a yellow-white powdery solid was obtained with a yield of 99%, which was directly used in the next step without purification. $^1H$ NMR (400 MHz, DMSO-$d_6$): δ 10.49 (s, 1H), 8.09 (t, J=1.6 Hz, 2H), 7.98-7.91 (m, 3H), 7.86 (d, J=7.6 Hz, 1H), 7.66 (t, J=7.8 Hz, 1H), 5.51 (s, 2H).

ESI-MS: m/z=281.06 $[M-H]^-$.

(4) Synthesis of Intermediate 1-4

1-4

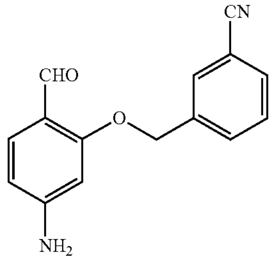

1-3 (8.05 g, 28.52 mmol), Fe powder (5.59 g, 99.82 mmol) and $NH_4Cl$ (2.29 g, 42.81 mmol) were suspended in 100 mL of a mixed solvent of $EtOH/H_2O$=4/1, heated to reflux and reacted for 1.5 h, cooled, subjected to suction filtration to remove insolubles, the filtrate was evaporated to dryness, added with water and subjected to sonication and suction filtration to obtain 6.48 g of an orange powdery solid with a yield of 90%, which was directly used in the next step without purification. $^1H$ NMR (400 MHz, DMSO-$d_6$): δ 10.05 (s, 1H), 8.16-7.34 (m, 5H), 6.60-6.06 (m, 4H), 5.21 (s, 2H). ESI-MS: m/z=253.10 $[M+H]^+$.

(5) Synthesis of Intermediate 1-5

1-5

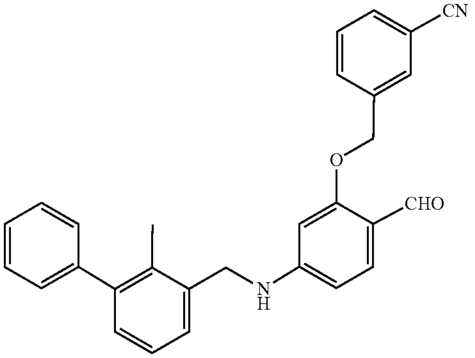

1-2 (490 mg, 1.88 mmol) and 1-4 (567 mg, 2.25 mmol) were suspended in 15 mL of acetonitrile and 2 mL of DMF, added with $K_2CO_3$ (392 mg, 2.84 mmol), reacted at reflux for 11 h, concentrated, added with water, and extracted with EA three times, the organic phase was washed with water to neutral, concentrated, and the residue was purified by column chromatography to obtain 460 mg of a yellow-white solid with a yield of 57%. $^1$H NMR (400 MHz, $CDCl_3$): δ 10.23 (s, 1H), 7.75 (d, J=8.4 Hz, 1H), 7.72-7.66 (m, 2H), 7.66-7.60 (m, 1H), 7.51 (t, J=7.6 Hz, 1H), 7.48-7.40 (m, 2H), 7.40-7.35 (m, 1H), 7.33-7.27 (m, 3H), 7.25-7.21 (m, 2H), 6.32 (dd, J=8.8, 2.0 Hz, 1H), 6.09 (d, J=2.0 Hz, 1H), 5.14 (s, 2H), 4.67 (br, 1H), 4.40 (d, J=4.8 Hz, 2H), 2.23 (s, 3H). ESI-MS: m/z=433.19 [M+H]$^+$.

(6) Synthesis of Compound 1

1

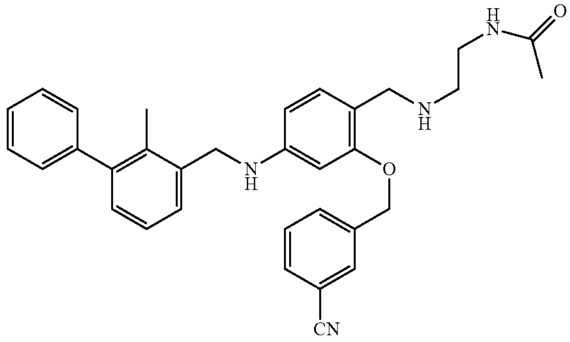

1-5 (100 mg, 0.23 mmol) and N-acetylethylenediamine (47 mg, 0.46 mmol) were dissolved in 2 mL of DCE and 0.5 mL of DMF, added with glacial acetic acid (26 μL, 0.46 mmol), reacted at 35° C. for 24 h, followed by an addition of $NaBH(OAc)_3$ (147 mg, 0.69 mmol), the resulting mixture was continued to react for 14 h, water was added, extracted with DCM for three times, the organic phase was washed with water three times, concentrated, purified by column chromatography and recrystallized to obtain 42 mg of earthy yellow powder with a yield of 35%. $^1$H NMR (400 MHz, DMSO-$d_6$): δ 7.90 (s, 1H), 7.80-7.76 (m, 3H), 7.60 (t, J=7.6 Hz, 1H), 7.45 (t, J=7.6 Hz, 2H), 7.39-7.34 (m, 1H), 7.31-7.28 (m, 3H), 7.19 (t, J=7.6 Hz, 1H), 7.10 (dd, J=7.5, 1.1 Hz, 1H), 6.97 (d, J=8.0 Hz, 1H), 6.35 (d, J=2.0 Hz, 1H), 6.15 (dd, J=8.0, 2.0 Hz, 1H), 6.03 (t, J=5.6 Hz, 1H), 5.10 (s, 2H), 4.23 (d, J=5.6 Hz, 2H), 3.57 (s, 2H), 3.11 (q, J=6.4 Hz, 2H), 2.52-2.50 (m, 2H), 2.18 (s, 3H), 1.81 (br, 1H), 1.76 (s, 3H). ESI-HRMS: m/z calculated for $C_{33}H_{35}N_4O_2^+$ [M+H]$^+$ 519.2755, found 519.2754.

Example 2

2

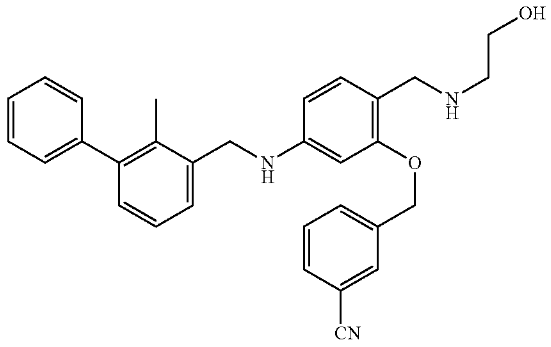

1-5 (108 mg, 0.25 mmol) and ethanolamine (31 mg, 0.5 mmol) were dissolved in 3 mL of DCE, added with glacial acetic acid (29 μL, 0.50 mmol), reacted at room temperature for 12 h, followed by an addition of $NaBH(OAc)_3$ (159 mg, 0.75 mmol), the reaction was continued for 12 h, followed by an addition of water, the resulting mixture was extracted with a mixed solvent of DCM/MeOH=10/1, the organic phase was washed with water, concentrated, purified by column chromatography and recrystallized, 30 mg of earth yellow powder was obtained with a yield of 25%. $^1$H NMR (400 MHz, DMSO-$d_6$): δ 7.90 (s, 1H), 7.79 (d, J=7.6 Hz, 2H), 7.59 (t, J=8.0 Hz, 1H), 7.45 (t, J=7.2 Hz, 2H), 7.38-7.35 (m, 1H), 7.31-7.29 (m, 3H), 7.19 (t, J=7.6 Hz, 1H), 7.10 (d, J=7.2 Hz, 1H), 6.96 (d, J=8.0 Hz, 1H), 6.36 (s, 1H), 6.15 (d, J=7.8 Hz, 1H), 6.03 (t, J=5.6 Hz, 1H), 5.10 (s, 2H), 4.46 (br, 1H), 4.23 (d, J=4.8 Hz, 2H), 3.58 (s, 2H), 3.44 (t, J=5.2 Hz, 2H), 2.53 (t, J=6.0, 2H), 2.18 (s, 3H), 1.90 (br, 1H). ESI-HRMS: m/z calculated for $C_{31}H_{31}N_3NaO_2^+$ [M+Na]$^+$ 500.2308, found 500.2307.

Example 3

3

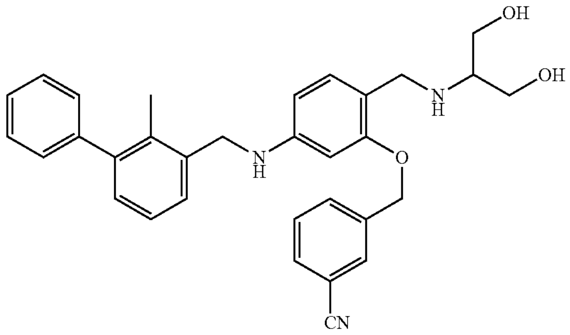

1-5 (108 mg, 0.25 mmol) and 2-aminopropanediol (46 mg, 0.5 mmol) were dissolved in 2 mL of DCE and 0.5 mL of DMF, added with glacial acetic acid (29 μL, 0.50 mmol), reacted at 35° C. for 24 h, followed by an addition of $NaBH(OAc)_3$ (159 mg, 0.75 mmol), the reaction was continued for 24 h, followed by an addition of water, the resulting mixture was extracted with a mixed solvent of DCM/MeOH=10/1, the organic phase was washed with water, concentrated, recrystallized and purified, 92 mg of earth yellow powder was obtained with a yield of 72%. $^1H$ NMR (400 MHz, DMSO-$d_6$): δ 8.31 (br, 2H), 7.99 (s, 1H), 7.88 (d, J=8.0 Hz, 1H), 7.79 (d, J=7.6 Hz, 1H), 7.57 (t, J=8.0 Hz, 1H), 7.47-7.44 (m, 2H), 7.40-7.35 (m, 1H), 7.31 (d, J=1.2 Hz, 1H), 7.29 (s, 1H), 7.26 (d, J=7.6 Hz, 1H), 7.19 (t, J=7.6 Hz, 1H), 7.10 (d, J=7.6 Hz, 1H), 7.07 (d, J=8.4 Hz, 1H), 6.40-6.35 (m, 2H), 6.19 (dd, J=8.0, 1.6 Hz, 1H), 5.41 (br, 1H), 5.18-5.11 (m, 2H), 4.25 (d, J=5.2 Hz, 2H), 4.04 (dd, J=43.6, 12.8 Hz, 2H), 3.78 (dd, J=11.6, 4.0 Hz, 1H), 3.66 (dd, J=11.2, 7.2 Hz, 1H), 3.19-3.16 (m, 1H), 2.17 (s, 3H). ESI-HRMS: m/z calculated for $C_{32}H_{31}N_3NaO_4^+$ [M+Na]$^+$ 544.2207, found 544.2208.

Example 4

4

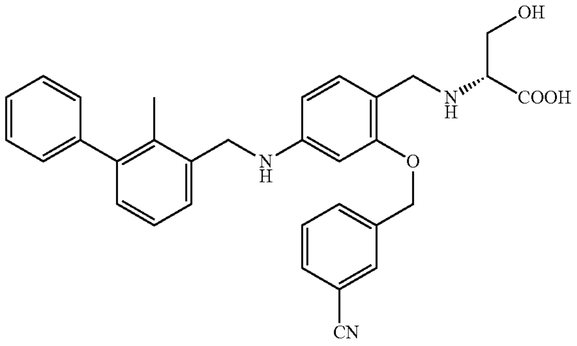

1-5 (216 mg, 0.50 mmol) an D-serine (105 mg, 1.0 mmol) were suspended in 2 mL of DMF, and glacial acetic acid (57 μL, 1.0 mmol) was added, reacted at 35° C. for 24 h, followed by an addition of $NaBH(OAc)_3$ (318 mg, 1.50 mmol), the reaction was continued for 24 h, followed by an addition of water, the resulting mixture was extracted with a mixed solvent of DCM/MeOH=10/1, the organic phase was washed with water, concentrated, and the residue was purified by preparative liquid phase chromatography to obtain 180 mg of yellow-white powder with a yield of 69%. 1H NMR (400 MHz, DMSO-$d_6$): δ 8.31 (br, 2H), 7.99 (s, 1H), 7.88 (d, J=8.0 Hz, 1H), 7.79 (d, J=7.6 Hz, 1H), 7.57 (t, J=8.0 Hz, 1H), 7.47-7.44 (m, 2H), 7.40-7.35 (m, 1H), 7.31 (d, J=1.2 Hz, 1H), 7.29 (s, 1H), 7.26 (d, J=7.6 Hz, 1H), 7.19 (t, J=7.6 Hz, 1H), 7.10 (d, J=7.6 Hz, 1H), 7.07 (d, J=8.4 Hz, 1H), 6.40-6.35 (m, 2H), 6.19 (dd, J=8.0, 1.6 Hz, 1H), 5.41 (br, 1H), 5.18-5.11 (m, 2H), 4.25 (d, J=5.2 Hz, 2H), 4.04 (dd, J=43.6, 12.8 Hz, 2H), 3.78 (dd, J=11.6, 4.0 Hz, 1H), 3.66 (dd, J=11.2, 7.2 Hz, 1H), 3.19-3.16 (m, 1H), 2.17 (s, 3H). ESI-HRMS: m/z calculated for $C_{32}H_{31}N_3NaO_4^+$ [M+Na]$^+$ 544.2207, found 544.2208.

Example 5

(1) Synthesis of Intermediate 5-1

5-1

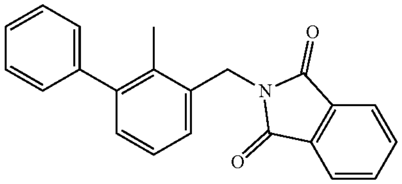

1-1 (7.36 g, 37.14 mmol), phthalimide (6.56 g, 44.57 mmol) and $PPh_3$ (13.64 g, 52.00 mmol) were added in a three-necked flask; under the protection of Ar, 170 mL of anhydrous THF was added, cooled to 0° C., added dropwise with DEAD (9.06 g, 52.00 mmol), after the addition, the reaction was carried out at room temperature for 24 h. The solvent was evaporated to dryness, the residue was purified by column chromatography to obtain 11.21 g of white solid with a yield of 92%. $^1H$ NMR (400 MHz, $CDCl_3$): δ 7.92-7.86 (m, 2H), 7.77-7.72 (m, 2H), 7.43-7.38 (m, 2H), 7.36-7.31 (m, 1H), 7.30-7.26 (m, 2H), 7.24-7.21 (m, 1H), 7.20-7.12 (m, 2H), 4.94 (s, 2H), 2.34 (s, 3H). ESI-MS: m/z=328.13 [M+H]$^+$.

(2) Synthesis of Intermediate 5-2

5-2

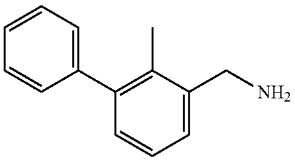

5-1 (11.21 g, 34.27 mmol) was dissolved in 210 mL of ethanol, added with 85% hydrazine hydrate (3.63 g, 61.68 mmol), reacted at reflux for 3 h, cooled, and then added with 40 mL of 6N HCl aqueous solution, reflux was continued for 30 min, the reaction system was cooled to 0° C., suction filtration was conducted to remove insolubles, the filtrate was concentrated, adjusted with saturated $NaHCO_3$ to pH=8-9, extracted with DCM, the organic phase was washed once with water, the solvent was evaporated to dryness to obtain 6.5 g of a colorless oil with a yield of 96%, which was used directly without purification in the next step. $^1H$ NMR (400 MHz, $CDCl_3$): δ 7.43-7.37 (m, 2H), 7.36-7.31 (m, 2H), 7.30-7.27 (m, 2H), 7.24 (t, J=7.6 Hz, 1H), 7.15 (dd, J=7.6, 1.2 Hz, 1H), 3.93 (s, 2H), 2.22 (s, 3H), 1.79 (s, 2H). ESI-MS: m/z=198.13 [M+H]$^+$.

(3) Synthesis of Intermediate 5-3

5-3

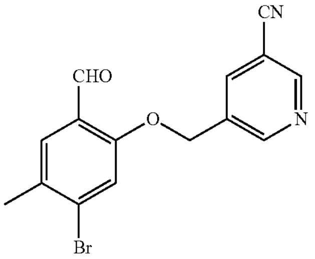

4-Bromo-2-hydroxy-5-methylbenzaldehyde (430 mg, 2 mmol) was dissolved in 6 mL of acetonitrile, added with $K_2CO_3$ (304 mg, 2.2 mmol), 5-chloromethylnicotinonitrile (336 mg, 2.2 mmol) and NaI (30 mg, 0.2 mmol), reacted at room temperature for 24 h, diluted by adding 18 mL of water, suction filtration was conducted to remove insolubles, washed with water to neutral, to obtain 649 mg of earth yellow powdery solid with a yield of 98%, which was directly used in the next step without purification. $^1$H NMR (400 MHz, DMSO-$d_6$): δ 10.37 (s, 1H), 9.03 (d, J=1.6 Hz, 1H), 9.01 (d, J=2.0 Hz, 1H), 8.53 (s, 1H), 7.68 (s, 1H), 7.63 (s, 1H), 5.40 (s, 2H), 2.34 (s, 3H). ESI-MS: m/z=331.01 $[M+H]^+$.

(4) Synthesis of Intermediate 5-4

5-4

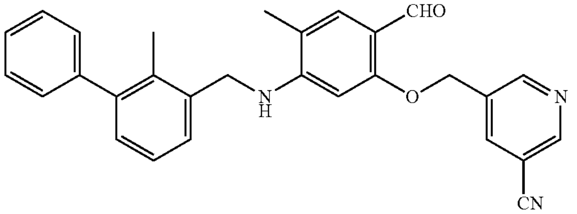

5-2 (296 mg, 1.5 mmol), 5-3 (596 mg, 1.8 mmol), $Cs_2CO_3$ (733 mg, 2.25 mmol), BINAP (187 mg, 0.3 mmol) and $Pd(OAc)_2$ (34 mg, 0.15 mmol) were suspended in 15 mL of dioxane, refluxed under Ar protection for 20 h, concentrated, added with water, extracted with DCM, the organic phase was washed with water to neutral, and purified by column chromatography to obtain 300 mg of a yellow-white solid with a yield of 45%. $^1$H NMR (400 MHz, $CDCl_3$): δ 10.21 (s, 1H), 8.84 (t, J=1.8 Hz, 2H), 8.05 (t, J=2.0 Hz, 1H), 7.61 (s, 1H), 7.46-7.42 (m, 2H), 7.39-7.35 (m, 1H), 7.33-7.30 (m, 2H), 7.27-7.24 (m, 3H), 6.08 (s, 1H), 5.18 (s, 2H), 4.50 (br, 1H), 4.44 (s, 2H), 2.25 (s, 3H), 2.13 (s, 3H). ESI-MS: m/z=448.21 $[M+H]^+$.

(5) Synthesis of Compound 5

5

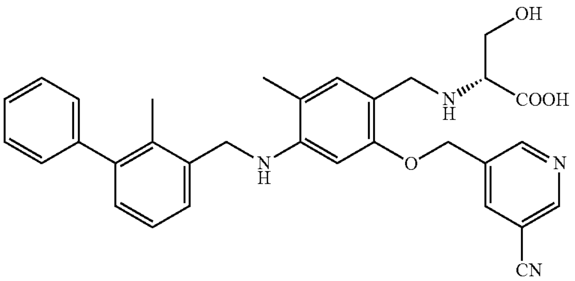

5-4 (750 mg, 1.68 mmol) and D-serine (350 mg, 3.36 mmol) were suspended in 12 mL of anhydrous DMF and 4 mL of anhydrous methanol, then added with glacial acetic acid (195 μL, 3.36 mmol), and the reaction was carried out at 35° C. for 24 h, followed by an addition of $NaBH(OAc)_3$ (1.065 g, 5.04 mmol), the reaction was continued for 24 h, followed by an addition of water, the resulting mixture was extracted with a mixed solvent of DCM/MeOH (10:1), the organic phase was washed with water, concentrated to dryness, the residue was purified by preparative liquid phase chromatography to obtain 350 mg of white powdery solid with a yield of 39%. $^1$H NMR (400 MHz, DMSO-$d_6$): δ 8.88 (dd, J=15.6, 2.0 Hz, 2H), 8.37 (t, J=2.0 Hz, 1H), 8.34 (br, 2H), 7.48-7.44 (m, 2H), 7.40-7.35 (m, 1H), 7.35-7.34 (m, 1H), 7.33-7.32 (m, 1H), 7.16 (dd, J=7.6, 1.8 Hz, 1H), 7.12 (t, J=7.2 Hz, 1H), 7.07 (dd, J=7.2, 1.8 Hz, 1H), 7.01 (s, 1H), 6.09 (s, 1H), 5.72 (t, J=5.6 Hz, 1H), 5.38 (br, 1H), 5.14 (dd, J=18.8, 13.2 Hz, 2H), 4.35 (d, J=5.6 Hz, 2H), 4.04 (dd, J=44.8, 12.8 Hz, 2H), 3.78 (dd, J=11.2, 4.4 Hz, 1H), 3.64 (dd, J=11.4, 7.2 Hz, 1H), 3.19-3.16 (m, 1H), 2.19 (s, 3H), 2.10 (s, 3H). ESI-HRMS: m/z calculated for $C_{32}H_{32}N_4NaO_4^+$ $[M+Na]^+$ 559.2316, found 559.2313.

Example 6

(1) Synthesis of Intermediate 6-1

6-1

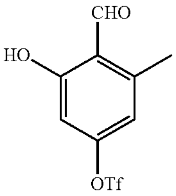

2,4-Dihydroxy-6-methylbenzaldehyde (1.52 g, 10 mmol) was dissolved in 40 mL of DCM, 2,6-dimethylpyridine (1.13 g, 10.5 mmol) and DMAP (245 mg, 2 mmol) were added, cooled to 0° C., added dropwise with 15 mL of $Tf_2O$ (2.96 g, 10.5 mmol) in DCM solution, the reaction was carried out at room temperature for 10 h after the addition, followed by an addition of water, the resulting mixture was extracted with DCM, the organic phase was washed with water, the solvent was evaporated to dryness, and the residue was purified by column chromatography to obtain 1.7 g of a colorless oily substance with a yield of 60%. $^1$H NMR (400

MHz, $CDCl_3$): δ 12.16 (s, 1H), 10.31 (s, 1H), 6.76 (d, J=2.4 Hz, 1H), 6.67 (d, J=2.4 Hz, 1H), 2.67 (s, 3H). ESI-MS: m/z=285.00 $[M+H]^+$.

(2) Synthesis of Intermediate 6-2

6-2

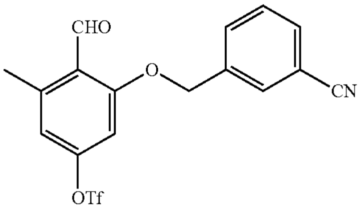

6-1 (220 mg, 0.77 mmol) was dissolved in 8 mL of acetonitrile, added with $K_2CO_3$ (128 mg, 0.92 mmol), m-cyanobenzyl bromide (159 mg, 0.81 mmol) and tetrabutylammonium iodide (15 mg, 0.04 mmol), the resulting mixture was reacted at room temperature for 6 h, concentrated, then added with water, extracted with DCM, the organic phase was washed with water to neutral, the organic phase was concentrated, and purified by column chromatography to obtain 286 mg of a yellow-white solid with a yield of 93%. $^1H$ NMR (400 MHz, $CDCl_3$): δ 10.64 (s, 1H), 7.78-7.61 (m, 3H), 7.60-7.52 (m, 1H), 6.80 (s, 2H), 5.20 (s, 2H), 2.63 (s, 3H), (Isomer ratio=5:1). ESI-MS: m/z=400.03 $[M+H]^+$.

(3) Synthesis of Intermediate 6-3

6-3

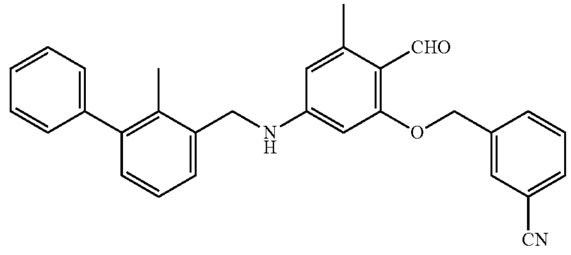

5-2 (99 mg, 0.5 mmol), 6-2 (200 mg, 0.5 mmol), $Cs_2CO_3$ (244 mg, 0.75 mmol), BINAP (62 mg, 0.1 mmol) and $Pd(OAc)_2$ (11 mg, 0.05 mmol) were suspended in 5 mL of dioxane, reacted at reflux under Ar protection for 24 h, concentrated, added with water, extracted with DCM, the organic phase was washed with water to neutral, and purified by column chromatography to obtain 131 mg of a yellow-white solid with a yield of 59%. $^1H$ NMR (400 MHz, $CDCl_3$): δ 10.46 (s, 1H), 7.69-7.64 (m, 2H), 7.63-7.59 (m, 1H), 7.53-7.46 (m, 1H), 7.46-7.40 (m, 2H), 7.39-7.34 (m, 1H), 7.32-7.27 (m, 3H), 7.24 (d, J=2.0 Hz, 1H), 7.23 (s, 1H), 6.10 (s, 1H), 5.99 (d, J=2.0 Hz, 1H), 5.11 (s, 2H), 4.53 (br, 1H), 4.38 (d, J=3.2 Hz, 2H), 2.57 (s, 3H), 2.23 (s, 3H). ESI-MS: m/z=447.17 $[M+H]^+$.

(4) Synthesis of Compound 6

6

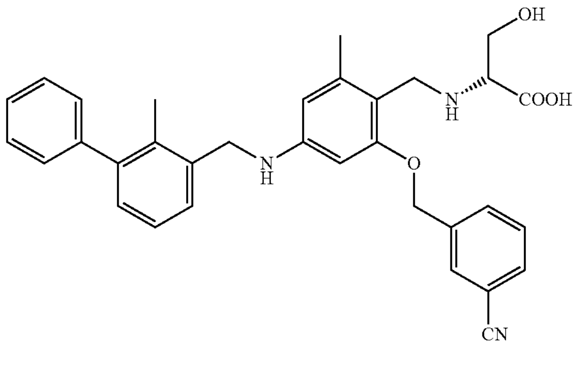

6-3 (131 mg, 0.29 mmol) and D-serine (62 mg, 0.58 mmol) were suspended in 4 mL of anhydrous DMF and 1 mL of DCE, then added with glacial acetic acid (34 μL, 0.58 mmol), reacted at 35° C. for 24 h, followed by an addition of $NaBH(OAc)_3$ (187 mg, 0.87 mmol), the reaction was continued for 24 h, followed by an addition of water, extracted with a mixed solvent of DCM/MeOH (10:1), washed with water, concentrated to dryness, the residue was purified by preparative liquid phase chromatography to obtain 48 mg of a white powdery solid with a yield of 31%. $^1H$ NMR (400 MHz, DMSO-$d_6$): δ 8.20 (br, 2H), 7.98 (s, 1H), 7.88 (d, J=8.0 Hz, 1H), 7.78 (d, J=7.8 Hz, 1H), 7.56 (dt, J=7.6, 1.2 Hz, 1H), 7.49-7.41 (m, 2H), 7.40-7.34 (m, 1H), 7.32-7.28 (m, 2H), 7.27-7.23 (m, 1H), 7.18 (t, J=7.6 Hz, 1H), 7.10 (dd, J=7.6, 1.2 Hz, 1H), 6.29 (t, J=5.2 Hz, 1H), 6.24 (d, J=1.6 Hz, 1H), 6.12 (d, J=1.6 Hz, 1H), 5.37 (br, 1H), 5.13 (dd, J=14.8, 13.2 Hz, 2H), 4.24 (d, J=5.6 Hz, 2H), 4.10 (s, 2H), 3.84 (dd, J=11.6, 4.4 Hz, 1H), 3.61 (dd, J=11.6, 8.4 Hz, 1H), 3.19 (dd, J=8.0, 4.4 Hz, 1H), 2.21 (s, 3H), 2.17 (s, 3H). ESI-HRMS: m/z calculated for $C_{33}H_{33}N_3NaO_4^+$ $[M+Na]^+$ 558.2363, found 558.2363.

Example 7

(1) Synthesis of Intermediate 7-1

7-1

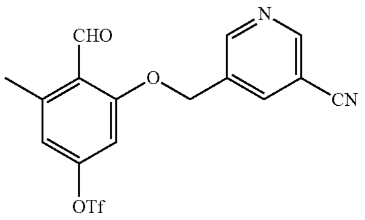

6-1 (852 mg, 3 mmol) was dissolved in 24 mL of acetonitrile, added with $K_2CO_3$ (954 mg, 6.90 mmol), 5-chloromethylnicotinonitrile hydrochloride (624 mg, 3.30 mmol) and NaI (45 mg, 0.3 mmol), reacted at room temperature for 12 hours, then reacted at 45° C. for 9 hours, concentrated, added with water, extracted with EA, the organic phase was washed with water to neutral, and the organic phase was concentrated and purified by column chromatography to obtain 780 mg of a yellow-white solid with a yield of 65%. $^1$H NMR (400 MHz, $CDCl_3$): δ 10.61 (s, 1H), 8.93 (s, 2H), 8.10 (s, 1H), 6.85 (s, 2H), 5.25 (s, 2H), 2.64 (s, 3H). ESI-MS: m/z=401.03 $[M+H]^+$.

(2) Synthesis of Intermediate 7-2

7-2

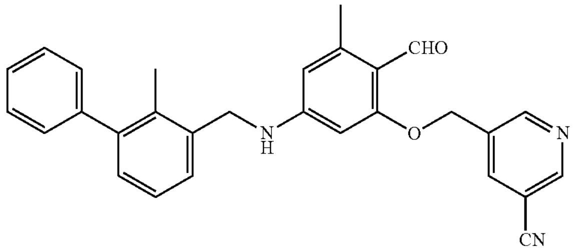

5-2 (311 mg, 1.58 mmol), 7-1 (760 mg, 1.89 mmol), $Cs_2CO_3$ (772 mg, 2.37 mmol), BINAP (197 mg, 0.32 mmol) and $Pd(OAc)_2$ (36 mg, 0.16 mmol) were suspended in 15 mL of dioxane, reacted at 85° C. under the protection of Ar for 20 h, concentrated, added with water, extracted with DCM, the organic phase was washed with water to neutral, and purified by column chromatography to obtain 305 mg of a yellow-white solid with a yield of 43%. $^1$H NMR (400 MHz, DMSO-$d_6$): δ 10.27 (s, 1H), 9.00 (d, J=2.0 Hz, 1H), 8.96 (d, J=2.0 Hz, 1H), 8.45 (t, J=2.0 Hz, 1H), 7.49-7.42 (m, 2H), 7.42-7.34 (m, 1H), 7.34-7.29 (m, 2H), 7.29-7.18 (m, 3H), 7.14 (dd, J=7.4, 1.4 Hz, 1H), 6.27 (s, 1H), 6.16 (s, 1H), 5.26 (s, 2H), 4.39 (d, J=5.2 Hz, 2H), 2.41 (s, 3H), 2.19 (s, 3H). ESI-MS: m/z=448.20 $[M+H]^+$.

(3) Synthesis of Compound 7

7

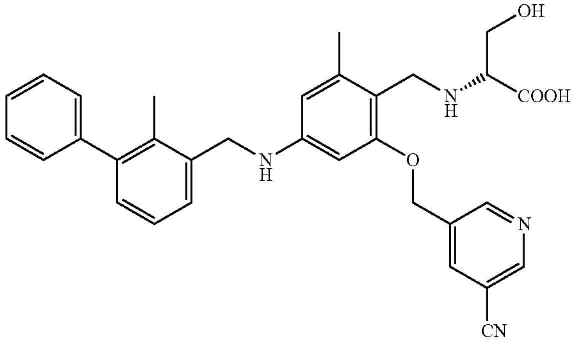

7-2 (269 mg, 0.60 mmol) and D-serine (126 mg, 1.20 mmol) were suspended in 8 mL of anhydrous DMF and 2 mL of DCE, and then added with glacial acetic acid (70 μL, 1.20 mmol), reacted at 35° C. for 24 h, followed by an addition of $NaBH(OAc)_3$ (382 mg, 1.80 mmol), the reaction was continued for 24 h, followed by an addition of water, the resulting mixture was extracted with a mixed solvent of DCM/MeOH (10:1), the organic phase was washed with water, concentrated to dryness, the residue was purified by preparative liquid phase chromatography to obtain 119 mg of a white powdery solid with a yield of 37%. $^1$H NMR (400 MHz, DMSO-$d_6$): δ 9.02 (d, J=2.4 Hz, 1H), 8.99 (d, J=2.0 Hz, 1H), 8.49 (t, J=2.4 Hz, 1H), 8.17 (br, 2H), 7.48-7.42 (m, 2H), 7.41-7.34 (m, 1H), 7.34-7.28 (m, 2H), 7.26 (d, J=7.6 Hz, 1H), 7.19 (t, J=7.6 Hz, 1H), 7.10 (dd, J=7.6, 1.6 Hz, 1H), 6.31 (t, J=5.6 Hz, 1H), 6.25 (d, J=1.6 Hz, 1H), 6.14 (d, J=1.6 Hz, 1H), 5.38 (br, 1H), 5.18 (dd, J=18.0, 13.2 Hz, 2H), 4.25 (d, J=5.2 Hz, 2H), 4.10 (s, 2H), 3.82 (dd, J=11.6, 4.4 Hz, 1H), 3.61 (dd, J=11.2, 8.4 Hz, 1H), 3.19 (dd, J=8.0, 4.4 Hz, 1H), 2.22 (s, 3H), 2.17 (s, 3H). ESI-HRMS: m/z calculated for $C_{32}H_{32}N_4NaO_4^+$ $[M+Na]^+$ 559.2316, found 559.2317.

Example 8

(1) Synthesis of Intermediate 8-1

8-1

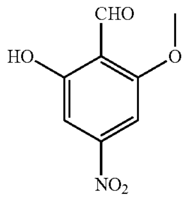

2-Methoxy-4-nitrobenzaldehyde (2.05 g, 11.32 mmol), 2-amino-4-chlorobenzoic acid (0.97 g, 5.66 mmol), 1-fluoro-2,4,6-trismethylpyridine trifluoromethanesulfonate (4.91 g, 16.98 mmol), $Pd(OAc)_2$ (249 mg, 1.11 mmol) and p-toluenesulfonic acid (3.89 g, 22.59 mmol) were suspended in 80 mL of glacial acetic acid, stirred at room temperature for 10 min, the reaction system was continued to react at 90° C. for 24 h, cooled and concentrated, the residue was purified by column chromatography to obtain 1.50 g of a pale yellow solid with a yield of 67%. $^1$H NMR (400 MHz, $CDCl_3$): δ 12.06 (s, 1H), 10.41 (s, 1H), 7.39 (dd, J=2.0, 0.8 Hz, 1H), 7.23 (d, J=2.0 Hz, 1H), 4.03 (s, 3H). ESI-MS: m/z=198.05 $[M+H]^+$.

(2) Synthesis of Intermediate 8-2

8-2

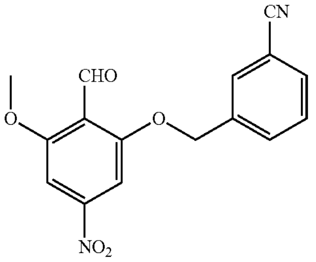

8-1 (684 mg, 3.47 mmol) was dissolved in 12 mL of DMF, added in sequence with $K_2CO_3$ (574 mg, 4.15 mmol), m-cyanobenzyl bromide (715 mg, 3.65 mmol), tetrabutylammonium iodide (15 mg, 0.04 mmol), reacted at room temperature for 7 h, the reaction solution was poured into 300 mL of ice water, subjected to suction filtration, the filter cake was washed with water to neutral, the filter cake was dried and then dispersed in cyclohexane, subjected to sonication and suction filtration to obtain 1 g of a yellow-white powder with a yield of 93%, which was directly used in the next step without purification. $^1$H NMR (400 MHz, DMSO- $d_6$): δ 10.42 (s, 1H), 8.00 (s, 1H), 7.91-7.80 (m, 2H), 7.66-7.57 (m, 3H), 5.42 (s, 2H), 3.99 (s, 3H).

(3) Synthesis of Intermediate 8-3

8-3

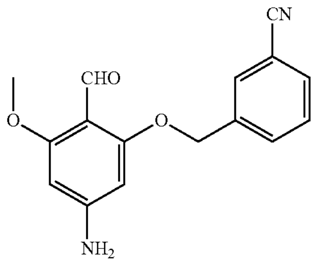

8-2 (900 mg, 2.88 mmol) was suspended in 30 mL of a mixed solution of EtOH/$H_2O$=5/1, added with Fe (565 mg, 10.09 mmol) and $NH_4Cl$ (230 mg, 4.30 mmol), reacted at reflux for 3.5 h, suction filtration was conducted to remove insolubles, the filtrate was evaporated to dryness, and purified by column chromatography to obtain 790 mg of an orange-red powdery solid with a yield of 97%. $^1$H NMR (400 MHz, DMSO-$d_6$): δ 10.09 (s, 1H), 8.03 (s, 1H), 7.88-7.83 (m, 1H), 7.80 (dt, J=8.0, 1.4 Hz, 1H), 7.62 (t, J=7.8 Hz, 1H), 6.39 (s, 2H), 5.87 (dd, J=9.0, 1.4 Hz, 2H), 5.13 (s, 2H), 3.74 (s, 3H). ESI-MS: m/z=283.11 $[M+H]^+$.

(4) Synthesis of Intermediate 8-4

8-4

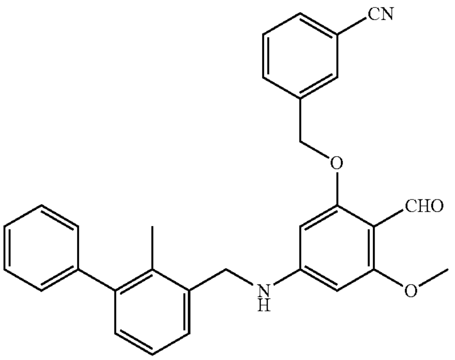

1-2 (290 mg, 1.11 mmol) was dissolved in 5 mL of DMF, added with $K_2CO_3$ (184 mg, 1.33 mmol) and 8-3 (330 mg, 1.17 mmol), reacted under microwave at 85° C. for 35 min, added with water, extracted with DCM, the organic phase was washed with water to neutral, concentrated, and the residue was purified by column chromatography to obtain 150 mg of a yellow-white solid with a yield of 29%. $^1$H NMR (400 MHz, $CDCl_3$): δ 10.32 (s, 1H), 7.78 (d, J=7.8 Hz, 1H), 7.70 (s, 1H), 7.59 (dt, J=7.6, 1.4 Hz, 1H), 7.48 (t, J=7.8 Hz, 1H), 7.45-7.40 (m, 2H), 7.40-7.34 (m, 1H), 7.32-7.27 (m, 3H), 7.24 (d, J=2.0 Hz, 1H), 7.23 (s, 1H), 5.78 (dd, J=18.2, 1.8 Hz, 2H), 5.11 (s, 2H), 4.69 (br, 1H), 4.39 (s, 2H), 3.85 (s, 3H), 2.24 (s, 3H). ESI-MS: m/z=463.19 $[M+H]^+$.

(5) Synthesis of Compound 8

8

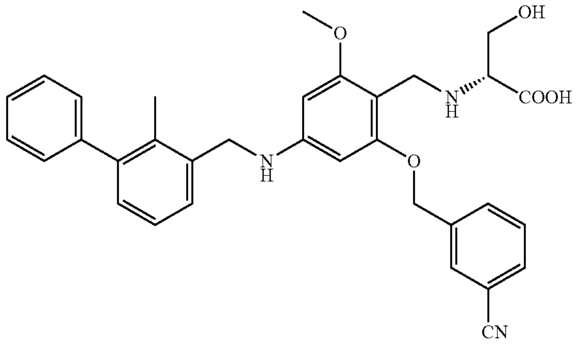

8-4 (189 mg, 0.41 mmol) and D-serine (86 mg, 0.82 mmol) were suspended in 4 mL of anhydrous DMF, then added with glacial acetic acid (47 μL, 0.82 mmol), reacted at 35° C. for 24 hours, followed by an addition of NaBH$(OAc)_3$ (260 mg, 1.23 mmol), the reaction was continued for 24 h, followed by an addition of water, the resulting mixture was extracted with a mixed solvent of DCM/MeOH (10:1), the organic phase was washed with water, concentrated to dryness, and the residue was purified by preparative liquid phase chromatography to obtain 136 mg of a white powdery solid with a yield of 60%. $^1$H NMR (400 MHz, DMSO-$d_6$): δ 8.16 (br, 2H), 7.95 (s, 1H), 7.84 (d, J=8.0 Hz, 1H), 7.78 (d, J=8.0 Hz, 1H), 7.56 (t, J=7.8 Hz, 1H), 7.48-7.43 (m, 2H), 7.40-7.34 (m, 1H), 7.31-7.28 (m, 3H), 7.20 (t, J=7.6 Hz, 1H), 7.12 (dd, J=7.2, 1.2 Hz, 1H), 6.42 (t, J=5.2 Hz, 1H), 6.02 (d, J=3.2 Hz, 2H), 5.31 (br, 1H), 5.13 (dd, J=16.4, 13.2 Hz, 2H), 4.28 (d, J=5.2 Hz, 2H), 4.09 (dd, J=26.8, 13.2 Hz, 2H), 3.78 (dd, J=11.2, 4.4 Hz, 1H), 3.73 (s, 3H), 3.62 (dd, J=11.6, 7.6 Hz, 1H), 3.12 (dd, J=7.2, 4.4 Hz, 1H), 2.19 (s, 3H). ESI-HRMS: m/z calculated for $C_{33}H_{33}N_3NaO_5^+$ $[M+Na]^+$ 574.2312, found 574.2313.

Example 9

(1) Synthesis of Intermediate 9-1

9-1

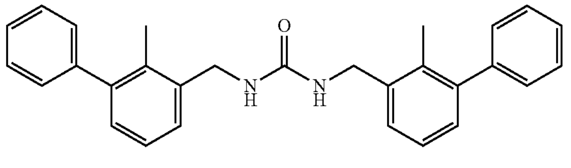

5-2 (1 g, 5.07 mmol) was dissolved in 30 mL of DCM, added with DABCO (57 mg, 0.51 mmol), then added with $Boc_2O$ (553 mg, 2.54 mmol), reacted at room temperature overnight, added with 30 mL of n-hexane, suction filtration was conducted, the filter cake was washed with a mixed solvent of n-hexane: DCM=1:1 to obtain 660 mg of a white powdery solid with a yield of 62%. $^1$H NMR (400 MHz, DMSO-$d_6$): δ 7.46-7.34 (m, 2H) (dd, J=10.0, 4.6 Hz, 1H), 7.40-7.34 (m, 1H), 7.31-7.26 (m, 3H), 7.23 (t, J=7.4 Hz, 1H), 7.09 (dd, J=7.2, 1.6 Hz, 1H), 6.39 (t, J=5.8 Hz, 1H), 4.29 (d, J=6.0 Hz, 2H), 2.14 (s, 3H). ESI-MS: m/z=421.21 $[M+H]^+$.

(2) Synthesis of Intermediate 9-2

9-2

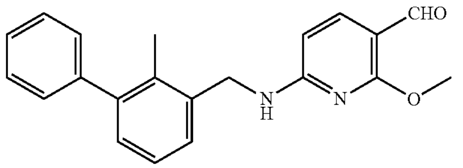

9-1 (907 mg, 2.16 mmol), 6-chloro-2-methoxy-pyridine-3-carbaldehyde (814 mg, 4.75 mmol), $Cs_2CO_3$ (2.10 g, 6.48 mmol), Sphos (266 mg, 0.65 mmol) and $Pd(OAc)_2$ (73 mg, 0.33 mmol) were suspended in 25 mL of dioxane, reacted at reflux under Ar protection for 24 h, concentrated, added with water, extracted with DCM, the organic phase was washed with water to neutral, suction filtration was conducted to remove insolubles, the filtrate was concentrated and purified by column chromatography and preparative silica gel plate to obtain 364 mg of a pale yellow solid with a yield of 25%. $^1$H NMR (400 MHz, $CDCl_3$): δ 10.07 (s, 1H), 7.90 (d, J=8.4 Hz, 1H), 7.45-7.39 (m, 2H), 7.38-7.33 (m, 1H), 7.33-7.27 (m, 3H), 7.25-7.19 (m, 2H), 6.05 (d, J=8.4 Hz, 1H), 5.32 (br, 1H), 4.65 (s, 2H), 3.98 (s, 3H), 2.24 (s, 3H). ESI-MS: m/z=333.14 $[M+H]^+$.

(3) Synthesis of Compound 9

9

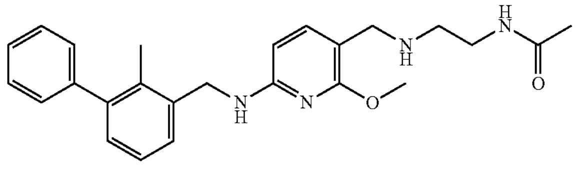

9-2 (157 mg, 0.47 mmol) and N-acetylethylenediamine (97 mg, 0.94 mmol) were dissolved in 4 mL of DCE and 1 mL of DMF, added with glacial acetic acid (54 μL, 0.94 mmol), reacted at 35° C. for 24 h, followed by an addition of $NaBH(OAc)_3$ (300 mg, 1.41 mmol), the reaction was continued for 12 h, followed by an addition of water, the resulting mixture was extracted with a mixed solvent of DCM/MeOH (10:1), washed with water, concentrated to dryness, the residue was purified by preparative liquid phase chromatography to obtain 85 mg of a yellow-white solid with a yield of 43%. $^{11}$H NMR (400 MHz, $CDCl_3$): δ 7.72 (s, 1H), 7.47-7.39 (m, 3H), 7.39-7.32 (m, 1H), 7.32-7.27 (m, 3H), 7.24-7.16 (m, 2H), 6.54 (br, 1H), 5.94 (d, J=8.0 Hz, 1H), 4.79 (t, J=5.2 Hz, 1H), 4.46 (d, J=5.2 Hz, 2H), 3.93 (s, 3H), 3.88 (s, 2H), 3.54-3.47 (m, 2H), 2.95 (t, J=4.8 Hz, 2H), 2.22 (s, 3H), 2.02 (s, 3H). ESI-HRMS: m/z calculated for $C_{25}H_{30}N_4NaO_2^+$ $[M+Na]^+$441.2261, found 441.2259.

Example 10

(1) Synthesis of Intermediate 10-1

10-1

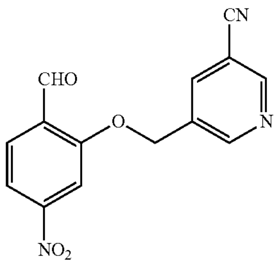

2-Hydroxy-p-nitrobenzaldehyde (2.47 g, 14.78 mmol) was dissolved in 30 mL of DMF, added with $K_2CO_3$ (2.15 g, 15.56 mmol), stirred at room temperature for 30 min, followed by an addition of 5-chloromethylnicotinonitrile (2.48 g, 16.29 mmol) and NaI (222 mg, 1.48 mmol), reacted at room temperature for 19 h, the reaction solution was poured into 1 L of water, subjected to suction filtration, the filter cake was filtrated with water to neutral, the filter cake was dried to obtain 4.05 g of a yellow-white powdery solid with a yield of 97%, which was directly used in the next step without purification. $^1$H NMR (400 MHz, DMSO-$d_6$): δ 10.50 (s, 1H), 9.06 (d, J=2.0 Hz, 1H), 9.05 (d, J=2.0 Hz, 1H), 8.59 (t, J=2.0 Hz, 1H), 8.12 (d, J=1.2 Hz, 1H), 8.00-7.93 (m, 2H), 5.57 (s, 2H). ESI-MS: m/z=284.07 $[M+H]^+$.

(2) Synthesis of Intermediate 10-2

10-2

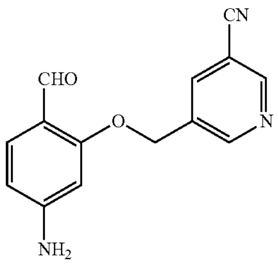

10-1 (4.75 g, 16.77 mmol) was suspended in 185 mL of a mixed solution EtOH/$H_2O$=5/1, added with Fe (3.29 g, 58.75 mmol) and $NH_4Cl$ (1.36 g, 25.43 mmol), reacted at reflux for 1.5 h, suction filtration was conducted to remove insolubles, the filtrate was evaporated to dryness, water was then added, the mixture was subjected to sonication and suction filtration to obtain 4.12 g of an orange-yellow powdery solid with a yield of 97%. $^1$H NMR (400 MHz, DMSO-$d_6$): δ 10.02 (s, 1H), 9.02 (s, 1H), 9.00 (s, 1H), 8.49 (s, 1H), 7.46 (d, J=8.4 Hz, 1H), 6.43 (s, 2H), 6.26 (s, 2H), 5.24 (s, 2H). ESI-MS: m/z=252.09 $[M-H]^-$.

(3) Synthesis of Intermediate 10-3

10-3

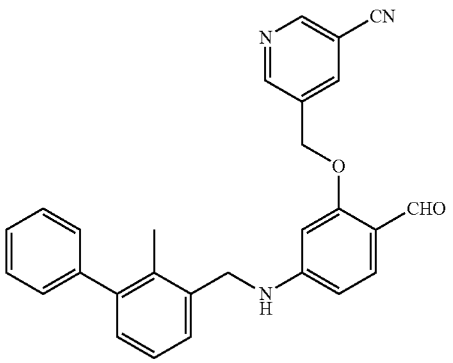

1-2 (2.48 g, 9.50 mmol) and 10-2 (2.52 g, 9.95 mmol) were dissolved in a mixed solution of 51 mL of MeCN and 17 mL of DMF, then added with $K_2CO_3$ (1.58 g, 11.4 mmol), and reacted at 60° C. for 10 h, concentrated, added with water, extracted with EA, the organic phase was washed with water to neutral, and purified by column chromatography to obtain 1 g of a yellow-white solid with a yield of 24%. $^1H$ NMR (400 MHz, DMSO-$d_6$): δ 10.06 (s, 1H), 9.00 (d, J=2.0 Hz, 1H), 8.98 (d, J=2.0 Hz, 1H), 8.48 (t, J=2.0 Hz, 1H), 7.51 (d, J=8.8 Hz, 1H), 7.49-7.43 (m, 2H), 7.40-7.35 (m, 2H), 7.33-7.30 (m, 2H), 7.28 (dd, J=7.6, 1.2 Hz, 1H), 7.23 (t, J=7.6 Hz, 1H), 7.14 (dd, J=7.4, 1.4 Hz, 1H), 6.38 (s, 1H), 6.37 (s, 1H), 5.29 (s, 2H), 4.41 (d, J=5.2 Hz, 2H), 2.20 (s, 3H). ESI-MS: m/z=434.19 $[M+H]^+$.

(4) Synthesis of Compound 10

10

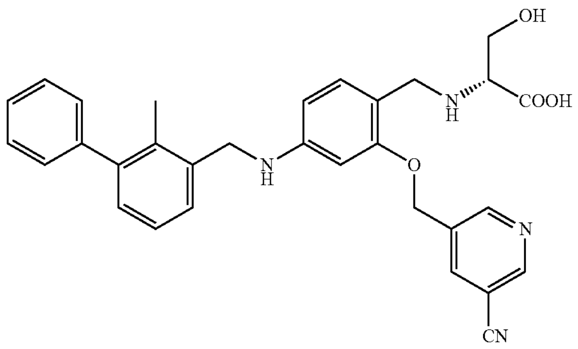

10-3 (133 mg, 0.31 mmol) and D-serine (65 mg, 0.62 mmol) were dissolved in 2.5 mL of anhydrous DMF, added with glacial acetic acid (35 μL, 0.62 mmol), reacted at 35° C. for 24 h, followed by an addition of $NaBH(OAc)_3$ (195 mg, 0.92 mmol), the reaction was continued for 24 h, followed by an addition of water, the resulting mixture was extracted with a mixed solvent of DCM/MeOH (10:1), washed with water, concentrated to dryness, the residue was purified by preparative liquid phase chromatography to obtain 73 mg of a white solid with a yield of 45%. $^1H$ NMR (400 MHz, DMSO-$d_6$): δ 9.00 (dd, J=10.4, 2.4 Hz, 2H), 8.51 (t, J=2.0 Hz, 1H), 7.48-7.44 (m, 2H), 7.39-7.35 (m, 1H), 7.32-7.31 (m, 1H), 7.31-7.29 (m, 1H), 7.28-7.25 (m, 1H), 7.19 (t, J=7.6 Hz, 1H), 7.09 (t, J=8.0 Hz, 2H), 6.41-7.25 (m, 2H), 6.21 (dd, J=8.4, 1.6 Hz, 1H), 5.32 (br, 1H), 5.20 (dd, J=19.6, 12.8 Hz, 2H), 4.26 (d, J=5.2 Hz, 2H), 4.03 (dd, J=46.4, 13.2 Hz, 2H), 3.77 (dd, J=11.2, 4.4 Hz, 1H), 3.64 (dd, J=11.4, 7.2 Hz, 1H), 3.17-3.14 (m, 1H), 2.18 (s, 3H). ESI-HRMS: m/z calculated for $C_{31}H_{30}N_4NaO_4^+$ $[M+Na]^+$ 545.2159, found 545.2157.

Example 11

(1) Synthesis of Intermediate 11-1

11-1

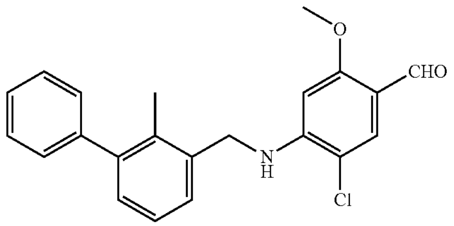

1-2 (418 mg, 1.6 mmol) and 4-amino-5-chloro-2-methoxybenzaldehyde (312 mg, 1.68 mmol) were dissolved in 15 mL of MeCN, then added with $K_2CO_3$ (265 mg, 1.92 mmol), reacted at reflux for 18 h, concentrated, added with water, extracted with EA, the organic phase was washed with water to neutral, and purified by column chromatography to obtain 277 mg of a yellow-white solid with a yield of 47%. $^1H$ NMR (400 MHz, $CDCl_3$): δ 10.14 (s, 1H), 7.79 (s, 1H), 7.47-7.40 (m, 2H), 7.40-7.34 (m, 1H), 7.34-7.28 (m, 3H), 7.28-7.23 (m, 2H), 6.14 (s, 1H), 5.22 (br, 1H), 4.48 (s, 2H), 3.87 (s, 3H), 2.26 (s, 3H). ESI-MS: m/z=366.13 $[M+H]^+$.

(2) Synthesis of Compound 11

11

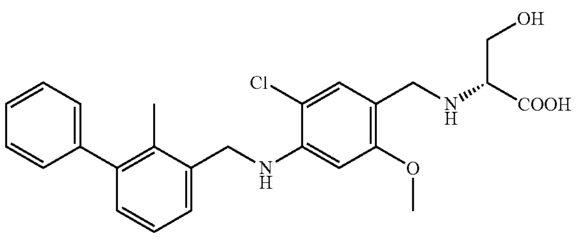

11-1 (150 mg, 0.41 mmol) and D-serine (86 mg, 0.82 mmol) were dissolved in 3 mL of anhydrous DMF, added with glacial acetic acid (47 μL, 0.82 mmol), reacted at 35° C. for 24 h, followed by an addition of $NaBH(OAc)_3$ (195 mg, 0.92 mmol), the reaction was continued for 24 h, followed by an addition of water, the resulting mixture was extracted with a mixed solvent of DCM/MeOH (10:1), the organic phase was washed with water, concentrated to dryness, the residue was purified by preparative liquid phase chromatography to obtain 110 mg of a yellow-white solid with a yield of 59%. $^1H$ NMR (400 MHz, DMSO-$d_6$): δ 7.47-7.43 (m, 2H), 7.40-7.34 (m, 1H), 7.30 (s, 2H), 7.29-7.26 (m, 2H), 7.20 (t, J=7.6 Hz, 1H), 7.09 (d, J=8.0 Hz, 1H), 6.23 (s, 1H), 6.05 (t, J=5.6 Hz, 1H), 4.48 (d, J=5.6 Hz, 2H), 3.93 (dd, J=21.6, 13.2 Hz, 2H), 3.75 (dd, J=11.6, 4.8 Hz, 1H), 3.67 (s, 3H), 3.65-3.60 (m, 1H), 3.15 (dd, J=6.8, 4.4 Hz, 1H), 2.23 (s, 3H). ESI-HRMS: m/z calculated for $C_{25}H_{27}ClN_2NaO_4^+$ $[M+Na]^{+477.1552}$, found 477.1553.

Example 12

12

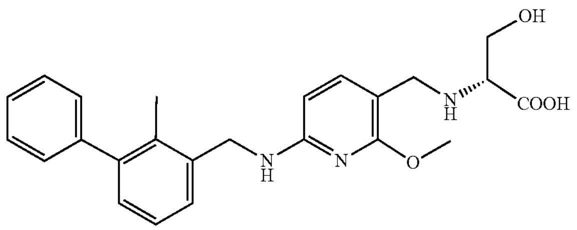

9-2 (347 mg, 1.04 mmol) and D-serine (219 mg, 2.08 mmol) were dissolved in 6 mL of anhydrous DMF, added with glacial acetic acid (119 μL, 2.08 mmol), reacted at 35° C. for 24 h, followed by an addition of $NaBH(OAc)_3$ (664 mg, 3.12 mmol), the reaction was continued for 24 h, followed by an addition of water, the resulting mixture was extracted with a mixed solvent of DCM/MeOH (10:1), the organic phase was washed with water, concentrated to dryness, the residue was purified by preparative liquid phase chromatography to obtain 154 mg of a white solid with a yield of 36%. $^1$H NMR (400 MHz, DMSO-$d_6$): δ 8.17 (br, 2H), 7.46-7.42 (m, 2H), 7.40-7.35 (m, 2H), 7.35-7.30 (m, 1H), 7.31-7.25 (m, 2H), 7.24-7.16 (m, 2H), 7.08 (dd, J=7.6, 0.8 Hz, 1H), 6.08 (d, J=8.0 Hz, 1H), 5.46 (br, 1H), 4.50 (d, J=5.6 Hz, 2H), 3.92 (dd, J=20.0, 11.2 Hz, 2H), 3.81 (s, 3H), 3.76 (dd, J=11.6, 4.4 Hz, 1H), 3.64 (dd, J=11.4, 7.0 Hz, 1H), 3.16 (dd, J=6.8, 4.4 Hz, 1H), 2.20 (s, 3H). ESI-HRMS: m/z calculated for $C_{24}H_{27}N_3NaO_4^+$ $[M+Na]^+$444.1894, found 444.1892.

Example 13

(1) Synthesis of Intermediate 13-1

13-1

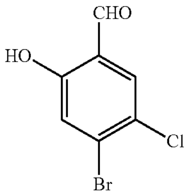

4-Bromo-3-chlorobenzaldehyde (2.53 g, 11.52 mmol), 2-amino-4-chlorobenzoic acid (0.99 g, 5.76 mmol), 1-fluoro-2,4,6-trimethylpyridine trifluoromethanesulfonate (5 g, 17.29 mmol), $Pd(OAc)_2$ (259 mg, 1.15 mmol) and p-toluenesulfonic acid (3.97 g, 23.05 mmol) were suspended in 115 mL of glacial acetic acid, stirred at room temperature for 10 min, then reacted at 90° C. for 24 h, cooled and concentrated, and the residue was purified by column chromatography to obtain 1.50 g of a light yellow solid with a yield of 55%. $^1$H NMR (400 MHz, DMSO-$d_6$): δ 11.33 (s, 1H), 10.20 (s, 1H), 7.73 (s, 1H), 7.38 (s, 1H). ESI-MS: m/z=234.90 $[M+H]^+$.

(2) Synthesis of Intermediate 13-2

13-2

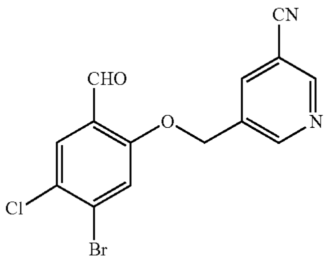

13-1 (471 mg, 2 mmol) was dissolved in 7 mL of MeCN, added with $K_2CO_3$ (304 mg, 2.2 mmol), 5-chloromethylnicotinonitrile (336 mg, 2.2 mmol) and NaI (60 mg, 0.4 mmol), reacted at room temperature for 22 h, the reaction solution was poured into 30 mL of water, then subjected to suction filtration, the filter cake was washed to neutral and dried to obtain 663 mg of a pale yellow powdery solid with a yield of 94%, which was directly used in the next step without purification. $^1$H NMR (400 MHz, DMSO-$d_6$): δ 10.32 (s, 1H), 9.04 (d, J=2.0 Hz, 1H), 9.01 (d, J=2.0 Hz, 1H), 8.54 (t, J=2.0 Hz, 1H), 7.85 (s, 1H), 7.82 (s, 1H), 5.45 (s, 2H). ESI-MS: m/z=350.95 $[M+H]^+$.

(3) Synthesis of Intermediate 13-3

13-3

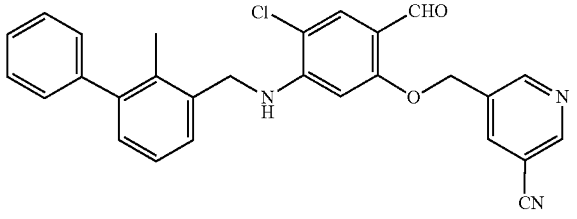

5-2 (354 mg, 1.80 mmol), 13-2 (527 mg, 1.50 mmol), $Cs_2CO_3$ (732 mg, 2.25 mmol), BINAP (187 mg, 0.30 mmol) and $Pd(OAc)_2$ (34 mg, 0.15 mmol) were suspended in 15 mL of dioxane, reacted at 85° C. for 24 h under the protection of Ar, concentrated, added with water, extracted with DCM, the organic phase was washed with water to neutral, and purified by column chromatography to obtain 345 mg of a yellow-white solid with a yield of 49%. $^1$H NMR (400 MHz, DMSO-$d_6$): δ 10.05 (s, 1H), 8.93 (d, J=2.0 Hz, 1H), 8.86 (d, J=2.0 Hz, 1H), 8.37 (t, J=2.0 Hz, 1H), 7.61 (s, 1H), 7.49-7.43 (m, 2H), 7.41-7.35 (m, 1H), 7.35-7.31 (m, 2H), 7.19-7.14 (m, 1H), 7.11 (s, 1H), 7.11-7.08 (m, 2H), 6.29 (s, 1H), 5.27 (s, 2H), 4.58 (d, J=6.0 Hz, 2H), 2.22 (s, 3H). ESI-MS: m/z=468.13 $[M+H]^+$.

(4) Synthesis of Compound 13

13

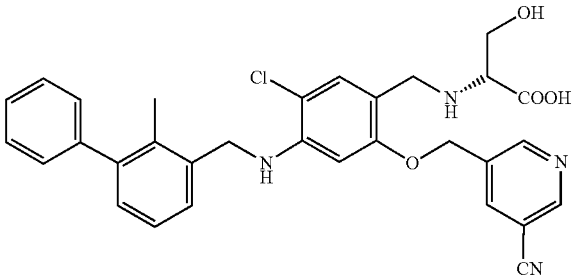

13-3 (436 mg, 0.93 mmol) and D-serine (196 mg, 1.86 mmol) were dissolved in 6 mL of anhydrous DMF, added with glacial acetic acid (109 μL, 1.86 mmol), reacted at 35° C. for 24 h, followed by an addition of $NaBH(OAc)_3$ (594 mg, 2.79 mmol), the reaction was continued for 24 h, followed by an addition of water, the resulting mixture was extracted with a mixed solvent of DCM/MeOH (10:1), the organic phase was washed with water, concentrated to dryness, the residue was purified by preparative liquid phase chromatography to obtain 106 mg of a white solid with a yield of 20%. $^1H$ NMR (400 MHz, DMSO-$d_6$): δ 8.91 (d, J=1.6 Hz, 1H), 8.86 (d, J=2.0 Hz, 1H), 8.37 (s, 1H), 8.17 (br, 2H), 7.46 (t, J=7.2 Hz, 2H), 7.40-7.34 (m, 2H), 7.34-7.29 (m, 2H), 7.16-7.03 (m, 3H), 6.24 (s, 1H), 6.09 (t, J=5.8 Hz, 1H), 5.34 (br, 1H), 5.16 (dd, J=18.4, 13.2 Hz, 2H), 4.43 (d, J=5.6 Hz, 2H), 4.01 (dd, J=33.6, 13.2 Hz, 2H), 3.75 (dd, J=11.2, 4.4 Hz, 1H), 3.63 (dd, J=11.2, 6.8 Hz, 1H), 3.17 (dd, J=6.6, 4.6 Hz, 1H), 2.19 (s, 3H). ESI-HRMS: m/z calculated for $C_{31}H_{29}ClN_4NaO_4^+$ $[M+Na]^+$ 579.1770, found 579.1766.

Example 14

(1) Synthesis of Intermediate 14-1

14-1

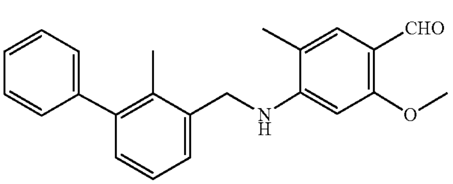

5-2 (473 mg, 2.40 mmol), 4-bromo-2-methoxy-5-methylbenzaldehyde (458 mg, 2.0 mmol), $Cs_2CO_3$ (977 mg, 3.0 mmol), BINAP (249 mg, 0.40 mmol) and $Pd(OAc)_2$ (45 mg, 0.20 mmol) were suspended in 15 mL of dioxane, reacted at reflux under the protection of Ar for 24 h, concentrated, added with water, extracted with EA, the organic phase was washed with water to neutral, and purified by column chromatography to obtain a yellow-white solid 405 mg with a yield of 59%. $^1H$ NMR (400 MHz, DMSO-$d_6$): δ 9.97 (s, 1H), 7.47-7.41 (m, 2H), 7.40-7.32 (m, 2H), 7.33-7.25 (m, 3H), 7.22 (t, J=7.6 Hz, 1H), 7.11 (dd, J=7.2, 1.2 Hz, 1H), 6.69 (t, J=5.8 Hz, 1H), 6.05 (s, 1H), 4.54 (d, J=5.6 Hz, 2H), 3.71 (s, 3H), 2.25 (s, 3H), 2.14 (s, 3H). ESI-MS: m/z=346.18 $[M+H]^+$.

(2) Synthesis of Compound 14

14

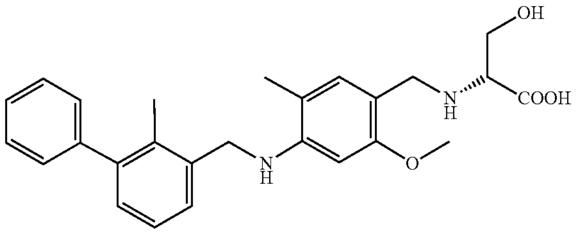

14-1 (257 mg, 0.74 mmol) and D-serine (156 mg, 1.48 mmol) were dissolved in 5 mL of anhydrous DMF, added with glacial acetic acid (85 μL, 1.48 mmol), reacted at 35° C. for 24 h, followed by an addition of $NaBH(OAc)_3$ (473 mg, 2.23 mmol), the reaction was continued for 24 h, followed by an addition of water, the resulting mixture was extracted with a mixed solvent of DCM/MeOH (10:1), the organic phase was washed with water, concentrated to dryness, the residue was purified by preparative liquid phase chromatography to obtain 159 mg of a white solid with a yield of 49%. $^1H$ NMR (400 MHz, DMSO-$d_6$): δ 8.18 (br, 2H), 7.47-7.43 (m, 2H), 7.40-7.33 (m, 1H), 7.32-7.26 (m, 3H), 7.19 (t, J=7.6 Hz, 1H), 7.08 (d, J=7.5 Hz, 1H), 6.94 (s, 1H), 6.10 (s, 1H), 5.68 (t, J=5.6 Hz, 1H), 5.36 (br, 1H), 4.41 (d, J=5.2 Hz, 2H), 3.95 (dd, J=27.2, 13.2 Hz, 2H), 3.77 (dd, J=11.2, 4.4 Hz, 1H), 3.65 (s, 3H), 3.63-3.58 (m, 1H), 3.13 (dd, J=7.2, 4.4 Hz, 1H), 2.24 (s, 3H), 2.09 (s, 3H). ESI-HRMS: m/z calculated for $C_{26}H_{30}N_2NaO_4^+$ $[M+Na]^+$ 457.2098, found 457.2096.

Example 15

(1) Synthesis of Intermediate 15-1

15-1

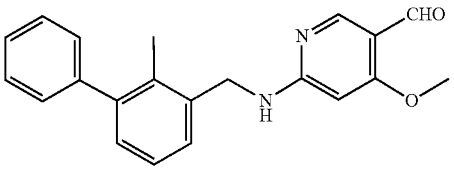

9-1 (660 mg, 1.57 mmol), 2-chloro-4-methoxypyridine-5-carbaldehyde (448 mg, 2.61 mmol), $Cs_2CO_3$ (1.36 g, 4.18 mmol), Sphos (161 mg, 0.39 mmol) and $Pd(OAc)_2$ (44 mg, 0.20 mmol) were suspended in 25 mL of dioxane, reacted at reflux under the protection of Ar for 24 h, then the reaction solution was concentrated, added with water, extracted with DCM, the organic phase was washed with water to neutral, suction filtration was conducted to remove insolubles, the filtrate was concentrated and purified by column chromatography and preparative silica gel plate to obtain 143 mg of a pale yellow solid with a yield of 16%. $^1H$ NMR (400 MHz, $CDCl_3$): δ 10.04 (s, 1H), 8.38 (s, 1H), 7.44-7.39 (m, 2H), 7.38-7.33 (m, 1H), 7.31 (dd, J=6.8, 2.4 Hz, 1H), 7.29-7.26 (m, 2H), 7.25-7.20 (m, 2H), 5.81 (s, 1H), 5.77 (br, 1H), 4.59 (d, J=5.2 Hz, 2H), 3.89 (s, 3H), 2.24 (s, 3H). ESI-MS: m/z=333.16 $[M+H]^+$.

(2) Synthesis of Compound 15

15

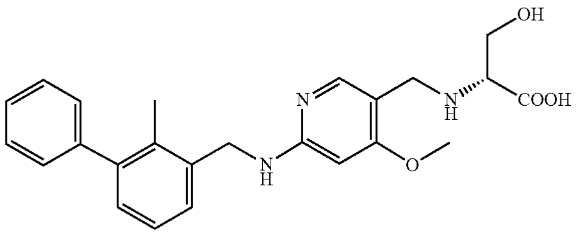

15-1 (203 mg, 0.61 mmol) and D-serine (160 mg, 1.52 mmol) were dissolved in 4 mL of anhydrous DMF, added with glacial acetic acid (87 μL, 1.52 mmol), reacted at 35° C. for 24 h, followed by an addition of $NaBH(OAc)_3$ (388 mg, 1.83 mmol), the reaction was continued for 24 h, followed by an addition of water, the resulting mixture was extracted with n-butanol, the organic phase was concentrated to dryness, and the residue was purified by preparative liquid phase chromatography to obtain 104 mg of a white solid with a yield of 40%. $^1H$ NMR (400 MHz, DMSO-$d_6$): δ 7.81 (s, 1H), 7.45 (t, J=7.4 Hz, 2H), 7.36 (t, J=7.2 Hz, 1H), 7.30-7.26 (m, 3H), 7.19 (t, J=7.4 Hz, 1H), 7.12-7.07 (m, 2H), 6.19 (s, 1H), 5.39 (br, 1H), 4.50 (d, J=5.2 Hz, 2H), 3.93 (dd, J=21.2, 13.6 Hz, 2H), 3.81-3.75 (m, 4H), 3.64 (dd, J=11.4, 7.0 Hz, 1H), 3.18 (dd, J=6.8, 4.4 Hz, 1H), 2.17 (s, 3H). ESI-HRMS: m/z calculated for $C_{24}H_{28}N_3O_4^+$ $[M+H]^+$ 422.2074, found 422.2074.

Example 16

(1) Synthesis of Intermediate 16-1

16-1

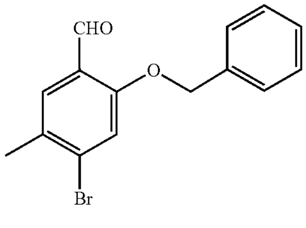

4-Bromo-2-hydroxy-5-methylbenzaldehyde (430 mg, 2 mmol) was dissolved in 10 mL of MeCN, added with $K_2CO_3$ (304 mg, 2.2 mmol), benzyl bromide (376 mg, 2.2 mmol) and NaI (30 mg, 0.2 mmol), reacted at room temperature for 22 h, added with 30 mL of water, the mixture was subjected to suction filtration, the filter cake was washed with water to neutral, and dried to obtain 503 mg of a yellow-white powdery solid with a yield of 82%. $^1H$ NMR (400 MHz, $CDCl_3$): δ 10.45 (s, 1H), 7.69 (s, 1H), 7.45-7.33 (m, 5H), 7.28 (s, 1H), 5.14 (s, 2H), 2.36 (s, 3H). ESI-MS: m/z=327.00 $[M+Na]^+$.

(2) Synthesis of Intermediate 16-2

16-2

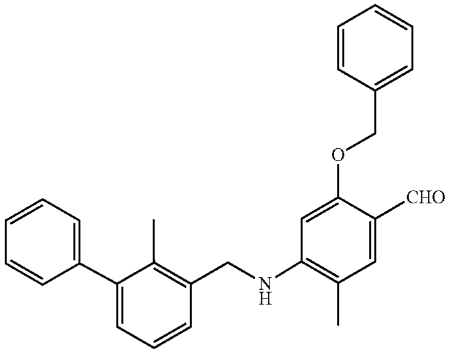

5-2 (367 mg, 1.86 mmol), 16-1 (473 mg, 1.55 mmol), $Cs_2CO_3$ (758 mg, 2.33 mmol), BINAP (193 mg, 0.31 mmol) and $Pd(OAc)_2$ (35 mg, 0.16 mmol) were suspended in 15 mL of dioxane, reacted at reflux under the protection of Ar for 24 h, concentrated, added with water, extracted with EA, the organic phase was washed with water to neutral, and purified by column chromatography to obtain 337 mg of a yellow-white solid with a yield of 52%. $^1H$ NMR (400 MHz, $CDCl_3$): δ 10.29 (s, 1H), 7.60 (d, J=0.8 Hz, 1H), 7.45-7.41 (m, 2H), 7.40-7.33 (m, 5H), 7.33-7.29 (m, 3H), 7.29-7.26 (m, 1H), 7.25-7.23 (m, 2H), 6.14 (s, 1H), 5.12 (s, 2H), 4.39 (s, 2H), 4.34 (br, 1H), 2.22 (s, 3H), 2.10 (s, 3H). ESI-MS: m/z=422.24 $[M+H]^+$.

(2) Synthesis of Compound 16

16

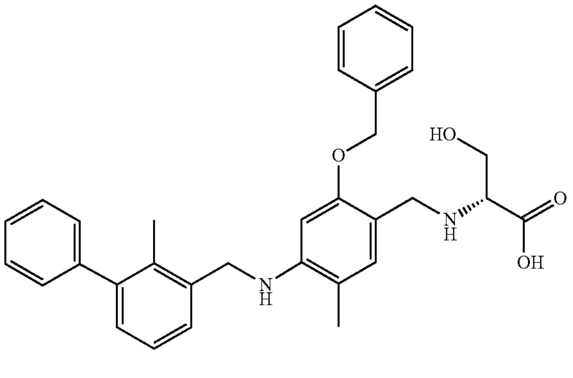

16-2 (297 mg, 0.70 mmol) and D-serine (148 mg, 1.41 mmol) were dissolved in 8 mL of anhydrous DMF and 2 mL of anhydrous methanol, added with glacial acetic acid (80 μL, 1.41 mmol), reacted at 35° C. for 24 h, then added with $NaBH(OAc)_3$ (448 mg, 2.11 mmol), the reaction was continued for 24 h, followed by an addition of water, the resulting mixture was extracted with a mixed solvent of DCM/MeOH=10/1, washed with water, the organic phase was concentrated to dryness, and the residue was purified by preparative liquid phase chromatography to obtain 36 mg of a white solid with a yield of 10%. $^1H$ NMR (400 MHz, DMSO-$d_6$): δ 8.16 (br, 2H), 7.46 (tt, J=8.2, 1.6 Hz, 2H), 7.41-7.37 (m, 1H), 7.35-7.32 (m, 3H), 7.31 (t, J=1.2 Hz, 1H), 7.30-7.24 (m, 3H), 7.21 (dd, J=7.6, 1.6 Hz, 1H), 7.16 (t, J=7.6 Hz, 1H), 7.10 (dd, J=7.4, 1.4 Hz, 1H), 6.97 (s, 1H), 6.13 (s, 1H), 5.70 (t, J=5.6 Hz, 1H), 5.38 (br, 1H), 4.98 (s, 2H), 4.32 (d, J=5.2 Hz, 2H), 3.99 (dd, J=36.2, 13.0 Hz, 2H), 3.78 (dd, J=11.4, 4.4 Hz, 1H), 3.66 (dd, J=11.4, 7.0 Hz, 1H), 3.17 (dd, J=7.2, 4.4 Hz, 1H), 2.20 (s, 3H), 2.09 (s, 3H). ESI-HRMS: m/z calculated for $C_{32}H_{34}N_2NaO_4^+$ $[M+Na]^+$ 533.2411, found 533.2408.

Example 17

(1) Synthesis of Intermediate 17-1

17-1

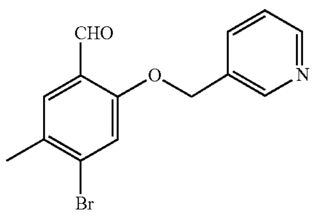

4-Bromo-2-hydroxy-5-methylbenzaldehyde (430 mg, 2 mmol) was dissolved in 10 mL of MeCN, added with $K_2CO_3$ (608 mg, 4.4 mmol), 3-bromomethylpyridine hydrobromide (556 mg, 2.20 mmol) and NaI (30 mg, 0.2 mmol), reacted at room temperature in the dark for 24 h, replenished with 3-bromomethylpyridine hydrobromide (303 mg, 1.20 mmol) and $K_2CO_3$ (332 mg, 2.4 mmol), the reaction was continued for 12 h, followed by an addition of 50 mL of water, the resulting mixture was extracted with EA, the organic phase was washed with water to neutral, and purified by column chromatography to obtain 180 mg of a yellow-white powdery solid with a yield of 29%. $^1H$ NMR (400 MHz, $CDCl_3$): δ 10.41 (s, 1H), 8.71 (s, 1H), 8.64 (d, J=4.0 Hz, 1H), 7.83-7.79 (m, 1H), 7.70 (s, 1H), 7.37 (dd, J=8.0, 4.8 Hz, 1H), 7.29 (s, 1H), 5.17 (s, 2H), 2.38 (s, 3H).

ESI-MS: m/z=306.01 $[M+H]^+$.

(2) Synthesis of Intermediate 17-2

17-2

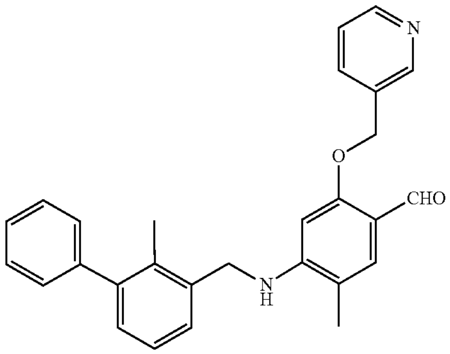

5-2 (571 mg, 2.90 mmol), 17-1 (740 mg, 2.42 mmol), $Cs_2CO_3$ (1.18 g, 3.62 mmol), BINAP (301 mg, 0.48 mmol) and $Pd(OAc)_2$ (55 mg, 0.24 mmol) were suspended in 20 mL of dioxane, reacted at reflux under the protection of Ar for 24 h, concentrated, added with water, extracted with EA, the organic phase was washed with water to neutral, and purified by column chromatography to obtain 386 mg of a yellow-white solid with a yield of 38%. $^1H$ NMR (400 MHz, $CDCl_3$): δ 10.23 (s, 1H), 8.65 (s, 1H), 8.59 (d, J=4.4 Hz, 1H), 7.77 (d, J=8.0 Hz, 1H), 7.60 (s, 1H), 7.44 (t, J=7.4 Hz, 2H), 7.40-7.35 (m, 1H), 7.34-7.27 (m, 4H), 7.27-7.25 (m, 2H), 6.14 (s, 1H), 5.20-5.08 (m, 2H), 4.43 (s, 2H), 4.40 (br, 1H), 2.25 (s, 3H), 2.11 (s, 3H). ESI-MS: m/z=423.21 $[M+H]^+$.

(3) Synthesis of Compound 17

17

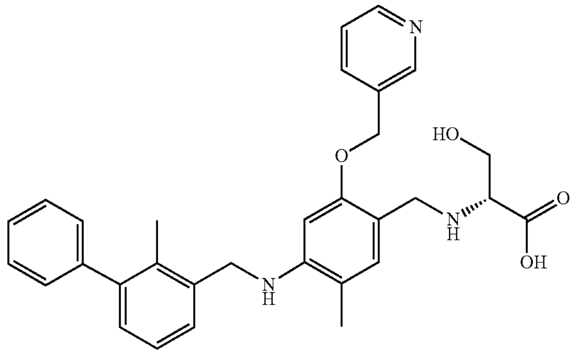

17-2 (310 mg, 0.73 mmol) and D-serine (154 mg, 1.47 mmol) were dissolved in 8 mL of anhydrous DMF and 2 mL of anhydrous methanol, added with glacial acetic acid (85 μL, 1.47 mmol), reacted at 35° C. for 24 h, followed by an addition of $NaBH(OAc)_3$ (467 mg, 2.20 mmol), the reaction was continued for 24 h, followed by an addition of water, the resulting mixture was extracted with a mixed solvent of DCM/MeOH=10/1, washed with water, the organic phase was concentrated to dryness, and the residue was purified by preparative liquid phase chromatography to obtain 51 mg of a white solid with a yield of 14%. $^1H$ NMR (400 MHz, DMSO-$d_6$): δ 8.58 (d, J=1.6 Hz, 1H), 8.47 (dd, J=4.8, 1.6 Hz, 1H), 8.26 (br, 2H), 7.81 (dt, J=8.0, 2.0 Hz, 1H), 7.49-7.42 (m, 2H), 7.40-7.35 (m, 1H), 7.34-7.31 (m, 2H), 7.29 (ddd, J=7.8, 4.8, 0.4 Hz, 1H), 7.21 (dd, J=7.6, 1.2 Hz, 1H), 7.16 (t, J=7.6 Hz, 1H), 7.09 (dd, J=7.4, 1.4 Hz, 1H), 6.98 (s, 1H), 6.15 (s, 1H), 5.69 (t, J=5.6 Hz, 1H), 5.38 (br, 1H), 5.04 (dd, J=15.6, 13.2 Hz, 2H), 4.35 (d, J=5.2 Hz, 2H), 3.99 (dd, J=40.8, 13.2 Hz, 2H), 3.78 (dd, J=11.4, 4.4 Hz, 1H), 3.65 (dd, J=11.2, 7.2 Hz, 1H), 3.17 (dd, J=7.0, 4.6 Hz, 1H), 2.21 (s, 3H), 2.10 (s, 3H). ESI-HRMS: m/z calculated for $C_{31}H_{33}N_3NaO_4^+$ $[M+Na]^+$ 534.2363, found 534.2360.

Example 18

18

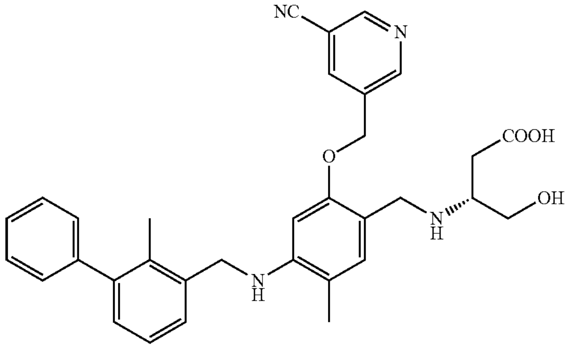

5-4 (313 mg, 0.7 mmol) and (R)-3-amino-4-hydroxybutyric acid (167 mg, 1.40 mmol) were suspended in 6 mL of anhydrous DMF and 2 mL of anhydrous methanol, then added with glacial acetic acid (80 μL, 1.40 mmol), reacted at 35° C. for 24 h, followed by an addition of $NaBH(OAc)_3$ (445 mg, 2.10 mmol), the reaction was continued for 24 h, followed by an addition of water, the resulting mixture was extracted with a mixed solvent of DCM/MeOH (10:1), the organic phase was washed with water, concentrated to dryness, the residue was purified by preparative liquid phase chromatography to obtain 30 mg of a white powdery solid with a yield of 8%. $^1H$ NMR (400 MHz, DMSO-$d_6$): δ 10.00 (br, 2H), 8.91-8.80 (m, 2H), 8.32 (s, 1H), 7.45 (t, J=7.4 Hz, 2H), 7.39-7.33 (m, 3H), 7.16-7.04 (m, 3H), 6.97 (s, 1H), 6.08 (s, 1H), 5.66 (t, J=5.4 Hz, 1H), 5.17-5.07 (m, 2H), 4.34 (d, J=4.8 Hz, 2H), 3.91 (dd, J=68.0, 12.8 Hz, 2H), 3.58 (dd, J=11.6, 4.4 Hz, 1H), 3.47-3.39 (m, 1H), 3.07-3.01 (m, 1H), 2.19 (s, 3H), 2.16-2.13 (m, 2H), 2.11 (s, 3H). ESI-HRMS: m/z calculated for $C_{33}H_{34}N_4NaO_4^+$ $[M+Na]^+$ 573.2472, found 573.2472.

Example 19

(1) Synthesis of Intermediate 19-1

19-1

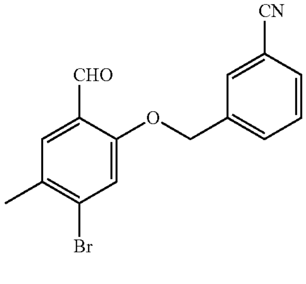

4-Bromo-2-hydroxy-5-methylbenzaldehyde (645 mg, 3 mmol) was dissolved in 9 mL of MeCN, added with $K_2CO_3$ (647 mg, 4.68 mmol), 3-cyanobenzyl bromide (647 mg, 3.3 mmol) and NaI (45 mg, 0.3 mmol), reacted at room temperature for 24 hours, added with 40 mL of water, the resulting mixture was subjected to suction filtration, the filter cake was washed with water to neutral, after being dried, the filter cake was suspended in cyclohexane and subjected to sonication and suction filtration to obtain 801 mg of a yellow-white powdery solid with a yield of 81%. $^1H$ NMR (400 MHz, DMSO-$d_6$): δ 10.36 (s, 1H), 8.01 (s, 1H), 7.85 (t, J=8.6 Hz, 2H), 7.69-7.57 (m, 3H), 5.35 (s, 2H), 2.33 (s, 3H). ESI-MS: m/z=330.00 $[M+H]^+$.

(2) Synthesis of Intermediate 19-2

19-2

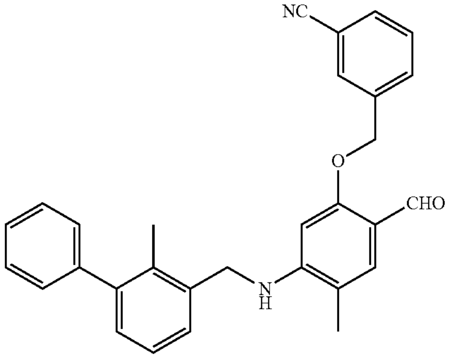

5-2 (548 mg, 2.78 mmol), 19-1 (766 mg, 2.32 mmol), $Cs_2CO_3$ (1.13 g, 3.46 mmol), BINAP (289 mg, 0.46 mmol) and $Pd(OAc)_2$ (52 mg, 0.23 mmol) were suspended in 15 mL of dioxane, reacted at reflux under the protection of Ar for 24 h, concentrated, added with water, extracted with EA, the organic phase was washed with water to neutral, and purified by column chromatography to obtain 382 mg of a yellow-white solid with a yield of 37%. $^1H$ NMR (400 MHz, $CDCl_3$): δ 10.25 (s, 1H), 7.68 (s, 1H), 7.67-7.58 (m, 3H), 7.48 (t, J=7.6 Hz, 1H), 7.46-7.41 (m, 2H), 7.39-7.35 (m, 1H), 7.34-7.28 (m, 2H), 7.28-7.23 (m, 3H), 6.08 (s, 1H), 5.14 (s, 2H), 4.46 (br, 1H), 4.41 (d, J=4.8 Hz, 2H), 2.24 (s, 3H), 2.12 (s, 3H). ESI-MS: m/z=447.21 $[M+H]^+$.

(3) Synthesis of Compound 19

19

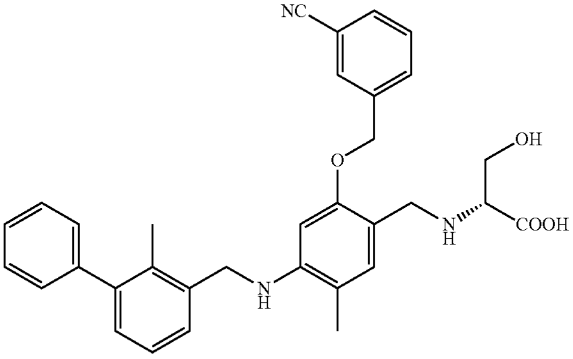

19-2 (341 mg, 0.76 mmol) and D-serine (161 mg, 1.53 mmol) were dissolved in 7 mL of anhydrous DMF, added with glacial acetic acid (87 μL, 1.53 mmol), reacted at 35° C. for 24 h, followed by an addition of $NaBH(OAc)_3$ (486 mg, 2.29 mmol), the reaction was continued for 24 h, followed by an addition of water, the resulting mixture was extracted with a mixed solvent of DCM/MeOH=10/1, the organic phase was washed with water and concentrated to dryness, the residue was purified by preparative liquid phase chromatography to obtain 320 mg of a white solid with a yield of 79%. $^1$H NMR (400 MHz, DMSO-$d_6$): δ 8.29 (br, 1H), 7.87 (s, 1H), 7.74-7.68 (m, 2H), 7.47-7.43 (m, 3H), 7.39-7.35 (m, 1H), 7.33-7.28 (m, 2H), 7.17 (dd, J=7.2, 1.2 Hz, 1H), 7.13 (t, J=7.4 Hz, 1H), 7.08 (dd, J=7.2, 1.6 Hz, 1H), 6.99 (s, 1H), 6.09 (s, 1H), 5.70 (t, J=5.6 Hz, 1H), 5.38 (br, 1H), 5.12-5.02 (m, 2H), 4.33 (d, J=5.2 Hz, 2H), 4.02 (dd, J=40.4, 13.0 Hz, 2H), 3.79 (dd, J=11.6, 4.4 Hz, 1H), 3.65 (dd, J=11.2, 7.2 Hz, 1H), 3.18 (dd, J=6.9, 4.6 Hz, 1H), 2.19 (s, 3H), 2.10 (s, 3H). ESI-HRMS: m/z calculated for $C_{33}H_{33}N_3NaO_4^+$ [M+Na]$^+$ 558.2363, found 558.2364.

Example 20

(1) Synthesis of Intermediate 20-1

20-1

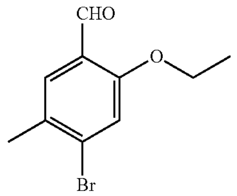

4-Bromo-2-hydroxy-5-methylbenzaldehyde (660 mg, 3.07 mmol) was dissolved in 15 mL of MeCN, added with $K_2CO_3$ (467 mg, 3.38 mmol) and iodoethane (527 mg, 3.38 mmol), reacted at 60° C. for 24 h, then concentrated, added with water, extract with EA, the organic phase was washed with water to neutral, and purified by column chromatography to obtain 537 mg of a yellow-white powdery solid with a yield of 72%. $^1$H NMR (400 MHz, $CDCl_3$): δ 10.41 (s, 1H), 7.66 (s, 1H), 7.18 (s, 1H), 4.12 (q, J=7.4 Hz, 2H), 2.35 (s, 3H), 1.47 (t, J=7.4 Hz, 3H). ESI-MS: m/z=243.01 [M+H]$^+$.

(2) Synthesis of Intermediate 20-2

20-2

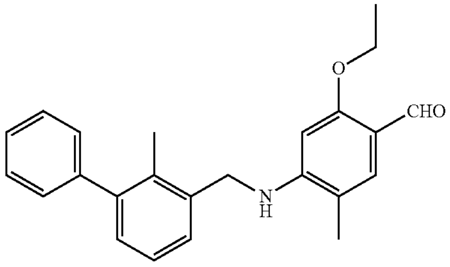

5-2 (591 mg, 3.0 mmol), 20-1 (608 mg, 2.50 mmol), $Cs_2CO_3$ (1.22 g, 3.75 mmol), BINAP (311 mg, 0.50 mmol) and $Pd(OAc)_2$ (56 mg, 0.25 mmol) were suspended in 15 mL of dioxane, reacted at reflux under the protection of Ar for 24 h, concentrated, added with water, extracted with EA, the organic phase was washed with water to neutral, and purified by column chromatography to obtain 350 mg of a yellow-white solid with a yield of 39%. $^1$H NMR (400 MHz, $CDCl_3$): δ 10.22 (s, 1H), 7.58 (d, J=0.8 Hz, 1H), 7.46-7.40 (m, 2H), 7.40-7.34 (m, 1H), 7.34-7.27 (m, 3H), 7.26 (d, J=3.6 Hz, 1H), 7.24 (s, 1H), 6.09 (s, 1H), 4.44 (d, J=4.0 Hz, 2H), 4.39 (br, 1H), 4.09 (q, J=6.8 Hz, 2H), 2.26 (s, 3H), 2.09 (s, 3H), 1.43 (t, J=6.8 Hz, 3H). ESI-MS: m/z=360.21 [M+H]$^+$.

(3) Synthesis of Compound 20

20

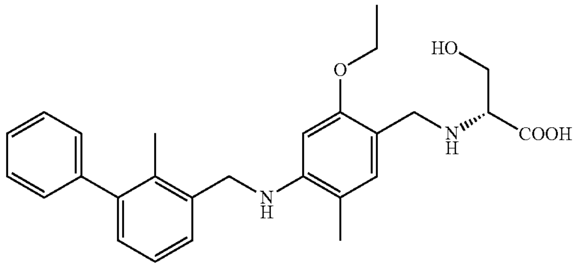

20-2 (296 mg, 0.82 mmol) and D-serine (173 mg, 1.65 mmol) were dissolved in 5.5 mL of anhydrous DMF, added with glacial acetic acid (94 μL, 1.65 mmol), reacted at 35° C. for 24 h, then added with $NaBH(OAc)_3$ (523 mg, 2.47 mmol), the reaction was continued for 24 h, followed by an addition of water, the resulting mixture was extracted with a mixed solvent of DCM/MeOH=10/1, washed with water, the organic phase was concentrated to dryness, and the residue was purified by preparative liquid phase chromatography to obtain 290 mg of a white solid with a yield of 79%. $^1$H NMR (400 MHz, DMSO-$d_6$): δ 8.21 (br, 2H), 7.47-7.43 (m, 2H), 7.40-7.34 (m, 1H), 7.30-7.26 (m, 3H), 7.18 (t, J=7.6 Hz, 1H), 7.08 (dd, J=7.6, 1.2 Hz, 1H), 6.93 (s, 1H), 6.06 (s, 1H), 5.71 (t, J=5.6 Hz, 1H), 5.41 (br, 1H), 4.40 (d, J=5.6 Hz, 2H), 4.02-3.84 (m, 4H), 3.78 (dd, J=11.6, 4.4 Hz, 1H), 3.63 (dd, J=11.6, 7.6 Hz, 1H), 3.14 (dd, J=7.2, 4.4 Hz, 1H), 2.23 (s, 3H), 2.09 (s, 3H), 1.24 (t, J=7.0 Hz, 3H). ESI-HRMS: m/z calculated for $C_{27}H_{32}N_2NaO_4^+$[M+Na]$^+$ 471.2254, found 471.2254.

Example 21

21

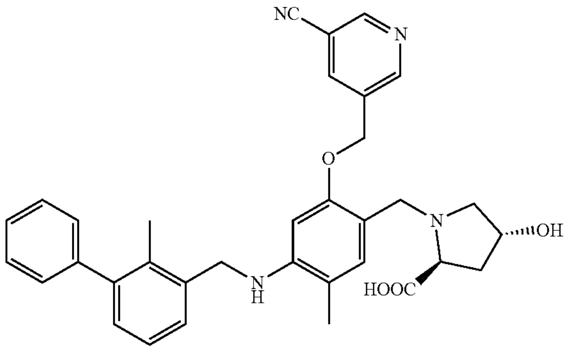

5-4 (339 mg, 0.76 mmol) and L-hydroxyproline (199 mg, 1.52 mmol) were suspended in 6.5 mL of anhydrous DMF, added with glacial acetic acid (87 μL, 1.52 mmol), reacted at 35° C. for 24 h, followed by an addition of $NaBH(OAc)_3$ (482 mg, 2.27 mmol), the reaction was continued for 24 h, followed by an addition of water, the resulting mixture was extracted with a mixed solvent of DCM/MeOH (10:1), washed with water, concentrated to dryness, the residue was purified by preparative liquid phase chromatography to obtain 150 mg of a white powdery solid with a yield of 35%. $^1$H NMR (400 MHz, DMSO-$d_6$): δ 8.91 (d, J=2.0 Hz, 1H), 8.85 (d, J=2.0 Hz, 1H), 8.36 (t, J=2.2 Hz, 1H), 7.47-7.43 (m, 2H), 7.40-7.35 (m, 1H), 7.34-7.32 (m, 1H), 7.32-7.31 (m, 1H), 7.20 (dd, J=7.6, 1.6 Hz, 1H), 7.14 (t, J=7.6 Hz, 1H), 7.08 (dd, J=7.6, 1.6 Hz, 1H), 7.01 (s, 1H), 6.11 (s, 1H), 5.71 (t, J=5.8 Hz, 1H), 5.36 (br, 1H), 5.15 (dd, J=23.2, 13.6 Hz, 2H), 4.35 (d, J=5.6 Hz, 2H), 4.28-4.24 (m, 1H), 4.13 (dd, J=63.0, 13.0 Hz, 2H), 3.71 (t, J=8.2 Hz, 1H), 3.33 (dd, J=11.6, 4.8 Hz, 1H), 2.86 (dd, J=11.6, 3.2 Hz, 1H), 2.20 (s, 3H), 2.11 (s, 3H), 2.08-1.98 (m, 2H). ESI-HRMS: m/z calculated for $C_{34}H_{34}N_4NaO_4^+$ [M+Na]$^+$ 585.2472, found 585.2471.

Example 22

22

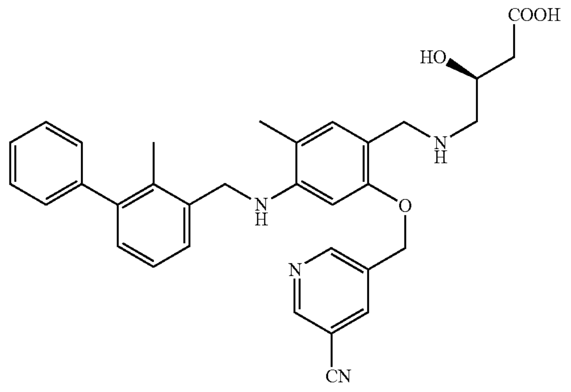

5-4 (313 mg, 0.7 mmol) and (S)-(+)-4-amino-3-hydroxybutyric acid (167 mg, 1.40 mmol) were suspended in 6 mL of anhydrous DMF and 2 mL of anhydrous methanol, added with glacial acetic acid (80 μL, 1.40 mmol), reacted at 35° C. for 24 h, followed by an addition of NaBH(OAc)$_3$ (445 mg, 2.10 mmol), the reaction was continued for 24 h, followed by an addition of water, the resulting mixture was extracted with a mixed solvent of DCM/MeOH (10:1), the organic phase was washed with water and concentrated to dryness, the residue was purified by preparative liquid phase chromatography to obtain 97 mg of a white powdery solid with a yield of 25%. $^1$H NMR (400 MHz, DMSO-$d_6$): δ 8.90 (d, J=2.0 Hz, 1H), 8.83 (d, J=2.0 Hz, 1H), 8.29 (t, J=2.2 Hz, 1H), 7.48-7.42 (m, 2H), 7.40-7.34 (m, 1H), 7.34-7.31 (m, 2H), 7.17 (dd, J=7.6, 1.6 Hz, 1H), 7.13 (t, J=7.4 Hz, 1H), 7.07 (dd, J=7.4, 1.8 Hz, 1H), 6.96 (s, 1H), 6.08 (s, 1H), 5.57 (t, J=5.6 Hz, 1H), 5.11 (s, 2H), 4.33 (d, J=5.2 Hz, 2H), 3.88 (qui, J=5.6 Hz, 1H), 3.76 (dd, J=17.0, 13.0 Hz, 2H), 2.68 (d, J=5.6 Hz, 2H), 2.29 (ddd, J=32.2, 15.2, 5.6 Hz, 2H), 2.20 (s, 3H), 2.10 (s, 3H).

ESI-HRMS: m/z calculated for $C_{29}H_{26}N_3O$ [M-$C_4H_8NO_3$]$^+$ 432.2070, found 432.2069.

Example 23

23

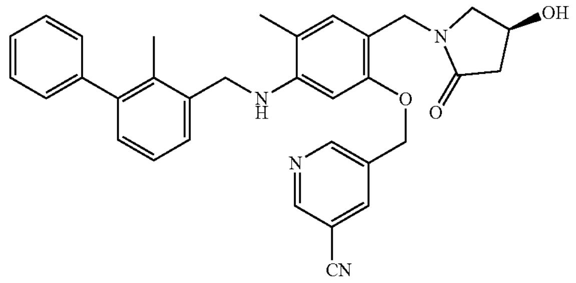

It is the by-product isolated in Example 22 in an amount of 38 mg. $^1$H NMR (400 MHz, $CDCl_3$): δ 8.80 (d, J=1.6 Hz, 2H), 8.08 (t, J=2.0 Hz, 1H), 7.46-7.41 (m, 2H), 7.39-7.34 (m, 1H), 7.34-7.32 (m, 1H), 7.32-7.31 (m, 1H), 7.30-7.27 (m, 1H), 7.24 (d, J=1.6 Hz, 1H), 7.23 (s, 1H), 6.96 (s, 1H), 6.15 (s, 1H), 5.09 (s, 2H), 4.55 (d, J=14.4 Hz, 1H), 4.45 (br, 1H), 4.34 (d, J=14.4 Hz, 1H), 4.32 (s, 2H), 3.86 (br, 1H), 3.50 (dd, J=10.8, 5.6 Hz, 1H), 3.20 (dd, J=10.8, 2.0 Hz, 1H), 2.69 (dd, J=17.2, 6.8 Hz, 1H), 2.44 (br, 1H), 2.39 (dd, J=17.4, 2.2 Hz, 1H), 2.25 (s, 3H), 2.08 (s, 3H). ESI-HRMS: m/z calculated for $C_{33}H_{33}N_4O_3^+$ [M+H]$^+$ 533.2547, found 533.2545.

Example 24

24

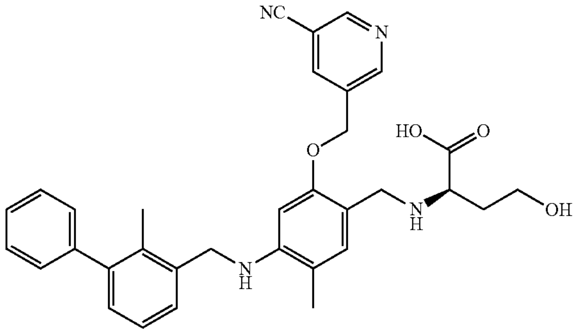

5-4 (313 mg, 0.7 mmol) and D-homoserine (167 mg, 1.40 mmol) were suspended in 6 mL of anhydrous DMF and 2 mL of anhydrous methanol, then added with glacial acetic acid (80 μL, 1.40 mmol), reacted at 35° C. for 24 h, followed by an addition of NaBH(OAc)$_3$ (445 mg, 2.10 mmol), the reaction was continued for 24 h, followed by an addition of water, the resulting mixture was extracted with a mixed solvent of DCM/MeOH (10:1), the organic phase was washed with water and concentrated to dryness, the residue was purified by preparative liquid phase chromatography to obtain 230 mg of a white powder solid with a yield of 60%. $^1$H NMR (400 MHz, DMSO-$d_6$): δ 8.90 (d, J=2.0 Hz, 1H), 8.85 (d, J=2.0 Hz, 1H), 8.35 (t, J=2.0 Hz, 1H), 8.15 (br, 2H), 7.48-7.42 (m, 2H), 7.40-7.36 (m, 1H), 7.35-7.31 (m, 2H), 7.17-7.10 (m, 2H), 7.07 (dd, J=6.8, 2.0 Hz, 1H), 7.01 (s, 1H), 6.08 (s, 1H), 5.73 (t, J=5.6 Hz, 1H), 5.54 (br, 1H), 5.13 (dd, J=18.0, 13.2 Hz, 2H), 4.35 (d, J=5.6 Hz, 2H), 4.03-3.89 (m, 2H), 3.56-3.44 (m, 2H), 3.21 (t, J=6.4 Hz, 1H), 2.19 (s, 3H), 2.11 (s, 3H), 1.93-1.67 (m, 2H). ESI-HRMS: m/z calculated for $C_{33}H_{34}N_4NaO_4^+$ [M+Na]$^+$ 573.2472, found 573.2472.

Example 25

25

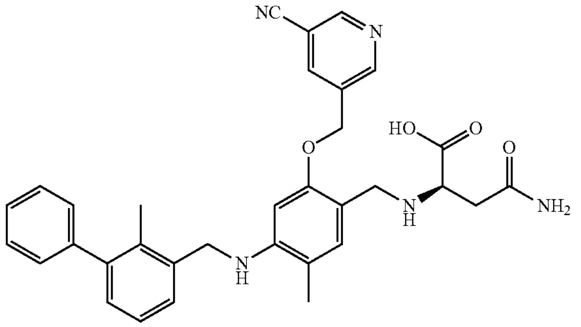

5-4 (313 mg, 0.7 mmol) and D-asparagine (185 mg, 1.40 mmol) were suspended in 8 mL of anhydrous DMF, then added with glacial acetic acid (80 μL, 1.40 mmol), reacted at 35° C. for 24 hours, followed by an addition of NaBH$(OAc)_3$ (445 mg, 2.10 mmol), the reaction was continued for 24 h, followed by an addition of water, the resulting mixture was extracted with a mixed solvent of DCM/MeOH (10:1), the organic phase was washed with water and concentrated to dryness, the residue was purified by preparative liquid phase chromatography to obtain 180 mg of a white powdery solid with a yield of 46%. $^1$H NMR (400 MHz, DMSO-$d_6$): δ 8.89 (d, J=2.0 Hz, 1H), 8.85 (d, J=2.0 Hz, 1H), 8.34 (t, J=2.0 Hz, 1H), 7.78 (s, 1H), 7.49-7.43 (m, 2H), 7.39-7.35 (m, 1H), 7.35-7.34 (m, 1H), 7.33-7.32 (m, 1H), 7.16-7.09 (m, 3H), 7.07 (dd, J=7.0, 2.2 Hz, 1H), 6.96 (s, 1H), 6.07 (s, 1H), 5.73 (t, J=5.8 Hz, 1H), 5.16 (s, 2H), 4.34 (d, J=5.2 Hz, 2H), 4.04 (dd, J=21.4, 13.0 Hz, 2H), 3.36 (dd, J=9.2, 4.0 Hz, 1H), 2.73 (dd, J=16.6, 3.8 Hz, 1H), 2.43 (dd, J=16.6, 9.0 Hz, 1H), 2.19 (s, 3H), 2.11 (s, 3H). ESI-HRMS: m/z calculated for $C_{33}H_{33}N_5NaO_4^+$ [M+Na]$^+$ 586.2425, found 586.2422.

Example 26

(1) Synthesis of Intermediate 26-1

26-1

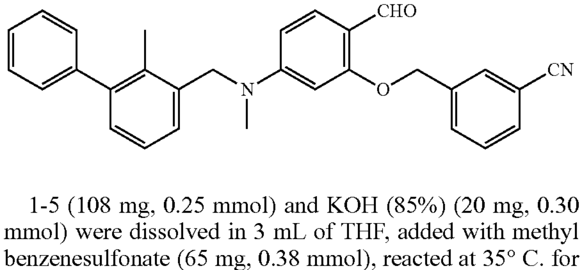

1-5 (108 mg, 0.25 mmol) and KOH (85%) (20 mg, 0.30 mmol) were dissolved in 3 mL of THF, added with methyl benzenesulfonate (65 mg, 0.38 mmol), reacted at 35° C. for 25 h, then replenished with methyl benzenesulfonate (13 mg, 0.08 mmol), the reaction was continued for 15 h, the reaction system was concentrated, added with water, extracted with DCM, the organic phase was washed with water, and purified by recrystallization to obtain 70 mg of a yellow-white solid with a yield of 63%. $^1$H NMR (400 MHz, $CDCl_3$): δ 10.24 (s, 1H), 7.75 (d, J=8.8 Hz, 1H), 7.69 (s, 1H), 7.67-7.59 (m, 2H), 7.51-7.41 (m, 3H), 7.41-7.35 (m, 1H), 7.34-7.29 (m, 2H), 7.23-7.15 (m, 2H), 6.94 (dd, J=6.4, 2.4 Hz, 1H), 6.38 (dd, J=8.8, 2.0 Hz, 1H), 6.09 (d, J=2.4 Hz, 1H), 5.14 (s, 2H), 4.59 (s, 2H), 3.19 (s, 3H), 2.18 (s, 3H). ESI-MS: m/z=447.22 [M+H]$^+$.

(2) Synthesis of Compound 26

26

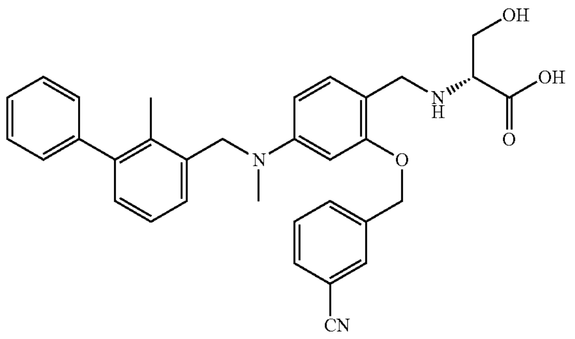

26-1 (89 mg, 0.2 mmol) and D-serine (42 mg, 0.40 mmol) were suspended in 2 mL of anhydrous DMF, then added with glacial acetic acid (23 μL, 0.40 mmol), reacted at 35° C. for 24 h, followed by an addition of NaBH$(OAc)_3$ (131 mg, 0.6 mmol), the reaction was continued for 14 h, followed by an addition of water, the resulting mixture was extracted with a mixed solvent of DCM/MeOH (10:1), washed with water, concentrated to dryness, and the residue was purified by preparative liquid phase chromatography to obtain 64 mg of a yellow-white powdery solid with a yield of 60%. $^1$H NMR (400 MHz, DMSO-$d_6$): δ 8.33 (br, 2H), 7.98 (s, 1H), 7.85 (d, J=8.0 Hz, 1H), 7.77 (d, J=7.6 Hz, 1H), 7.53 (t, J=7.6 Hz, 1H), 7.46 (t, J=7.6 Hz, 2H), 7.41-7.35 (m, 1H), 7.33-7.29 (m, 2H), 7.17-7.11 (m, 2H), 7.08 (d, J=7.6 Hz, 1H), 6.83 (d, J=7.6 Hz, 1H), 6.37 (d, J=2.0 Hz, 1H), 6.25 (dd, J=8.4, 2.0 Hz, 1H), 5.39 (br, 1H), 5.21 (dd, J=17.2, 13.2 Hz, 2H), 4.56 (s, 2H), 4.06 (dd, J=42.4, 12.8 Hz, 2H), 3.78 (dd, J=11.6, 4.4 Hz, 1H), 3.66 (dd, J=11.2, 7.2 Hz, 1H), 3.18 (dd, J=6.8, 4.4 Hz, 1H), 3.04 (s, 3H), 2.14 (s, 3H). ESI-HRMS: m/z calculated for $C_{33}H_{33}N_3NaO_4^+$ [M+Na]$^+$ 558.2363, found 558.2361.

Example 27

27

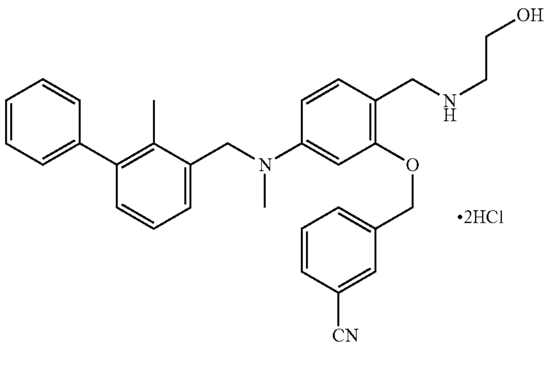

•2HCl 26-1 (70 mg, 0.16 mmol) and ethanolamine (19 mg, 0.31 mmol) were dissolved in 2 mL of DCE and 0.5 mL of anhydrous DMF, then added with glacial acetic acid (18 μL, 0.31 mmol), reacted at 35° C. for 24 h, followed by an addition of $NaBH(OAc)_3$ (103 mg, 0.49 mmol), the reaction was continued for 12 h, followed by an addition of water, the resulting mixture was extracted with a mixed solvent of DCM/MeOH (10:1), the organic phase was washed with water and concentrated to dryness, the residue was purified by column chromatography to obtain an oily substance. The oily substance was dissolved in DCM, added dropwise with 3 mL of 1N HCl ether solution, stirred at room temperature for 30 min, subjected to suction filtration, and the filter cake was purified by preparative liquid phase chromatography again to obtain 34 mg of a white solid with a yield of 38%. $^1H$ NMR (400 MHz, DMSO-$d_6$): δ 9.00 (s, 2H), 7.98 (s, 1H), 7.83 (d, J=7.6 Hz, 1H), 7.80-7.74 (m, 1H), 7.55 (t, J=7.8 Hz, 1H), 7.48-7.42 (m, 2H), 7.38-7.34 (m, 1H), 7.32-7.27 (m, 3H), 7.13 (t, J=7.6 Hz, 1H), 7.07 (dd, J=7.4, 1.0 Hz, 1H), 6.87 (d, J=7.2 Hz, 1H), 6.47 (s, 1H), 6.35 (d, J=5.6 Hz, 1H), 5.59 (br, 6H), 5.22 (s, 2H), 4.60 (s, 2H), 4.04 (t, J=4.8 Hz, 2H), 3.66 (t, J=5.4 Hz, 2H), 3.07 (s, 3H), 2.96-2.85 (m, 2H), 2.13 (s, 3H). ESI-HRMS: m/z calculated for $C_{32}H_{33}N_3NaO_2^+$ $[M+Na]^+$ 514.2465, found 514.2460.

Example 28

(1) Synthesis of Intermediate 28-1

28-1

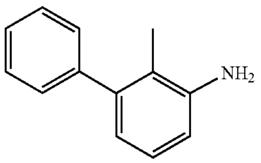

3-Bromo-2-methylaniline (2.79 g, 15 mmol), phenylboronic acid (2.74 g, 22.5 mmol), cesium acetate (7.20 g, 37.51 mmol) and $PdCl_2$(dppf) (1.10 g, 1.50 mmol) were suspended in 48 mL of THF, reacted at reflux under argon protection for 24 h, cooled, concentrated, the residue was added with water, extracted with DCM, the organic phase was washed with water, concentrated and purified by column chromatography to obtain 2.61 g of a brown solid with a yield of 95%. $^1H$ NMR (400 MHz, $CDCl_3$): δ 7.41-7.37 (m, 2H), 7.36-7.27 (m, 3H), 7.07 (t, J=7.8 Hz, 1H), 6.70 (d, J=7.6 Hz, 2H), 3.69 (br, 2H), 2.06 (s, 3H). ESI-MS: m/z=184.12 $[M+H]^+$.

(2) Synthesis of Intermediate 28-2

28-2

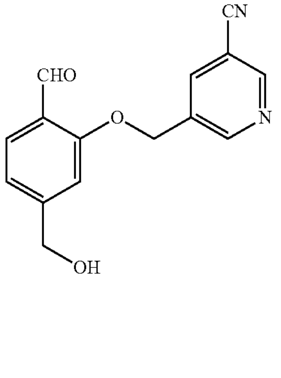

2-Hydroxy-4-hydroxymethylbenzaldehyde (683 mg, 4.49 mmol) was dissolved in 20 mL of MeCN, added with $K_2CO_3$ (683 mg, 4.94 mmol) and 5-chloromethylnicotinonitrile (755 mg, 4.95 mmol), reacted at 60° C. for 10 h, added with 230 mL of water, the mixture was subjected to suction filtration, the filter cake was dried to obtain 1.01 g of a yellow-white powdery solid with a yield of 84%, which could be used directly in the next step without purification. $^1H$ NMR (400 MHz, DMSO-$d_6$): δ 10.41 (d, J=0.8 Hz, 1H), 9.04 (dd, J=3.2, 2.0 Hz, 2H), 8.55 (t, J=2.0, 1H), 7.71 (d, J=7.6 Hz, 1H), 7.29 (d, J=0.8 Hz, 1H), 7.08 (ddd, J=8.0, 1.2, 0.8 Hz, 1H), 5.49 (t, J=5.6 Hz, 1H), 5.39 (s, 2H), 4.59 (d, J=5.6 Hz, 2H). ESI-MS: m/z=269.10 $[M+H]^+$.

(3) Synthesis of Intermediate 28-3

28-3

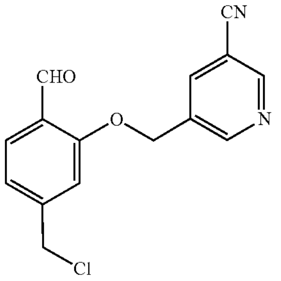

28-2 (838 mg, 3.12 mmol) and pyridine (494 mg, 6.24 mmol) were dissolved in 20 mL of anhydrous DCM and 2 mL of anhydrous DMF, added dropwise with 4 mL of MsCl (537 mg, 4.69 mmol) in anhydrous DCM at 0° C.; after the addition, the reaction was carried out at room temperature for 24 h, water was added then, extraction was performed with DCM, the organic phase was washed with water, concentrated and purified by column chromatography to obtain 565 mg of a yellow-white solid with a yield of 63%. $^1H$ NMR (400 MHz, DMSO-$d_6$): δ 10.42 (d, J=0.4 Hz, 1H), 9.04 (dd, J=3.6, 2.0 Hz, 2H), 8.56 (t, J=2.0 Hz, 1H), 7.76 (d, J=7.6 Hz, 1H), 7.44 (d, J=1.6 Hz, 1H), 7.21 (d, J=8.0 Hz, 1H), 5.41 (s, 2H), 4.83 (s, 2H). ESI-MS: m/z=287.05 $[M+H]^+$.

(4) Synthesis of Intermediate 28-4

28-4

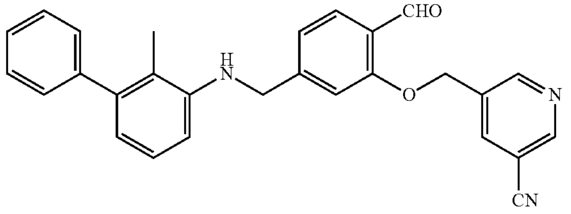

28-3 (397 mg, 1.38 mmol) was dissolved in 8 mL of MeCN and 2.5 mL of DMF, added with $K_2CO_3$ (229 mg, 1.66 mmol), 28-1 (379 mg, 2.07 mmol) and NaI (42 mg, 0.28 mmol), reacted at 30° C. for 24 h, then added with water, extracted with EA, the organic phase was washed with water to neutral, concentrated and purified by column chromatography to obtain 188 mg of a light yellow powdery solid with a yield of 31%. $^1$H NMR (400 MHz, $CDCl_3$): δ 10.46 (s, 1H), 8.87 (d, J=2.4 Hz, 1H), 8.85 (d, J=2.0 Hz, 1H), 8.06 (t, J=2.2 Hz, 1H), 7.88 (d, J=7.6 Hz, 1H), 7.44-7.39 (m, 2H), 7.37-7.29 (m, 3H), 7.17 (d, J=8.0 Hz, 1H), 7.09 (t, J=7.8 Hz, 2H), 6.72 (d, J=7.6 Hz, 1H), 6.46 (d, J=8.0 Hz, 1H), 5.24 (s, 2H), 4.50 (s, 2H), 4.19 (br, 1H), 2.11 (s, 3H). ESI-MS: m/z=434.19 $[M+H]^+$.

(3) Synthesis of Compound 28

28

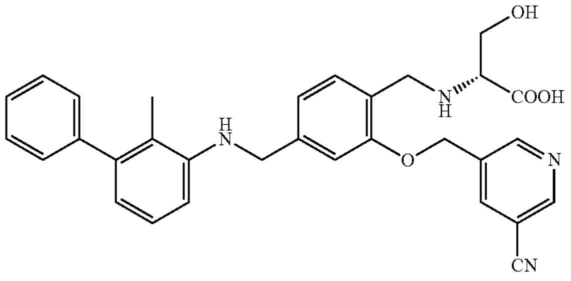

28-4 (278 mg, 0.64 mmol) and D-serine (135 mg, 1.28 mmol) were suspended in 6 mL of anhydrous DMF and 2 mL of anhydrous MeOH, then added with glacial acetic acid (73 μL, 1.28 mmol), reacted at 35° C. for 24 h, followed by an addition of $NaBH(OAc)_3$ (408 mg, 1.93 mmol), the reaction was continued for 24 h, followed by an addition of water, the resulting mixture was extracted with a mixed solvent of DCM/MeOH (10:1), the organic phase was washed with water, concentrated to dryness, the residue was purified by preparative liquid phase chromatography to obtain 78 mg of a white powder solid with a yield of 23%. $^1$H NMR (400 MHz, DMSO-$d_6$): δ 9.02 (d, J=2.4 Hz, 1H), 8.98 (d, J=2.0 Hz, 1H), 8.50 (t, J=2.0 Hz, 1H), 7.43-7.38 (m, 2H), 7.38-7.31 (m, 2H), 7.29-7.24 (m, 2H), 7.20 (s, 1H), 7.03 (d, J=7.6 Hz, 1H), 6.91 (t, J=7.8 Hz, 1H), 6.42 (dd, J=7.6, 0.8 Hz, 1H), 6.37 (d, J=8.0 Hz, 1H), 5.76 (t, J=6.0 Hz, 1H), 5.27 (dd, J=18.8, 12.8 Hz, 2H), 4.37 (d, J=5.6 Hz, 2H), 4.10 (dd, J=20.6, 13.4 Hz, 2H), 3.75 (dd, J=11.2, 4.4 Hz, 1H), 3.63 (dd, J=11.2, 6.8 Hz, 1H), 3.19 (dd, J=6.8, 4.4 Hz, 1H), 2.03 (s, 3H). ESI-HRMS: m/z calculated for $C_{31}H_{31}N_4O_4^+$ $[M+H]^+$ 523.2340, found 523.2338.

Example 29

(1) Synthesis of Intermediate 29-1

29-1

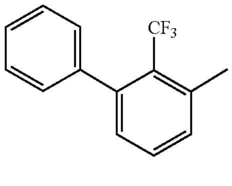

1-Bromo-3-methyl-2-(trifluoromethyl)benzene (10.25 g, 42.88 mmol), phenylboronic acid (7.32 g, 60.03 mmol), cesium acetate (20.58 g, 107.22 mmol) and $PdCl_2$ (dppf) (3.15 g, 4.29 mmol) were suspended in 100 mL of THF, reacted at reflux under the protection of argon for 36 h, cooled, concentrated, the residue was added with water, extracted with DCM, the organic phase was washed with water, concentrated and purified by column chromatography to obtain 5.3 g of a colorless oil with a yield of 52%. $^1$H NMR (400 MHz, $CDCl_3$): δ 7.41-7.31 (m, 4H), 7.28-7.25 (m, 3H), 7.12-7.08 (m, 1H), 2.57 (q, J=2.8 Hz, 3H).

(2) Synthesis of Intermediate 29-2

29-2

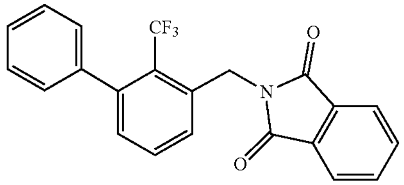

29-1 (4.48 g, 18.96 mmol) was dissolved in 70 mL of $CCl_4$, added with NBS (3.37 g, 18.96 mmol) and 75% BPO (304 mg, 1.26 mmol), reacted at reflux for 11 h, concentrated to dryness, added with water, extracted with DCM, the organic phase was washed with water, then washed with brine, dried over anhydrous $Na_2SO_4$, subjected to suction filtration, the filtrate was concentrated to dryness, the residue was dissolved in 50 mL of DMF, added with potassium phthalimide (4.05 g, 21.87 mmol), reacted at 80° C. for 1.5 h, evaporated under reduced pressure to remove the solvent, the reside was added with water, extracted with DCM, the organic phase was washed with water, concentrated and purified by column chromatography to obtain 4.55 g of a white solid with a yield of 60%. $^1$H NMR (400 MHz, $CDCl_3$): δ 7.98-7.91 (m, 2H), 7.82-7.77 (m, 2H), 7.43-7.36 (m, 4H), 7.31-7.27 (m, 2H), 7.19 (d, J=7.6 Hz, 1H), 7.14 (d, J=7.6 Hz, 1H), 5.19 (s, 2H). ESI-MS: m/z=382.09 $[M+H]^+$.

(4) Synthesis of Intermediate 29-3

29-3

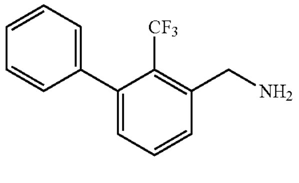

29-2 (450 mg, 1.18 mmol) was dissolved in 7 mL of ethanol, added with 85% hydrazine hydrate (125 mg, 2.12 mmol), reacted at reflux for 3 h, cooled and then added with 1.38 mL of 6N HCl aqueous solution, the reflux was continued for 30 min, the reaction system was cooled, suction filtration was conducted to remove the insolubles, the filtrate was concentrated, adjusted to pH=10 with 1N NaOH, extracted with DCM/MeOH=10/1, the organic phase was washed once with water, and the solvent was evaporated to dryness to obtain 290 mg of a colorless oil with a yield of 98%, which was used directly without purification in the next step. $^1$H NMR (400 MHz, $CDCl_3$): δ 7.57 (d, J=7.6 Hz, 1H), 7.51 (t, J=7.6 Hz, 1H), 7.42-7.33 (m, 3H), 7.29-7.25 (m, 2H), 7.19 (d, J=7.6 Hz, 1H), 4.08 (q, J=1.6 Hz, 2H). ESI-MS: m/z=252.09 $[M+H]^+$.

(5) Synthesis of Intermediate 29-4

29-4

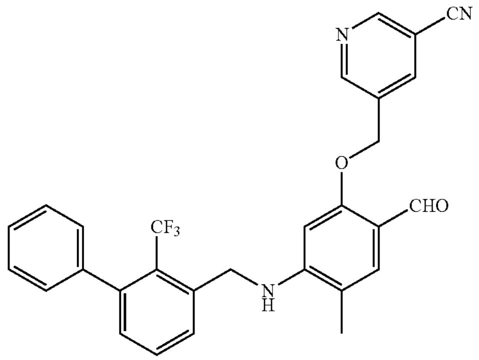

29-3 (290 mg, 1.15 mmol), 5-3 (459 mg, 1.39 mmol), $Cs_2CO_3$ (564 mg, 1.73 mmol), BINAP (144 mg, 0.23 mmol) and $Pd(OAc)_2$ (26 mg, 0.12 mmol) were suspended in 9 mL of dioxane, reacted at reflux under the protection of Ar for 16 h, concentrated, added with water, extracted with EA, the organic phase was washed with water to neutral, and purified by column chromatography to obtain 388 mg of a yellow-white solid with a yield of 67%. $^1H$ NMR (400 MHz, $CDCl_3$): δ 10.21 (s, 1H), 8.82 (d, J=1.6 Hz, 1H), 8.79 (d, J=2.0 Hz, 1H), 7.99 (t, J=2.0 Hz, 1H), 7.63 (s, 1H), 7.51-7.46 (m, 2H), 7.46-7.38 (m, 3H), 7.30-7.27 (m, 3H), 5.96 (s, 1H), 5.10 (s, 2H), 4.88 (br, 1H), 4.73 (s, 2H), 2.21 (s, 3H). ESI-MS: m/z=502.15 $[M+H]^+$.

(6) Synthesis of Compound 29

29

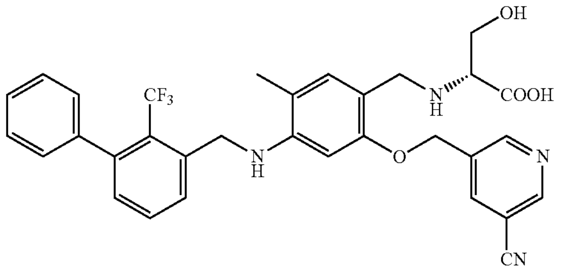

29-4 (358 mg, 0.71 mmol) and D-serine (150 mg, 1.43 mmol) were suspended in 6 mL of anhydrous DMF and 2 mL of anhydrous MeOH, then added with glacial acetic acid (82 μL, 1.43 mmol), reacted at 35° C. for 24 h, followed by an addition of $NaBH(OAc)_3$ (454 mg, 2.14 mmol), the reaction was continued for 24 h, followed by an addition of water, the resulting mixture was extracted with a mixed solvent of DCM/MeOH (10:1), the organic phase was washed with water, concentrated to dryness, the residue was purified by preparative liquid phase chromatography to obtain 181 mg of a white powder solid with a yield of 43%. $^1H$ NMR (400 MHz, DMSO-$d_6$): δ 8.89 (d, J=2.0 Hz, 1H), 8.82 (d, J=2.0 Hz, 1H), 8.34 (t, J=2.0 Hz, 1H), 7.51 (t, J=7.6 Hz, 1H), 7.46-7.38 (m, 4H), 7.31 (d, J=2.0 Hz, 1H), 7.29 (d, J=1.6 Hz, 1H), 7.19 (d, J=7.6 Hz, 1H), 7.05 (s, 1H), 6.09 (t, J=5.6 Hz, 1H), 5.93 (s, 1H), 5.32 (br, 1H), 5.09 (dd, J=17.8, 13.2 Hz, 2H), 4.57 (d, J=4.0 Hz, 2H), 4.03 (dd, J=40.4, 13.2 Hz, 2H), 3.78 (dd, J=11.4, 4.4 Hz, 1H), 3.64 (dd, J=11.6, 7.2 Hz, 1H), 3.19-3.16 (m, 1H), 2.14 (s, 3H). ESI-HRMS: m/z calculated for $C_{32}H_{29}F_3N_4NaO_4^+$ $[M+Na]^+$ 613.2033, found 613.2033.

Example 30

(1) Synthesis of Intermediate 30-1

30-1

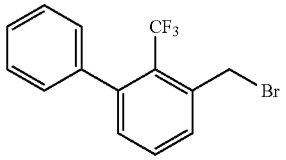

29-1 (473 mg, 2.0 mmol) was dissolved in 8 mL of $CCl_4$, added with NBS (356 mg, 2 mmol) and 75% BPO (32 mg, 0.10 mmol), reacted at reflux for 10 h, concentrated to dryness, added with water, extracted with DCM, the organic phase was washed with water, then washed with saturated brine, dried over anhydrous $Na_2SO_4$, subjected to suction filtration, and the filtrate was purified by column chromatography to obtain 390 mg of a white solid with a yield of 62%. $^1H$ NMR (400 MHz, $CDCl_3$): δ 7.61-7.56 (m, 1H), 7.51 (t, J=7.6 Hz, 1H), 7.40-7.36 (m, 3H), 7.27-7.23 (m, 3H), 4.73 (q, J=1.6 Hz, 2H).

(2) Synthesis of Intermediate 30-2

30-2

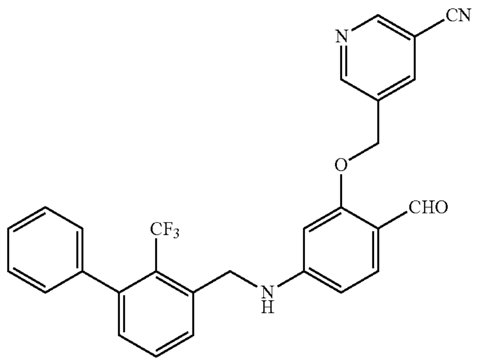

30-1 (630 mg, 2 mmol) and 10-2 (532 mg, 2.10 mmol) were dissolved in a mixed solution of 10.5 mL of MeCN and 3.5 mL of DMF, then added with $K_2CO_3$ (332 mg, 2.40 mmol), reacted at 60° C. for 11 h, concentrated, added with water, extracted with EA, the organic phase was washed with water to neutral, and purified by column chromatography to obtain 120 mg of a yellow-white solid with a yield of 12%. $^1H$ NMR (400 MHz, $CDCl_3$): δ 10.19 (s, 1H), 8.85 (d, J=2.0 Hz, 2H), 8.05 (t, J=2.2 Hz, 1H), 7.74 (d, J=8.4 Hz, 1H), 7.53 (d, J=7.2 Hz, 1H), 7.49 (t, J=7.6 Hz, 1H), 7.44-7.36 (m, 3H), 7.30-7.23 (m, 3H), 6.35 (dd, J=8.4, 1.6 Hz, 1H), 6.06 (d, J=2.0 Hz, 1H), 5.16 (s, 2H), 5.04 (t, J=5.8 Hz, 1H), 4.69 (d, J=4.8 Hz, 2H). ESI-MS: m/z=488.14 $[M+H]^+$.

(3) Synthesis of Compound 30

30

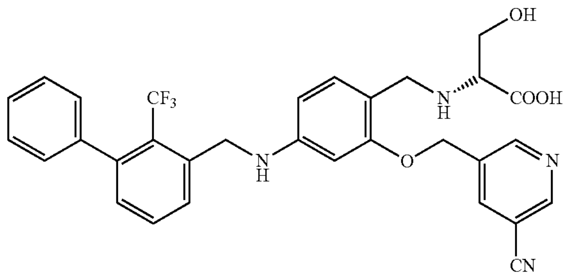

30-2 (120 mg, 0.25 mmol) and D-serine (52 mg, 0.49 mmol) were suspended in 3 mL of anhydrous DMF, then added with glacial acetic acid (28 μL, 0.49 mmol), reacted at 35° C. for 24 h, added with $NaBH(OAc)_3$ (157 mg, 0.74 mmol), the reaction was continued for 24 h, followed by an addition of water, the resulting mixture was extracted with a mixed solvent of DCM/MeOH (10:1), the organic phase was washed with water, concentrated to dryness, and the residue was purified by preparative liquid phase chromatography to obtain 56 mg of a white powdery solid with a yield of 39%. $^1H$ NMR (400 MHz, DMSO-$d_6$): δ 9.00 (d, J=2.0 Hz, 1H), 8.99 (d, J=2.0 Hz, 1H), 8.50 (t, J=2.0 Hz, 1H), 8.21 (br, 2H), 7.60-7.55 (m, 2H), 7.47-7.37 (m, 3H), 7.31-7.26 (m, 2H), 7.22 (t, J=4.0 Hz, 1H), 7.10 (d, J=8.0 Hz, 1H), 6.72 (t, J=5.6 Hz, 1H), 6.35 (d, J=1.6 Hz, 1H), 6.13 (dd, J=8.0, 1.6 Hz, 1H), 5.34 (br, 1H), 5.19 (dd, J=19.6, 13.2 Hz, 2H), 4.49 (d, J=4.0 Hz, 2H), 4.03 (dd, J=44.0, 13.2 Hz, 2H), 3.76 (dd, J=11.6, 4.4 Hz, 1H), 3.63 (dd, J=11.6, 7.2 Hz, 1H), 3.16 (dd, J=7.2, 4.4 Hz, 1H). ESI-HRMS: m/z calculated for $C_{31}H_{27}F_3N_4NaO_4^+$ $[M+Na]^+$ 599.1877, found 599.1876.

Example 31

(1) Synthesis of Intermediate 31-1

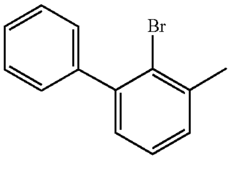

2-Bromo-1-iodo-3-toluene (5 g, 16.8 mmol), phenylboronic acid (2.36 g, 19.35 mmol), cesium acetate (8.08 g, 42.09 mmol) and $PdCl_2$(dppf) (1.24 g, 1.69 mmol) were suspended in 40 mL of THF, reacted at refluxe under argon protection for 36 h, cooled, concentrated, the residue was added with water, extracted with DCM, the organic phase was washed with water, concentrated and purified by column chromatography to obtain 3.93 g of a colorless oil with a yield of 95%. $^1H$ NMR (400 MHz, $CDCl_3$): δ 7.61-7.58 (m, 1H), 7.48-7.31 (m, 6H), 7.26-7.23 (m, 1H), 7.16-7.10 (m, 1H), 2.49 (s, 3H).

(2) Synthesis of Intermediate 31-2

31-2

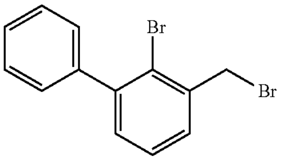

31-1 (3.93 g, 15.90 mmol) was dissolved in 70 mL of $CCl_4$, added with NBS (2.83 g, 15.90 mmol) and 75% BPO (255 mg, 0.79 mmol), reacted at reflux for 11 h, concentrated to dryness, added with water, and extracted with DCM, the organic phase was washed with water, concentrated and purified by column chromatography to obtain 3.36 g of a white solid with a yield of 65%. $^1H$ NMR (400 MHz, $CDCl_3$): δ 7.47-7.42 (m, 2H), 7.41-7.39 (m, 2H), 7.38-7.35 (m, 2H), 7.33 (t, J=7.6 Hz, 1H), 7.25 (dd, J=7.6, 2.0 Hz, 1H), 4.71 (s, 2H).

(3) Synthesis of Intermediate 31-3

31-3

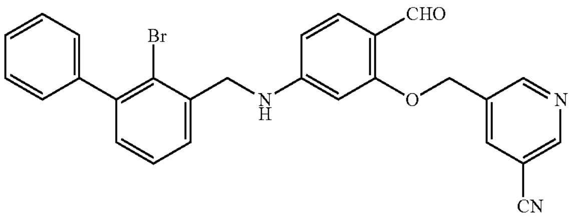

31-2 (860 mg, 2.64 mmol) and 10-2 (668 mg, 2.64 mmol) were dissolved in a mixed solution of 15 mL of MeCN and 5 mL of DMF, then added with $K_2CO_3$ (437 mg, 3.16 mmol), reacted at reflux for 11 h, concentrated, added with water, extracted with EA, the organic phase was washed with water to neutral, and purified by column chromatography to obtain 200 mg of a yellow-white solid with a yield of 15%. $^1H$ NMR (400 MHz, DMSO-$d_6$): δ 10.06 (s, 1H), 9.00 (d, J=1.6 Hz, 1H), 8.97 (d, J=1.6 Hz, 1H), 8.47 (s, 1H), 7.55-7.50 (m, 2H), 7.50-7.44 (m, 2H), 7.43-7.37 (m, 4H), 7.33 (dd, J=7.4, 1.4 Hz, 1H), 7.28 (dd, J=7.2, 1.6 Hz, 1H), 6.34 (d, J=10.4 Hz, 2H), 5.29 (s, 2H), 4.50 (d, J=5.6 Hz, 2H). ESI-MS: m/z=498.08 $[M+H]^+$.

(4) Synthesis of Compound 31

31

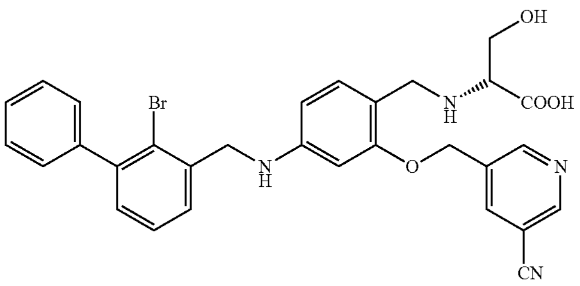

31-3 (316 mg, 0.63 mmol) and D-serine (133 mg, 1.27 mmol) were suspended in 6 mL of anhydrous DMF, then added with glacial acetic acid (72 μL, 1.27 mmol), reacted at 35° C. for 24 h, followed by an addition of $NaBH(OAc)_3$ (403 mg, 1.90 mmol), the reaction was continued for 24 h, followed by an addition of water, the resulting mixture was extracted with a mixed solvent of DCM/MeOH (10:1), the organic phase was washed with water, concentrated to dryness, the residue was purified by preparative liquid phase chromatography to obtain 153 mg of a white powdery solid with a yield of 41%. $^1H$ NMR (400 MHz, DMSO-$d_6$): δ 9.00 (d, J=2.0 Hz, 1H), 8.98 (d, J=2.0 Hz, 1H), 8.50 (t, J=2.0 Hz, 1H), 8.22 (br, 1H), 7.50-7.44 (m, 2H), 7.44-7.40 (m, 1H), 7.40-7.34 (m, 3H), 7.32 (dd, J=7.8, 1.8 Hz, 1H), 7.24 (dd, J=7.2, 2.0 Hz, 1H), 7.09 (d, J=8.4 Hz, 1H), 6.66 (t, J=5.8 Hz, 1H), 6.37 (d, J=1.6 Hz, 1H), 6.14 (dd, J=8.2, 1.8 Hz, 1H), 5.31 (br, 1H), 5.20 (dd, J=19.6, 13.2 Hz, 2H), 4.37 (d, J=6.0 Hz, 2H), 4.04 (dd, J=44.4, 13.2 Hz, 2H), 3.77 (dd, J=11.2, 4.4 Hz, 1H), 3.63 (dd, J=11.6, 7.2 Hz, 1H), 3.16 (dd, J=7.2, 4.4 Hz, 1H). ESI-HRMS: m/z calculated for $C_{30}H_{27}BrN_4NaO_4^+$ $[M+Na]^{+609.1108}$, found 609.1111.

Example 32

(1) Synthesis of Intermediate 32-1

32-1

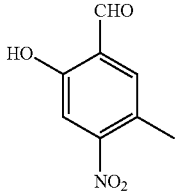

3-Methyl-4-nitrobenzaldehyde (1.90 g, 11.52 mmol), 2-amino-4-chlorobenzoic acid (0.99 g, 5.76 mmol), 1-fluoro-2,4,6-trimethylpyridine trifluoromethanesulfonate (5 g, 17.29 mmol), $Pd(OAc)_2$ (259 mg, 1.15 mmol) and p-toluenesulfonic acid (3.97 g, 23.05 mmol) were suspended in 115 mL of glacial acetic acid, stirred at room temperature for 10 min, and continued to react at 90° C. for 24 h, the reaction system was cooled, concentrated, and the residue was purified by column chromatography to obtain 942 mg of a pale yellow solid with a yield of 45%. $^1H$ NMR (400 MHz, DMSO-$d_6$): δ 11.31 (s, 1H), 10.33 (s, 1H), 7.69 (s, 1H), 7.52 (s, 1H), 2.40 (s, 3H). ESI-MS: m/z=180.03 $[M-H]^-$.

(2) Synthesis of Intermediate 32-2

32-2

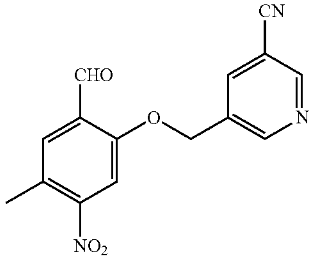

32-1 (578 mg, 3.19 mmol) was dissolved in 17 mL of MeCN and 3.5 mL of DMF, added with $K_2CO_3$ (485 mg, 3.51 mmol), 5-chloromethylnicotinonitrile (535 mg, 3.51 mmol) and NaI (96 mg, 0.64 mmol), reacted at room temperature for 24 h, then added with 80 mL of water, the mixture was subjected to suction filtration, the filter cake was washed with water to neutral, and dried to obtain 939 mg of a yellow-white powdery solid with a yield of 99%, which was used directly in the next step without purification. $^1H$ NMR (400 MHz, DMSO-$d_6$): δ 10.44 (s, 1H), 9.04 (t, J=2.0 Hz, 1H), 8.56 (t, J=2.0 Hz, 1H), 7.91 (s, 1H), 7.82 (s, 1H), 5.47 (s, 2H), 2.45 (s, 3H). ESI-MS: m/z=296.07 $[M-H]^-$.

(3) Synthesis of Intermediate 32-3

32-3

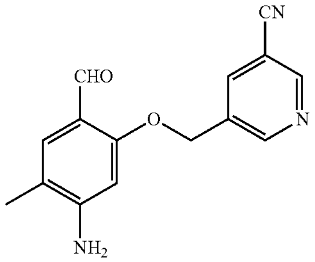

32-2 (1.46 g, 4.91 mmol) was suspended in 55 mL of a mixed solution of $EtOH/H_2O$=5/1, added with Fe (963 mg, 17.20 mmol) and $NH_4C_1$ (394 mg, 7.37 mmol), reacted at reflux for 4 h, suction filtration was conducted to remove insolubles, the filtrate was evaporated to dryness, added with water, extracted with DCM/MeOH=20/1, and the organic phase was concentrated to dryness to obtain 1.30 g of an orange-yellow powdery solid with a yield of 99%, which was used directly in the next step without purification. $^1H$ NMR (400 MHz, DMSO-$d_6$): δ 10.03 (s, 1H), 9.02 (d, J=2.0 Hz, 1H), 8.99 (d, J=2.0 Hz, 1H), 8.48 (t, J=2.0 Hz, 1H), 7.33 (s, 1H), 6.32 (s, 1H), 6.19 (s, 2H), 5.22 (s, 2H), 2.01 (s, 3H). ESI-MS: m/z=268.11 $[M+H]^+$.

(4) Synthesis of Intermediate 32-4

32-4

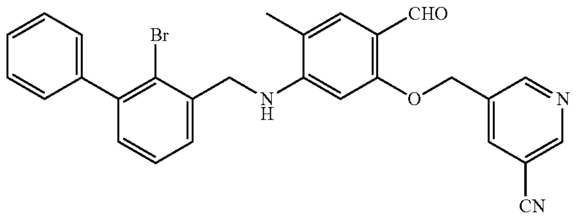

31-2 (815 mg, 2.50 mmol) and 32-3 (702 mg, 2.63 mmol) were dissolved in a mixed solution of 12 mL of MeCN and 4 mL of DMF, then added with $K_2CO_3$ (415 mg, 3.0 mmol), reacted at reflux for 7.5 h, concentrated, added with water, extracted with EA, the organic phase was washed with water to neutral, and purified by column chromatography to obtain 180 mg of a yellow-white solid with a yield of 14%. $^1$H NMR (400 MHz, $CDCl_3$): δ 10.20 (s, 1H), 8.82 (d, J=2.0 Hz, 1H), 8.80 (d, J=2.0 Hz, 1H), 7.99 (t, J=2.2 Hz, 1H), 7.62 (d, J=0.4 Hz, 1H), 7.49-7.42 (m, 3H), 7.42-7.37 (m, 2H), 7.36-7.29 (m, 2H), 7.28-7.24 (m, 1H), 5.98 (s, 1H), 5.13 (s, 2H), 4.90 (t, J=5.8 Hz, 1H), 4.61 (d, J=6.0 Hz, 2H), 2.19 (s, 3H). ESI-MS: m/z=512.08 $[M+H]^+$.

(5) Synthesis of Compound 32

32

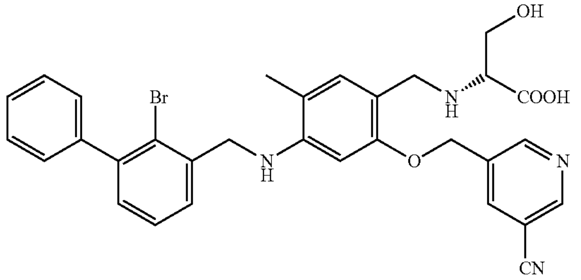

32-4 (180 mg, 0.35 mmol) and D-serine (74 mg, 0.70 mmol) were suspended in 3.5 mL of anhydrous DMF, then added with glacial acetic acid (40 μL, 0.70 mmol), reacted at 35° C. for 24 h, added with $NaBH(OAc)_3$ (224 mg, 1.06 mmol), continued to react for 24 h, followed by an addition of water, the resulting mixture was extracted with a mixed solvent of DCM/MeOH (10:1), the organic phase was washed with water, concentrated to dryness, and the residue was purified by preparative liquid phase chromatography to obtain 46 mg of a white powdery solid with a yield of 22%. $^1$H NMR (400 MHz, DMSO-$d_6$): δ 8.89 (d, J=1.6 Hz, 1H), 8.83 (d, J=1.6 Hz, 1H), 8.34 (s, 1H), 8.14 (br, 2H), 7.48-7.39 (m, 5H), 7.30 (t, J=7.6 Hz, 1H), 7.20 (t, J=7.6 Hz, 2H), 7.03 (s, 1H), 6.03-5.96 (m, 2H), 5.29 (br, 1H), 5.12 (dd, J=18.6, 13.4 Hz, 2H), 4.44 (d, J=5.6 Hz, 2H), 4.03 (dd, J=40.0, 13.0 Hz, 2H), 3.77 (dd, J=11.4, 4.2 Hz, 1H), 3.64 (dd, J=11.0, 7.4 Hz, 1H), 3.17 (dd, J=6.8, 4.4 Hz, 1H), 2.13 (s, 3H). ESI-HRMS: m/z calculated for $C_{31}H_{29}BrN_4NaO_4^+$ $[M+Na]^+$ 623.1264, found 623.1265.

Example 33

(1) Synthesis of Intermediate 33-1

33-1

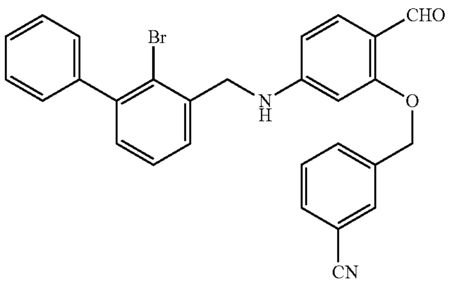

31-2 (400 mg, 1.23 mmol) and 1-4 (325 mg, 1.29 mmol) were dissolved in a mixed solution of 4.5 mL of MeCN and 2.5 mL of DMF, then added with $K_2CO_3$ (203 mg, 1.47 mmol), reacted at reflux for 10 h, concentrated, added with water, extracted with EA, the organic phase was washed with water to neutral, and purified by column chromatography to obtain 155 mg of a yellow-white solid with a yield of 25%. $^1$H NMR (400 MHz, $CDCl_3$): δ 10.24 (s, 1H), 7.74 (d, J=8.4 Hz, 1H), 7.69-7.60 (m, 3H), 7.50 (t, J=7.6, 1H), 7.48-7.40 (m, 3H), 7.41-7.34 (m, 2H), 7.32-7.26 (m, 3H), 6.35-6.30 (m, 1H), 6.06 (d, J=2.0 Hz, 1H), 5.12 (s, 2H), 4.99 (br, 1H), 4.55 (s, 2H). ESI-MS: m/z=497.07 $[M+H]^+$.

(2) Synthesis of Compound 33

33

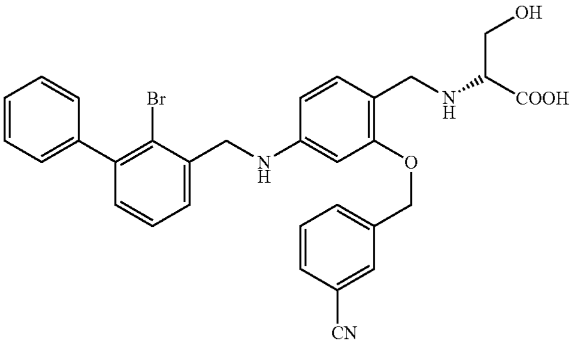

33-1 (152 mg, 0.31 mmol) and D-serine (64 mg, 0.61 mmol) were suspended in 3 mL of anhydrous DMF, then added with glacial acetic acid (35 μL, 0.61 mmol), reacted at 35° C. for 24 h, followed by an addition of $NaBH(OAc)_3$ (194 mg, 0.92 mmol), continued to react for 24 h, followed by an addition of water, the resulting mixture was extracted with a mixed solvent of DCM/MeOH (10:1), the organic phase was washed with water, concentrated to dryness, and the residue was purified by preparative liquid phase chromatography to obtain 128 mg of a yellow-white powdery solid with a yield of 70%. $^1$H NMR (400 MHz, DMSO-$d_6$): δ 8.26 (br, 2H), 7.98 (s, 1H), 7.87 (d, J=8.0 Hz, 1H), 7.79 (d, J=7.6 Hz, 1H), 7.57 (t, J=8.0 Hz, 1H), 7.51-7.29 (m, 6H), 7.24 (dd, J=7.2, 1.6 Hz, 1H), 7.08 (d, J=8.4 Hz, 1H), 6.64 (t, J=6.0 Hz, 1H), 6.34 (d, J=1.6 Hz, 1H), 6.12 (dd, J=8.0, 1.6

Hz, 1H), 5.33 (br, 1H), 5.18-5.10 (m, 2H), 4.35 (d, J=5.6 Hz, 2H), 4.03 (dd, J=40.4, 12.8 Hz, 2H), 3.78 (dd, J=11.6, 4.0 Hz, 1H), 3.65 (dd, J=11.2, 7.2 Hz, 1H), 3.18-3.15 (m, 1H). ESI-HRMS: m/z calculated for $C_{28}H_{22}BrN_2O$ $[M-C_3H_6NO_3]^+$ 481.0910, found 481.0911.

Example 34

(1) Synthesis of Intermediate 34-1

34-1

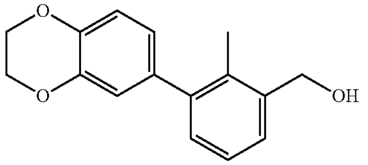

3-Bromo-2-methylbenzyl alcohol (3.25 g, 16.16 mmol), benzo-1,4-dioxane-6-boronic acid (3.64 g, 20.23 mmol), cesium acetate (7.75 g, 40.38 mmol)) and $PdCl_2$(dppf) (1.19 g, 1.62 mmol) were suspended in 50 mL of THF, reacted at reflux under argon protection for 24 h, cooled, concentrated, the residue was added with water, extracted with DCM, the organic phase was washed with water, concentrated and purified by column chromatography to obtain 4.05 g of a colorless oil with a yield of 98%. $^1$H NMR (400 MHz, $CDCl_3$): δ 7.36 (dd, J=7.6, 1.2 Hz, 1H), 7.22 (t, J=7.6 Hz, 1H), 7.17 (dd, J=7.6, 1.6 Hz, 1H), 6.89 (d, J=8.4 Hz, 1H), 6.81 (d, J=2.0 Hz, 1H), 6.76 (dd, J=8.0, 2.0 Hz, 1H), 4.76 (s, 2H), 4.30 (s, 4H), 2.25 (s, 3H), 1.66 (s, 1H). ESI-MS: m/z=257.12 $[M+H]^+$.

(2) Synthesis of Intermediate 34-2

34-2

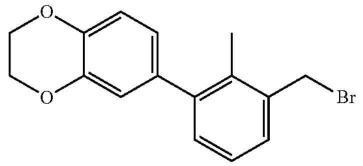

34-1 (513 mg, 2.0 mmol) was dissolved in 10 mL of DCM, cooled to 0° C. in an ice bath, added dropwise with $PBr_3$ (0.094 mL, 1.0 mmol), after the addition, the reaction was continued for 20 min, quenched by adding crushed ice, extraction was carried out with DCM for three times, the organic phase was washed with saturated sodium bicarbonate solution once, then washed with water to neutral, dried over anhydrous $Na_2SO_4$, subjected to suction filtration, and concentrated to dryness to obtain 550 mg of a colorless oil with a yield of 86%, which was directly used in the next step without purification. $^1$H NMR (400 MHz, $CDCl_3$): δ 7.35-7.29 (m, 1H), 7.22-7.15 (m, 2H), 6.93-6.89 (m, 1H), 6.82-6.80 (m, 1H), 6.78-6.74 (m, 1H), 4.59 (s, 2H), 4.31 (s, 4H), 2.32 (s, 3H). ESI-MS: m/z=239.11 [M-Br]$^+$.

(3) Synthesis of Intermediate 34-3

34-3

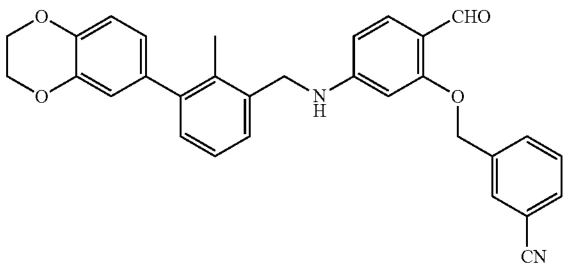

34-2 (550 mg, 1.72 mmol) and 1-4 (435 mg, 1.72 mmol) were dissolved in a mixed solution of 10 mL of MeCN and 3 mL of DMF, then added with $K_2CO_3$ (262 mg, 1.90 mmol), reacted at reflux for 11 h, concentrated, added with water, extracted with EA, the organic phase was washed with water to neutral, and purified by column chromatography to obtain 170 mg of a yellow-white solid with a yield of 20%. $^1$H NMR (400 MHz, $CDCl_3$): S 10.23 (s, 1H), 7.74 (d, J=8.4 Hz, 1H), 7.71-7.66 (m, 2H), 7.63 (d, J=7.8 Hz, 1H), 7.51 (t, J=7.8 Hz, 1H), 7.25-7.22 (m, 1H), 7.22-7.17 (m, 2H), 6.91 (d, J=8.4 Hz, 1H), 6.81 (d, J=2.0 Hz, 1H), 6.76 (dd, J=8.2, 2.2 Hz, 1H), 6.31 (dd, J=8.6, 1.8 Hz, 1H), 6.07 (d, J=1.6 Hz, 1H), 5.14 (s, 2H), 4.64 (s, 1H), 4.38 (s, 2H), 4.31 (s, 4H), 2.24 (s, 3H). ESI-MS: m/z=491.20 $[M+H]^+$.

(4) Synthesis of Compound 34

34

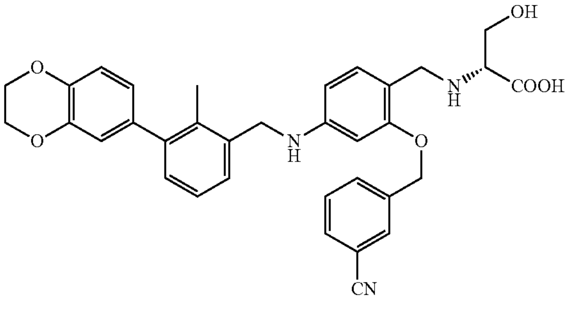

34-3 (162 mg, 0.33 mmol) and D-serine (69 mg, 0.66 mmol) were suspended in 3 mL of anhydrous DMF, then added with glacial acetic acid (38 μL, 0.66 mmol), reacted at 35° C. for 24 h, followed by an addition of $NaBH(OAc)_3$ (210 mg, 0.99 mmol), continued to react for 24 h, then added with water, extracted with a mixed solvent of DCM/MeOH (10:1), the organic phase was washed with water, concentrated to dryness, the residue was purified by preparative liquid phase chromatography to obtain 91 mg of a yellow-white powdery solid with a yield of 48%. $^1$H NMR (400 MHz, DMSO-$d_6$): δ 8.33 (br, 2H), 7.99 (s, 1H), 7.88 (d, J=8.0 Hz, 1H), 7.79 (d, J=7.6 Hz, 1H), 7.57 (t, J=8.0 Hz, 1H), 7.22 (d, J=8.0 Hz, 1H), 7.15 (t, J=7.6 Hz, 1H), 7.07 (d, J=8.0 Hz, 2H), 6.92 (d, J=8.0 Hz, 1H), 6.80-6.67 (m, 2H), 6.36-6.34 (m, 2H), 6.19 (d, J=8.0 Hz, 1H), 5.36 (br, 1H), 5.18-5.10 (m, 2H), 4.28 (br, 4H), 4.23 (d, J=4.4 Hz, 2H), 4.03 (dd, J=43.6, 13.2 Hz, 2H), 3.77 (dd, J=10.8, 4.0 Hz, 1H), 3.65 (dd, J=11.2, 8.0 Hz, 1H), 3.17-3.14 (m, 1H), 2.18 (s, 3H). ESI-HRMS: m/z calculated for $C_{34}H_{33}N_3NaO_6^+$ $[M+Na]^+$ 602.2262, found 602.2266.

Example 35

(1) Synthesis of Intermediate 35-1

35-1

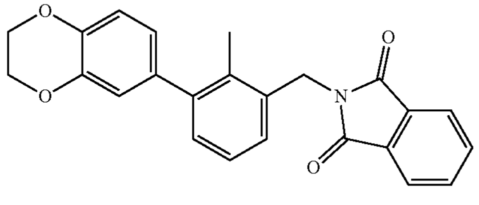

To a three-necked flask was added 34-1 (3.46 g, 13.50 mmol), phthalimide (2.38 g, 16.18 mmol) and $PPh_3$ (4.96 g, 18.91 mmol), followed by an addition of 60 mL of anhydrous THF under the protection of Ar, cooled to 0° C., added dropwise with DEAD (3.29 g, 18.89 mmol), after the addition, the reaction was carried out at room temperature for 24 h. The solvent was evaporated to dryness, and the residue was purified by column chromatography to obtain 5.02 g of a white solid with a yield of 97%. $^1H$ NMR (400 MHz, $CDCl_3$): δ 7.89-7.87 (m, 2H), 7.75-7.73 (m, 2H), 7.21-7.16 (m, 1H), 7.14 (d, J=4.0 Hz, 1H), 7.13 (s, 1H), 6.88 (d, J=8.0 Hz, 1H), 6.80 (d, J=2.0 Hz, 1H), 6.74 (dd, J=8.4, 2.0 Hz, 1H), 4.93 (s, 2H), 4.30 (s, 4H), 2.35 (s, 3H). ESI-MS: m/z=386.14 $[M+H]^+$.

(2) Synthesis of Intermediate 35-2

35-2

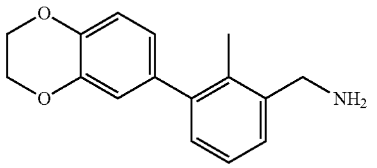

35-1 (4.88 g, 12.66 mmol) was dissolved in 75 mL of ethanol, added with 85% hydrazine hydrate (1.34 g, 22.75 mmol), reacted at reflux for 6 h, cooled and added with 10 mL of 6N HCl aqueous solution, continued to reflux for 30 min, cooled, suction filtration was conducted to remove insolubles, the filtrate was concentrated, adjusted to pH=10 with 1N NaOH, extracted with DCM/MeOH=10/1, the organic phase was washed with water, the solvent was evaporated to dryness to obtain 3.20 g of a colorless oil with a yield of 99%, which was used directly without purification in the next step. $^1H$ NMR (400 MHz, $CDCl_3$): δ 7.31 (dd, J=7.6, 1.2 Hz, 1H), 7.21 (t, J=7.6 Hz, 1H), 7.12 (dd, J=7.6, 1.2 Hz, 1H), 6.89 (d, J=8.4 Hz, 1H), 6.80 (d, J=2.0 Hz, 1H), 6.75 (dd, J=8.4, 2.0 Hz, 1H), 4.30 (s, 4H), 3.91 (s, 2H), 2.23 (s, 3H), 1.56 (s, 2H). ESI-MS: m/z=256.13 $[M+H]^+$.

(3) Synthesis of Intermediate 35-3

35-3

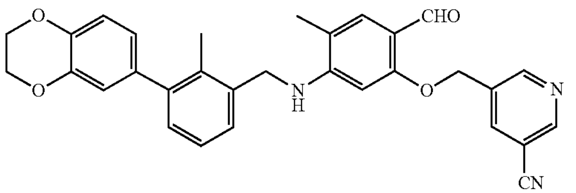

35-2 (420 mg, 1.64 mmol), 5-3 (654 mg, 1.97 mmol), $Cs_2CO_3$ (804 mg, 2.47 mmol), BINAP (205 mg, 0.33 mmol) and $Pd(OAc)_2$ (37 mg, 0.16 mmol) were suspended in 11 mL of dioxane, reacted at 85° C. under the protection of Ar for 24 h, concentrated, added with water, extracted with EA, the organic phase was washed with water to neutral, and purified by column chromatography to obtain 325 mg of a yellow-white solid with a yield of 39%. $^1H$ NMR (400 MHz, DMSO-$d_6$): δ 10.06 (s, 1H), 8.92 (d, J=2.0 Hz, 1H), 8.83 (d, J=2.4 Hz, 1H), 8.33 (t, J=2.0 Hz, 1H), 7.38 (d, J=0.8 Hz, 1H), 7.13-7.08 (m, 2H), 7.07-7.05 (m, 1H), 6.92 (d, J=8.0 Hz, 1H), 6.81 (d, J=2.0 Hz, 1H), 6.77 (dd, J=8.2, 2.2 Hz, 1H), 6.67 (t, J=5.8 Hz, 1H), 6.09 (s, 1H), 5.21 (s, 2H), 4.47 (d, J=5.6 Hz, 2H), 4.29 (s, 4H), 2.23 (s, 3H), 2.14 (s, 3H). ESI-MS: m/z=506.20 $[M+H]^+$.

(4) Synthesis of Compound 35

35

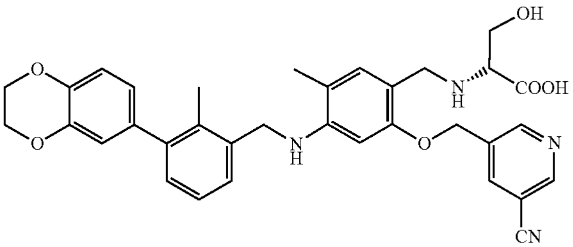

35-3 (288 mg, 0.57 mmol) and D-serine (120 mg, 1.14 mmol) were suspended in 6 mL of anhydrous DMF and 2 mL of anhydrous methanol, then added with glacial acetic acid (65 μL, 1.14 mmol), reacted at 35° C. for 24 h, followed by an addition of $NaBH(OAc)_3$ (362 mg, 1.71 mmol), continued to react for 24 h, added with water, extracted with a mixed solvent of DCM/MeOH (10:1), the organic phase was washed with water, concentrated to dryness, and the residue was purified by preparative liquid phase chromatography to obtain 98 mg of a white powder solid with a yield of 29%. $^1H$ NMR (400 MHz, DMSO-$d_6$): δ 8.89 (d, J=2.0 Hz, 1H), 8.85 (d, J=2.0 Hz, 1H), 8.36 (t, J=2.0 Hz, 1H), 8.22 (br, 2H), 7.11 (dd, J=7.2, 1.6 Hz, 1H), 7.08 (t, J=7.2 Hz, 1H), 7.03 (dd, J=7.2, 1.6 Hz, 1H), 7.00 (s, 1H), 6.91 (d, J=8.0 Hz, 1H), 6.81 (d, J=2.0 Hz, 1H), 6.77 (dd, J=8.4, 2.0 Hz, 1H), 6.07 (s, 1H), 5.69 (t, J=5.6 Hz, 1H), 5.31 (br, 1H), 5.13 (dd, J=18.8, 13.2 Hz, 2H), 4.32 (d, J=5.2 Hz, 2H), 4.28 (s, 4H), 4.03 (dd, J=44.0, 13.2 Hz, 2H), 3.77 (dd, J=11.2, 4.4 Hz, 1H), 3.64 (dd, J=11.6, 7.2 Hz, 1H), 3.16 (dd, J=7.2, 4.4 Hz, 1H), 2.20 (s, 3H), 2.10 (s, 3H). ESI-HRMS: m/z calculated for $C_{34}H_{34}N_4NaO_6^+$ $[M+Na]^+$617.2371, found 617.2377.

Example 36

(1) Synthesis of Intermediate 36-1

36-1

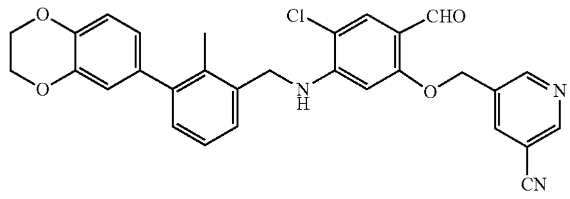

35-2 (418 mg, 1.64 mmol), 13-2 (480 mg, 1.37 mmol), $Cs_2CO_3$ (667 mg, 2.05 mmol), BINAP (170 mg, 0.27 mmol) and $Pd(OAc)_2$ (31 mg, 0.14 mmol) were suspended in 14 mL of dioxane, reacted at reflux under the protection of Ar for 24 h, concentrated, added with water, extracted with EA, the organic phase was washed with water to neutral, and purified by column chromatography to obtain 559 mg of a yellow-white solid with a yield of 78%. $^1$H NMR (400 MHz, DMSO-$d_6$): δ 10.04 (s, 1H), 8.93 (d, J=2.0 Hz, 1H), 8.85 (d, J=2.0 Hz, 1H), 8.36 (t, J=2.0 Hz, 1H), 7.60 (s, 1H), 7.14-7.03 (m, 4H), 6.92 (d, J=8.2 Hz, 1H), 6.80 (d, J=2.0 Hz, 1H), 6.76 (dd, J=8.2, 2.2 Hz, 1H), 6.26 (s, 1H), 5.25 (s, 2H), 4.56 (d, J=6.0 Hz, 2H), 4.29 (s, 4H), 2.22 (s, 3H).

ESI-MS: m/z=526.19 $[M+H]^+$.

(2) Synthesis of Compound 36

36

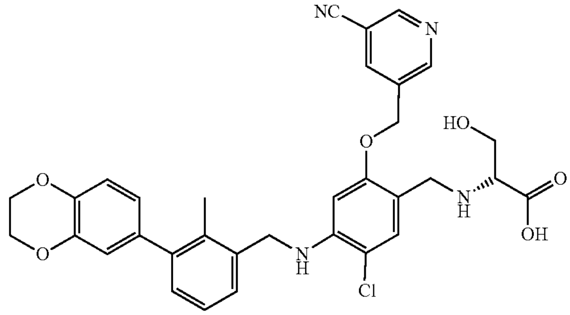

36-1 (340 mg, 0.65 mmol) and D-serine (135 mg, 1.28 mmol) were suspended in 6 mL of anhydrous DMF and 2 mL of anhydrous methanol, then added with glacial acetic acid (74 μL, 1.28 mmol), reacted at 35° C. for 24 h, followed by an addition of $NaBH(OAc)_3$ (410 mg, 1.93 mmol), continued to react for 24 h, added with water, extracted with a mixed solvent of DCM/MeOH (10:1), the organic phase was washed with water, concentrated to dryness, and the residue was purified by preparative liquid phase chromatography to obtain 135 mg of a white powder solid with a yield of 34%. $^1$H NMR (400 MHz, DMSO-$d_6$): δ 8.89 (d, J=2.0 Hz, 1H), 8.85 (d, J=2.0 Hz, 1H), 8.36 (t, J=2.0 Hz, 1H), 8.17 (br, 2H), 7.37 (s, 1H), 7.12-7.01 (m, 3H), 6.92 (d, J=8.0 Hz, 1H), 6.80 (d, J=2.0 Hz, 1H), 6.76 (dd, J=8.2, 2.2 Hz, 1H), 6.22 (s, 1H), 6.07 (t, J=5.8 Hz, 1H), 5.38 (br, 1H), 5.15 (dd, J=18.0, 13.2 Hz, 2H), 4.40 (d, J=5.6 Hz, 2H), 4.28 (s, 4H), 4.01 (dd, J=33.6, 13.2 Hz, 2H), 3.75 (dd, J=11.2, 4.4 Hz, 1H), 3.64 (dd, J=11.6, 6.8 Hz, 1H), 3.18 (dd, J=6.8, 4.4 Hz, 1H), 2.20 (s, 3H). ESI-HRMS: m/z calculated for $C_{33}H_{31}ClN_4NaO_6^+$ $[M+Na]^{+637.1824}$, found 637.1825.

Example 37: (Comparative Example 1)

(1) Synthesis of Intermediate 37-1

37-1

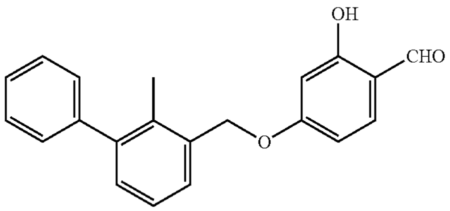

To a three-necked flask was added 1-1 (2.18 g, 11 mmol), 2,4-dihydroxybenzaldehyde (1.38 g, 10 mmol) and $PPh_3$ (2.89 g, 11 mmol), followed by an addition of 100 mL of anhydrous THF under the protection of Ar, cooled to 0° C., added dropwise with DIAD (2.22 g, 11 mmol), after the addition, the reaction was carried out at room temperature for 24 h. The solvent was evaporated to dryness, the residue was purified by column chromatography to obtain 1.75 g of a yellow solid with a yield of 55%. $^1$H NMR (400 MHz, $CDCl_3$): δ 11.52 (s, 1H), 9.75 (s, 1H), 7.51-7.29 (m, 11H), 6.68 (dd, J=8.5, 2.2 Hz, 1H), 6.61 (d, J=2.1 Hz, 1H), 5.16 (s, 2H), 2.27 (s, 3H). ESI-MS: m/z=319.13 $[M+H]^+$.

(2) Synthesis of Intermediate 37-2

37-2

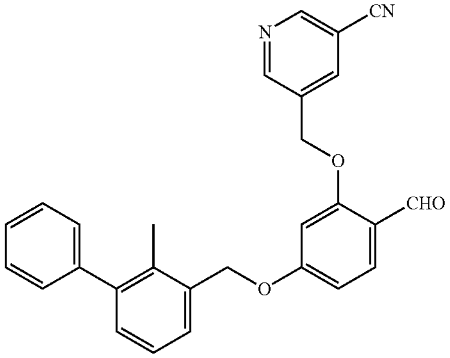

37-1 (318 mg, 1 mmol) was dissolved in 12 mL of acetonitrile, added in sequence with $K_2CO_3$ (207 mg, 1.5 mmol), tetra-n-butylammonium iodide (18 mg, 0.05 mmol) and 5-chloromethylnicotinonitrile (183 mg, 1.2 mmol), reacted at 75° C. overnight, the reaction solution was concentrated, added with water, extracted with EA, the organic phase was washed with water to neutral, and purified by column chromatography to obtain 226 mg of a yellow solid with a yield of 52%. $^1$H NMR (400 MHz, DMSO-$d_6$): δ 10.26 (s, 1H), 9.05-8.97 (m, 2H), 8.56 (s, 1H), 7.72 (d, J=2.0 Hz, 1H), 7.55-7.49 (m, 3H), 7.45-7.38 (m, 1H), 7.35-7.28 (m, 3H), 7.25 (d, J=2.1 Hz, 1H), 7.01 (s, 1H), 6.89 (d, J=2.1 Hz, 1H), 5.45 (s, 2H), 5.31 (s, 2H), 2.25 (s, 3H). ESI-MS: m/z=435.16 $[M+H]^+$.

(3) Synthesis of Compound 37

37

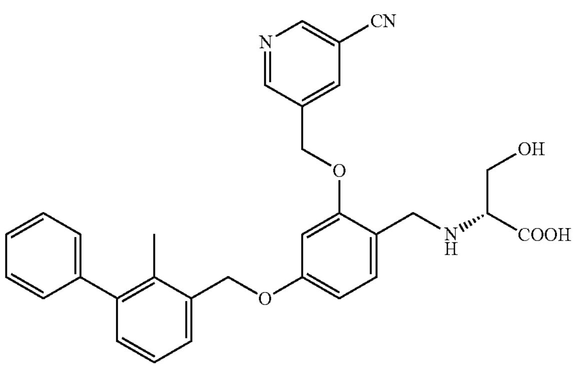

37-2 (217 mg, 0.50 mmol) and D-serine (105 mg, 1 mmol) were dissolved in 5 mL of anhydrous DMF, added with glacial acetic acid (58 μL, 1 mmol), reacted at 35° C. for 24 h, followed by an addition of $NaBH(OAc)_3$ (318 mg, 1.5 mmol), continued to react for 24 h, added with water, extracted with a mixed solvent of DCM/MeOH (10:1), the organic phase was washed with water, concentrated to dryness, and the residue was purified by preparative liquid phase chromatography to obtain 138 mg of a white solid with a yield of 53%. $^1H$ NMR (400 MHz, DMSO-$d_6$): δ 9.05 (s, 1H), 9.01 (s, 1H), 8.35 (br, 2H), 7.49-7.40 (m, 3H), 7.40-7.28 (m, 5H), 7.20 (d, J=2.1 Hz, 1H), 6.88 (s, 1H), 6.75 (d, J=2.1 Hz, 1H), 5.36-5.25 (m, 2H), 5.17 (s, 2H), 4.07 (d, J=5.2 Hz, 1H), 4.00 (d, J=7.2 Hz, 1H), 3.73 (d, J=6.8 Hz, 1H), 3.64 (dd, J=11.4, 7.2 Hz, 1H), 3.17-3.14 (m, 1H), 2.21 (s, 3H), 1.93 (s, 1H). ESI-MS: m/z=524.25 $[M+H]^+$.

Example 38: (Comparative Example 2)

(1) Synthesis of Intermediate 38-1

38-1

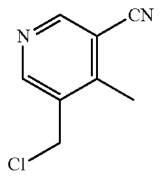

To a reactor was added (5-Bromo-4-methylpyridin-3-yl) methanol (308 mg, 2.5 mmol) and CuCN (560 mg, 6.25 mmol) and suspended in 8 mL of pyridine, reacted at 160° C. for 24 h, cooled, the reaction solution was added to 4 mL of concentrated ammonia water and 12 mL of saturated ammonium chloride, and stirred at room temperature for 2 h. The mixture was extracted with a mixed solution of dichloromethane/isopropanol (85:15), the extract liquor was dried over anhydrous sodium sulfate and then concentrated to dryness to obtain 305 mg of 5-hydroxymethyl-4-methylpyridine-3-carbonitrile, which was used directly in the next step.

5-Hydroxymethyl-4-methylpyridine-3-carbonitrile (305 mg, 2.06 mmol) was dissolved in 9 mL of DCM, added with thionyl chloride (0.3 mL, 4.12 mmol), stirred at room temperature until the reaction was completed. The reaction solution was concentrated to dryness, and EA was added. The organic phase was washed with saturated sodium bicarbonate and sodium chloride solution, concentrated to dryness and purified by column chromatography to obtain 223 mg of an oily product with a yield of 65%. $^1H$ NMR (400 MHz, $CDCl_3$): δ 9.08 (s, 1H), 8.75 (s, 1H), 4.52 (s, 2H), 2.45 (s, 3H). ESI-MS: m/z=131.08 $[M-Cl]^+$.

(2) Synthesis of Intermediate 38-2

38-2

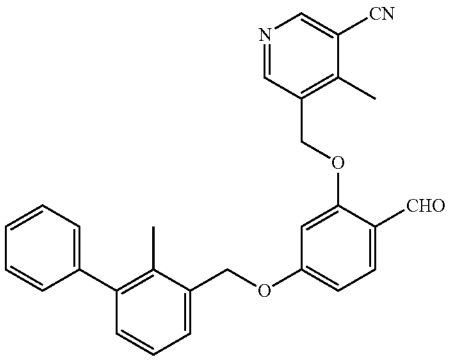

37-1 (337 mg, 1.06 mmol) was dissolved in 12 mL of acetonitrile, added in sequence with $K_2CO_3$ (220 mg, 1.59 mmol), tetra-n-butylammonium iodide (18 mg, 0.053 mmol) and intermediate 38-1 (211 mg, 1.27 mmol)), reacted at 75° C. overnight, the reaction solution was concentrated, added with water, extracted with EA, the organic phase was washed with water to neutral, and purified by column chromatography to obtain 357 mg of a pale yellow solid with a yield of 75%. $^1H$ NMR (400 MHz, DMSO-$d_6$): δ 10.26 (s, 1H), 8.97 (s, 1H), 8.92 (s, 1H), 7.87 (d, J=2.3 Hz, 1H), 7.54-7.47 (m, 3H), 7.45-7.34 (m, 1H), 7.35-7.28 (m, 4H), 6.89 (d, J=2.1 Hz, 1H), 6.69 (d, J=2.1 Hz, 1H), 5.45 (s, 2H), 5.31 (s, 2H), 2.55 (s, 3H), 2.25 (s, 3H). ESI-MS: m/z=449.21 $[M+H]^+$.

(3) Synthesis of Compound 38

38

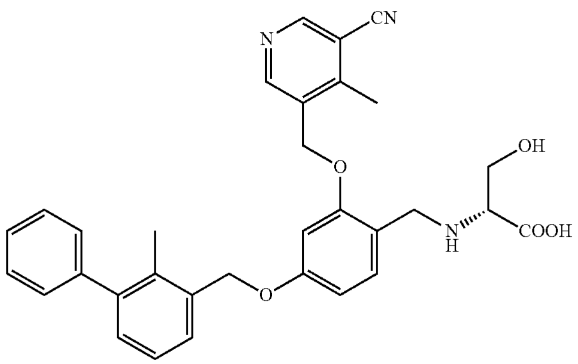

38-2 (224 mg, 0.50 mmol) and D-serine (105 mg, 1 mmol) were dissolved in 5 mL of anhydrous DMF, added with glacial acetic acid (58 μL, 1 mmol), reacted at 35° C.

for 24 h, then added with $NaBH(OAc)_3$ (318 mg, 1.5 mmol), continued to react for 24 h, added with water, extracted with a mixed solvent of DCM/MeOH (10:1), the organic phase was washed with water, concentrated to dryness, and the residue was purified by preparative liquid phase chromatography to obtain 132 mg of a white solid with a yield of 49%. $^1H$ NMR (400 MHz, DMSO-$d_6$): δ 9.05 (s, 1H), 9.01 (s, 1H), 8.35 (br, 2H), 7.47-7.39 (m, 3H), 7.41-7.23 (m, 5H), 7.26 (d, J=2.1 Hz, 1H), 6.89 (s, 1H), 6.75 (d, J=2.1 Hz, 1H), 5.36-5.25 (m, 2H), 5.16 (s, 2H), 4.07 (d, J=5.2 Hz, 1H), 4.03 (d, J=7.2 Hz, 1H), 3.71 (d, J=6.8 Hz, 1H), 3.64 (dd, J=11.4, 7.2 Hz, 1H), 3.17-3.14 (m, 1H), 2.56 (s, 3H), 2.21 (s, 3H), 1.95 (s, 1H). ESI-MS: m/z=538.25 $[M+H]^+$.

Example 39: Activity of Compounds to Inhibit PD-1/PD-L1 Interaction

The inhibitory activity of compounds on PD-1/PD-L1 interaction was evaluated at the protein level using PD-1/PD-L1 Binding Assay kits from Cisbio Company. The evaluation method of the kit was based on the principle of homogeneous time-resolved fluorescence (HTRF), the kit contained relevant proteins, reagents and buffers required for the experiment. The positive control compound BMS202 was purchased from MCE Company.

(1) Experimental Method

The experimental method and procedure were carried out in accordance with the kit instructions, which were briefly described as follows:

The compounds were formulated into DMSO solutions of desired concentrations. Tag1-PD-L1, Tag2-PD-1 and compound solutions were diluted with diluent buffer to form working solutions, and anti-Tag1-$Eu^{3+}$ and anti-Tag2-XL665 were diluted with detection buffer to form working solutions. White 384 shallow-well plates were used for the experiment, and 2 μL of compound working solution, 4 μL of Tag1-PD-L1 working solution and 4 μL of Tag2-PD-1 working solution were added in order to each well, and incubated at room temperature for 15 min; 10 μL of a mixed solution formed by well mixing 5 μL of anti-Tag1-$Eu^{3+}$ working solution and 5 μL of anti-Tag2-XL665 working solution was added to each well, and incubated for 2.5 h and detected; control groups were also set up in the experiment, wherein 2 μL of diluent buffer was used to replace 2 μL of compound working solution to form the Positive control, and 6 μL of diluent buffer was used to replace 2 μL of compound working solution and 4 μL of Tag1-PD-L1 working solution to form the Negative control. Fluorescence intensities at emission wavelengths of 620 nm and 665 nm were detected under excitation light of 320 nm using Infinite F200 PRO from TECAN Company. HTRF value of each well=(fluorescence intensity at 665 nm/fluorescence intensity at 620 nm)×104, compound inhibition rate (%)=[1-(HTRF value of compound well—HTRF value of Negative control well)/(HTRF value of Positive control well—HTRF value of Negative control well)]×100%, and the inhibition rates of each compound at 8-10 concentrations were detected, and the $IC_{50}$ was calculated using Prism software.

(2) Experimental Results

The results of the evaluation of the inhibitory activity of the compounds on the PD-1/PD-L1 interaction were shown in the table below.

| Compound | $IC_{50}$ (μM) |
|---|---|
| 1 | 4.942 |
| 2 | 3.673 |
| 3 | 2.599 |
| 4 | 1.155 |
| 5 | 0.012 |
| 6 | 0.436 |
| 7 | 0.363 |
| 8 | 0.672 |
| 9 | 4.243 |
| 10 | 0.038 |
| 11 | 0.107 |
| 12 | 4.536 |
| 13 | 0.026 |
| 14 | 0.253 |
| 15 | 2.632 |
| 16 | 2.583 |
| 17 | 0.092 |
| 18 | 0.023 |
| 19 | 0.165 |
| 20 | 0.347 |
| 21 | 0.024 |
| 22 | 0.017 |
| 23 | 0.036 |
| 24 | 1.334 |
| 25 | 0.047 |
| 26 | >100 |
| 27 | 22.55 |
| 28 | 0.191 |
| 29 | 0.610 |
| 30 | 2.933 |
| 31 | 0.206 |
| 32 | 0.031 |
| 33 | 0.637 |
| 34 | 0.435 |
| 35 | 0.044 |
| 36 | 0.131 |
| 37 | 0.323 |
| 38 | 1.042 |
| BMS202 | 0.175 |
| / | / |

Example 40: Interaction Between Compound and Human PD-L1 Protein (1) Experimental Method In the experiment, the instrument OctectRED of Fortebio Company based on biofilm interferometry (BLI) technology was used to capture human PD-L1/AVI with SA chips. The concentration of antigen PD-L1/AVI was diluted to 10 g/mL with running buffer (PBS+0.02% Tween-20+2% DMSO), and the loading time was 300 s; similarly, the analyte was also diluted to the corresponding concentrations (20 nM, 10 nM, 5 nM, 2.5 nM, 1.25 nM, 0.625 nM, 0.3125 nM) with running buffer in gradient manner, and a buffer blank control group was set at the same time. The binding time of human PD-L1/AVI to the analyte was 180 s, and the dissociation time was 300 s; the chip was regenerated with 10 mM glycine HCl, pH 1.7 solution and repeated 5-second pulse for 3 times. The data were fitted to a 1:1 binding model to determine the equilibrium dissociation constant KD.

(1) Experimental Results

The results were shown in the following table, the compounds had strong binding ability to human PD-L1, and their affinity KD values were at the level of nM or above.

| Compound | Kon(1/Ms) | Kdis(1/s) | KD(M) |
|---|---|---|---|
| 4 | 6.51E+05 | 1.18E−03 | 1.81E−09 |
| 5 | 2.17E+06 | 3.53E−05 | 1.62E−11 |
| 10 | 8.49E+05 | 2.51E−04 | 2.96E−10 |
| 11 | 1.29E+06 | 6.64E−04 | 5.15E−10 |
| 37 | 1.26E+04 | 8.51E−04 | 6.75E−08 |

Example 41: Evaluation of Compound in Promoting IFN-γ Secretion In Vitro (1) Experimental Method Human peripheral blood mononuclear cells (PBMCs) were isolated from 10-15 ml of whole blood of healthy volunteers using experimental human lymphocyte separation medium (TBD sciences). The cells were washed twice with normal saline and resuspended in buffer (RPMI 1640 complete medium containing 10% FBS, SIGMA) to count the cell density. The PBMCs were dispersed and placed in a 96-well plate, $1\times10^5$ cells and 50 μL of buffer per well. Anti-CD3 antibody (SIGMA) and anti-CD28 antibody (SIGMA) were mixed at a ratio of 1:1 to obtain an antibody mixture. The antibody mixture was added to the wells to ensure that the final concentration of antibody was 0.8 μg/mL. At the same time, PDL1/FC fusion protein (SINO BIOLOGICAL) was added to reach a final concentration of 10.0 μg/mL, and the compound to be tested was diluted with buffer and added to the wells to reach a final concentration of 0.1 μM or 1 μM. The mixed system was incubated at 37° C. and 5% $CO_2$ for 72 h. The supernatant was collected, and the expression level of IFN-γ was measured by ELISA MAXTM Human IFN-γ Standard Kit (BioLegend), and the increase rate was calculated. Increase rate (%)=(expression amount of compound treatment—expression amount of PDL1 treatment)/expression amount of PDL1 treatment× 100%

(2) Experimental Results

The results were shown in the following table, Compound 5 and Compound 10 had a significant effect on promoting IFN-γ secretion at the cellular level, which was better than that of BMS202.

| Compound | Concentration (μM) | IFN-γ (pg/mL) | Increase rate (%) |
|---|---|---|---|
| hPD-L1 | 10.0 μg/mL | 2.13E+04 | 0 |
| 5 | 0.1 | 3.83E+04 | 79.8 |
| | 1.0 | 4.24E+04 | 99.1 |
| 10 | 0.1 | 3.77E+04 | 77.0 |
| | 1.0 | 4.15E+04 | 94.8 |
| 37 | 0.1 | 2.32E+04 | 8.9 |
| | 1.0 | 2.51E+04 | 17.8 |
| 38 | 0.1 | 2.33E+04 | 9.4 |
| | 1.0 | 2.26E+04 | 6.1 |
| BMS202 | 0.1 | 3.51E+04 | 64.8 |
| | 1.0 | 3.91E+04 | 83.6 |

Example 42: Evaluation of Cytotoxicity of the Compounds (1) Experimental Method The raji (ATCC), raw (ATCC) and PBMCs cells were suspended in buffer (RPMI 1640 complete medium containing 10% FBS, SIGMA), respectively, and the cell density was counted. The cells were transferred to wells of a 96-well plate, ensuring that the cell density of each well was $1\times10^4$ cells/well, and incubated for 24 hours at 37° C., 5% $CO_2$ with compounds at different concentrations (100 μM, 50 μM, 25 μM, 12.5 μM, 6.25 M and 3.125 PM) and buffer control solution (0.2% DMSO). To each well, 100 μL of Cell Titer-Glo Luminescent Solution (Promega) was added and shaken for 10 minutes at room temperature, and then GloMax® Navigator System was used to measure the system fluorescence, and the cell death rate was calculated. Cell death rate (%)=(1−RLUcompound/RLUcontrol)×100%, and IC50 was determined from the inhibition curve.

(2) Experimental Results

The experimental results were shown in the table below. The results showed that most of the compounds had good safety to a variety of cells, and only a few compounds showed certain toxicity.

| Compound | Raji cells IC50 (μM) | Raw cells IC50 (μM) | PBMCs cells IC50 (μM) |
|---|---|---|---|
| 4 | >100.0 | >100.0 | >100.0 |
| 5 | >100.0 | >100.0 | >100.0 |
| 8 | >100.0 | >100.0 | >100.0 |
| 10 | >100.0 | >100.0 | >100.0 |
| 14 | >100.0 | >100.0 | >100.0 |
| 17 | 78.9 | 61.6 | >100.0 |
| 21 | >100.0 | 88.2 | 75.5 |
| 27 | 84.1 | >100.0 | >100.0 |
| 31 | >100.0 | >100.0 | >100.0 |
| 34 | 90.3 | >100.0 | >100.0 |
| 37 | 22.6 | 31.2 | 16.8 |
| 38 | 32.1 | 28.8 | 26.6 |

Example 43: Evaluation of Antitumor Efficacy In Vivo

Based on the mechanism that PD-1/PD-L1 inhibitors activated the immune system to achieve anti-tumor effects by interfering with the interaction of PD-1/PD-L1, the animal models used in vivo efficacy experiments must be animals with healthy immune systems; in addition, the species differences of PD-1/PD-L1 between animals and humans are considered. Therefore, the in vivo antitumor pharmacodynamics evaluation model of the present invention adopted PD-1 humanized mice, and the inoculated tumors were PD-L1 humanized tumor cells. This evaluation model could more accurately reflect the in vivo efficacy of the compound.

(1) Experimental Method

24 PD-A humanized mice (full name of strain: C57BL/6J-Pdcd1$^{em1(hPDCD1)/Smoc}$) about 6 weeks old were purchased from Shanghai Southern Model Animal Center, and placed in SPF grade animal breeding room for observation for 1 to 2 weeks. After the animals were adapted to the raising environment, the genetically engineered colon cancer cell line MC38 (mouse PD-L1 knockout, human PD-L1 knockin) was subcutaneously inoculated to the mice near the hind leg groin, and the inoculated cell volume was $1\times10^6$ cells per mouse. After 7-10 days of observation, when the tumor volume grew to 50-150 $mm^3$, animals were randomly divided into vehicle group and test group according to the tumor size according to the random number table, 6 animals in each group. The test group was administered with 15 mg/kg of Compound 5 by intraperitoneal injection, the vehicle group was also intraperitoneally injected with the same volume of buffer as the test group, and the frequency of administration was once per day for three weeks. During the experiment, the tumor size and mouse body weight were measured and recorded, and the mice were sacrificed at the end of the experiment. The mouse body weight and tumor proliferation curve were drawn.

(2) Experimental Results

Figure 2:
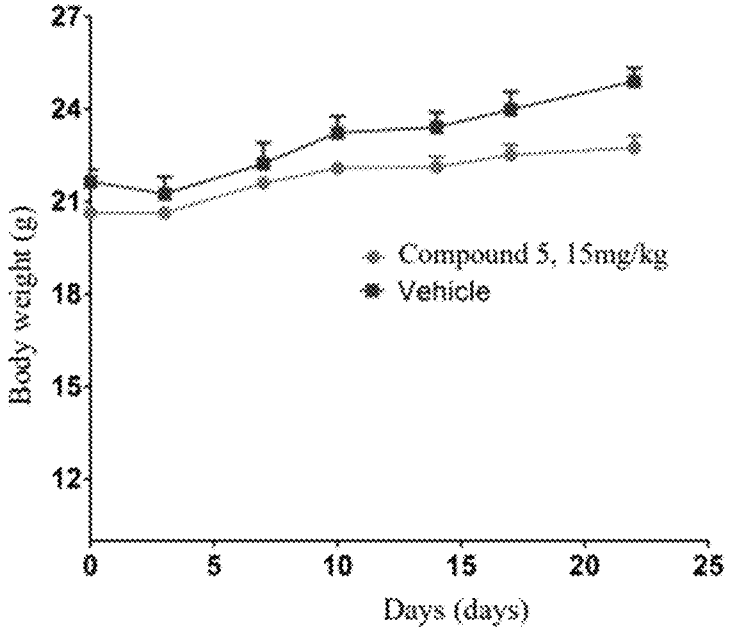
FIG. 2 shows the accumulation curve of body weight over time after 15 mg/kg of Compound 5 was administered by intraperitoneal injection to PD-1 humanized mice.

The experimental results were shown in FIGS. 1 and 2. Compared with the control group, Compound 5 could significantly inhibit the growth of tumors.

Various modifications of the present invention, in addition to those described herein, will be apparent to those skilled in the art from the foregoing description. Such modifications are also intended to fall within the scope of the appended claims. Each reference cited in the present application, including all patents, patent applications, journal articles, books, and any other publications, is incorporated by reference in its entirety.

What is claimed is:

1. A benzylamine derivative of general Formula (I), or a pharmaceutically acceptable stereoisomer, salt solvate or prodrug thereof, Formula (I)

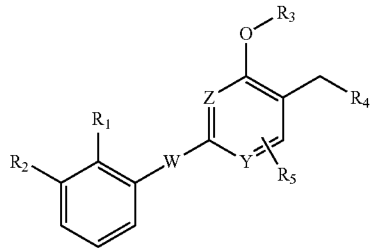

W =

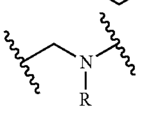

or

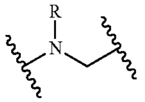

wherein,

R is selected from the group consisting of hydrogen and C1-C8 alkyl;

$R_1$ is selected from the group consisting of hydrogen, deuterium, halogen, C1-C4 alkyl, deuterated C1-C4 alkyl, halogenated C1-C4 alkyl and C1-C4 alkoxy;

$R_2$ is selected from the group consisting of

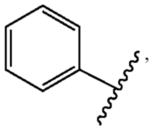

,

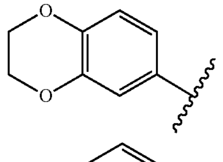

and

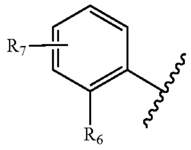

, wherein $R_6$ is selected from the group consisting of halogen, C1-C4 alkyl, deuterated C1-C4 alkyl, halogenated C1-C4 alkyl and C1-C4 alkoxy, $R_7$ is at the meta or ortho position of $R_6$ and $R_7$ is selected from the group consisting of hydrogen, —O—$(CH_2)_n$—$R_0$, —CONH—$R_0$ and —$(CH_2)_n$—$R_0$, wherein n is an integer of 1-4, $R_0$ is cyano, hydroxyl, carboxyl, amino or a heteroatom-containing linear or cyclic hydrophilic substituent;

$R_3$ is selected from $R_8$—$CH_2$—, wherein $R_5$ is selected from the group consisting of hydrogen, cyano, C1-C4 alkyl, halogenated C1-C4 alkyl, C2-C4 alkenyl, —$NR_9R_{10}$, —$CONR_9R_{10}$, 3- to 6-membered cycloalkyl, 3- to 6-membered heterocycloalkyl, 6- to 10-membered aryl and 5- to 10-membered heteroaryl, optionally, the C1-C4 alkyl, halogenated C1-C4 alkyl, C2-C4 alkenyl, —$NR_9R_{10}$, —$CONR_9R_{10}$, 3- to 6-membered cycloalkyl, 3- to 6-membered heterocycloalkyl, 6- to 10-membered aryl, and 5- to 10-membered heteroaryl that are each independently substituted with one or more substituents selected from the group consisting of cyano, halogen, carboxyl, C1-C4 alkyl, C1-C4 alkoxy, C1-C4 alkylsulfonyl, 3- to 6-membered cycloalkyl, hydroxyl-substituted 3 to 6-membered cycloalkyl, 3- to 6-membered heterocycloalkyl, hydroxyl-substituted 3- to 6-membered heterocycloalkyl, —$CONR_9R_{10}$ and —$NR_9COR_{10}$, wherein $R_9$ and $R_{10}$ at each occurrence are each independently selected from the group consisting of hydrogen, deuterium and C1-C4 alkyl;

$R_4$ is selected from the group consisting of hydroxyl, carboxyl, fragment of amino acid and —$NR_{10}R_{11}$, wherein $R_{10}$ and $R_{11}$ are each independently selected from the group consisting of hydrogen, deuterium, C1-C6 alkyl and 3- to 6-membered cycloalkyl, optionally, the C1-C6 alkyl and 3- to 6-membered cycloalkyl are each independently substituted with one or more substituents selected from the group consisting of mercapto group, hydroxyl, carboxyl, hydroxyl-substituted C1-C6 alkyl, C1-C6 amido and 3- to 6-membered nitrogen-containing heterocycloalkyl; or, $R_{10}$ and $R_{11}$ together with the N atom connected therewith form a 5- to 6-membered heterocycloalkyl, optionally, the 5- to 6-membered heterocycloalkyl is substituted with one or more groups selected from the group consisting of amino, hydroxyl, carboxyl, mercapto group and hydroxyl-substituted C1-C6 alkyl;

$R_5$ is selected from the group consisting of hydrogen, deuterium, cyano, halogen, C1-C4 alkyl, C2-C4 alkenyl, deuterated C1-C4 alkyl, halogenated C1-C4 alkyl and C1-C4 alkoxy;

Y and Z are each independently selected from the group consisting of carbon and nitrogen.

2. The benzylamine derivative according to claim 1, or a pharmaceutically acceptable stereoisomer, salt, solvate or prodrug thereof, wherein the structure of the benzylamine derivative is as shown by Formula (I-A):

Formula (I-A)

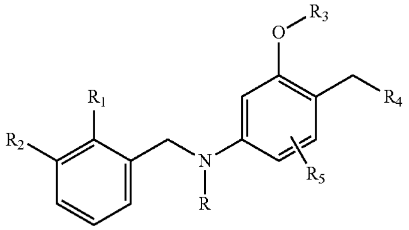

wherein R, $R_1$, $R_2$, $R_3$, $R_4$ and $R_5$ are as defined in claim 1, and $R_5$ is at the para or meta position of —$OR_3$.

3. The benzylamine derivative according to claim 1, or a pharmaceutically acceptable stereoisomer, salt, solvate or prodrug thereof, wherein the structure of the benzylamine derivative is as shown by Formula (I-B):

Formula (I-B)

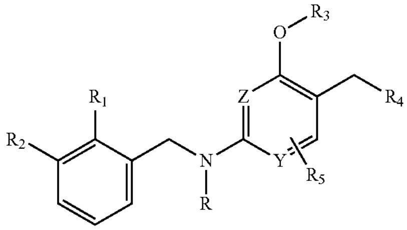

wherein R, $R_1$, $R_2$, $R_3$, $R_4$ and $R_5$ are as defined in claim 1, at least one of Z and Y is nitrogen, and $R_5$ is at the para or meta position of —$OR_3$.

4. The benzylamine derivative according to claim 1, or a pharmaceutically acceptable stereoisomer, salt, solvate or prodrug thereof, wherein the structure of the benzylamine derivative is as shown by Formula (I-C):

Formula (I-C)

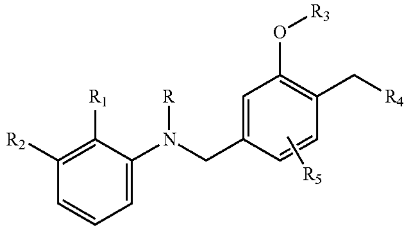

wherein R, $R_1$, $R_2$, $R_3$, $R_4$ and $R_5$ are as defined in claim 1, and $R_5$ is at the para or meta position of —$OR_3$.

5. The benzylamine derivative according to claim 1, or a pharmaceutically acceptable stereoisomer, salt, solvate or prodrug thereof, wherein R is selected from the group consisting of hydrogen and methyl.

6. The benzylamine derivative according to claim 1, or a pharmaceutically acceptable stereoisomer, salt, solvate or prodrug thereof, wherein $R_1$ is selected from the group consisting of halogen, C1-C2 alkyl and halogenated C1-C2 alkyl, such as bromine, methyl or trifluoromethyl.

7. The benzylamine derivative according to claim 1, or a pharmaceutically acceptable stereoisomer, salt, solvate or prodrug thereof, wherein $R_2$ is selected from the group consisting of

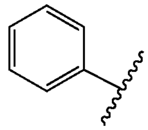

and

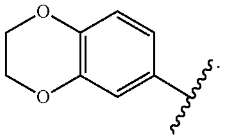

8. The benzylamine derivative according to claim 1, or a pharmaceutically acceptable stereoisomer, salt, solvate or prodrug thereof, wherein $R_3$ is selected from the group consisting of $R_8$—$CH_2$—, wherein $R_5$ is selected from the group consisting of hydrogen, C1-C2 alkyl, phenyl and 5- to 6-membered heteroaryl, optionally, the C1-C2 alkyl, phenyl and 5- to 6-membered heteroaryl are each independently substituted with one cyano.

9. The benzylamine derivative according to claim 1, or a pharmaceutically acceptable stereoisomer, salt, solvate or prodrug thereof, wherein $R_4$ is selected from the group consisting of the fragment of amino acid and —$NR_{10}R_{11}$, wherein $R_{10}$ and $R_{11}$ are each independently selected from the group consisting of hydrogen, deuterium and C1-C6 alkyl, optionally, the C1-C6 alkyl is substituted with one or more substituents selected from the group consisting of mercapto group, hydroxyl, carboxyl, hydroxyl-substituted C1-C4 alkyl, C1-C4 amido, and 5- to 6-membered nitrogen-containing heterocycloalkyl; or, $R_{10}$ and $R_{11}$ together with the N atom connected therewith form a 5- to 6-membered heterocycloalkyl, optionally, the 5- to 6-membered heterocycloalkyl is substituted with one or more groups selected from the group consisting of amino, hydroxyl, carboxyl, mercapto group and hydroxyl-substituted C1-C4 alkyl; the fragment of amino acid is selected from the fragment obtained by losing one hydrogen of the amino that shares a carbon atom with the carboxyl.

10. The benzylamine derivative according to claim 1, or a pharmaceutically acceptable stereoisomer, salt, solvate or prodrug thereof, wherein $R_5$ is selected from the group consisting of hydrogen, deuterium, halogen, C1-C2 alkyl and C1-C2 alkoxy, such as hydrogen, chlorine, methoxy or methyl.

11. The benzylamine derivative according to claim 1, or a pharmaceutically acceptable stereoisomer, salt, solvate or prodrug thereof, wherein the benzylamine derivative is selected from the group consisting of:

N-(2-((2-((3-cyanobenzyl)oxy)-4-(((2-methyl-[1,1'-biphenyl]-3-yl)methyl)amino)benzyl)amino)ethyl)acetamide, 3-((2-(((2-hydroxyethyl)amino)methyl)-5-(((2-methyl-[1,1'-biphenyl]-3-yl)methyl)amino) phenoxy)methyl)benzonitrile, 3-((2-(((1,3-dihydroxyprop-2-yl)amino)methyl)-5-(((2-methyl-[1,1'-biphenyl]-3-yl)methyl)amino)phenoxy)methyl)benzonitrile, (2-((3-cyanobenzyl)oxy)-4-(((2-methyl-[1,1'-biphenyl]-3-yl)methyl)amino)benzyl)-D-serine, (2-((5-cyanopyridin-3-yl)methoxy)-5-methyl-4-(((2-methyl-[1,1'-biphenyl]-3-yl)methyl)amino)benzyl)-D-serine, (2-((3-cyanobenzyl)oxy)-6-methyl-4-(((2-methyl-[1,1'-biphenyl]-3-yl)methyl)amino)benzyl)-D-serine, (2-((5-cyanopyridin-3-yl)methoxy)-6-methyl-4-(((2-methyl-[1,1'-biphenyl]-3-yl)methyl)amino)benzyl)-D-serine, (2-((3-cyanobenzyl)oxy)-6-methoxy-4-(((2-methyl-[1,1'-biphenyl]-3-yl)methyl)amino)benzyl)-D-serine, N-(2-(((2-methoxy-6-(((2-methyl-[1,1'-biphenyl]-3-yl)methyl)amino)pyridin-3-yl)methyl)amino)ethyl)acetamide, (2-((5-cyanopyridin-3-yl)methoxy)-4-(((2-methyl-[1,1'-biphenyl]-3-yl)methyl)amino)benzyl)-D-serine, (5-chloro-2-methoxy-4-(((2-methyl-[1,1'-biphenyl]-3-yl)methyl)amino)benzyl)-D-serine, ((2-methoxy-6-(((2-methyl-[1,1'-biphenyl]-3-yl)methyl)amino)pyridin-3-yl)methyl)-D-serine, (5-chloro-2-((5-cyanopyridin-3-yl)methoxy)-4-(((2-methyl-[1,1'-biphenyl]-3-yl)methyl)amino)benzyl)-D-serine,
(2-methoxy-5-methyl-4-(((2-methyl-[1,1'-biphenyl]-3-yl)methyl)amino)benzyl)-D-serine,
((4-methoxy-6-(((2-methyl-[1,1'-biphenyl]-3-yl)methyl)amino)pyridin-3-yl)methyl)-D-serine,
(2-(benzyloxy)-5-methyl-4-(((2-methyl-[1,1'-biphenyl]-3-yl)methyl)amino)benzyl)-D-serine,
(5-methyl-4-(((2-methyl-[1,1'-biphenyl]-3-yl)methyl)amino)-2-(pyridin-3-ylmethoxy)benzyl)-D-serine,
(R)-3-((2-((5-cyanopyridin-3-yl)methoxy)-5-methyl-4-(((2-methyl-[1,1'-biphenyl]-3-yl)methyl)amino)benzyl)amino)-4-hydroxybutyric acid,
(2-((3-cyanobenzyl)oxy)-5-methyl-4-(((2-methyl-[1,1'-biphenyl]-3-yl)methyl)amino)benzyl)-D-serine,
(2-ethoxy-5-methyl-4-(((2-methyl-[1,1'-biphenyl]-3-yl)methyl)amino)benzyl)-D-serine,
(2S,4R)-1-(2-((5-cyanopyridin-3-yl)methoxy)-5-methyl-4-(((2-methyl-[1,1'-biphenyl]-3-yl)methyl)amino)benzyl)-4-hydroxypyrrolidine-2-carboxylic acid,
(S)-4-((2-((5-cyanopyridin-3-yl)methoxy)-5-methyl-4-(((2-methyl-[1,1'-biphenyl]-3-yl)methyl)amino)benzyl)amino)-3-hydroxybutyric acid,
(S)-5-((2-((4-hydroxy-2-oxopyrrolidin-1-yl)methyl)-4-methyl-5-(((2-methyl-[1,1'-biphenyl]-3-yl)methyl)amino)phenoxy)methyl)nicotinonitrile,
(2-((5-cyanopyridin-3-yl)methoxy)-5-methyl-4-(((2-methyl-[1,1'-biphenyl]-3-yl)methyl)amino)benzyl)-D-homoserine,
(2-((5-cyanopyridin-3-yl)methoxy)-5-methyl-4-(((2-methyl-[1,1'-biphenyl]-3-yl)methyl)amino)benzyl)-D-asparagine,
(2-((3-cyanobenzyl)oxy)-4-(methyl((2-methyl-[1,1'-biphenyl]-3-yl)methyl)amino)benzyl)-D-serine,
3-((2-(((2-hydroxyethyl)amino)methyl)-5-(N-methyl-N-((2-methyl-[1,1'-biphenyl]-3-yl)methyl)amino)phenoxy)methyl)benzonitrile dihydrochloride,
(2-((5-cyanopyridin-3-yl)methoxy)-4-(((2-methyl-[1,1'-biphenyl]-3-yl)amino)methyl)benzyl)-D-serine,
(2-((5-cyanopyridin-3-yl)methoxy)-5-methyl-4-(((2-(trifluoromethyl)-[1,1'-biphenyl]-3-yl)methyl)amino)benzyl)-D-serine,
(2-((5-cyanopyridin-3-yl)methoxy)-4-(((2-(trifluoromethyl)-[1,1'-biphenyl]-3-yl)methyl)amino)benzyl)-D-serine,
(4-(((2-bromo-[1,1'-biphenyl]-3-yl)methyl)amino)-2-((5-cyanopyridin-3-yl)methoxy)benzyl)-D-serine,
(4-(((2-bromo-[1,1'-biphenyl]-3-yl)methyl)amino)-2-((5-cyanopyridin-3-yl)methoxy)-5-methylbenzyl)-D-serine,
(4-(((2-bromo-[1,1'-biphenyl]-3-yl)methyl)amino)-2-((3-cyanobenzyl)oxy)benzyl)-D serine,
(2-((3-cyanobenzyl)oxy)-4-((3-(2,3-dihydrobenzo[b][1,4]dioxin-6-yl)-2-methylbenzyl)amino)benzyl)-D-serine,
(2-((5-cyanopyridin-3-yl)methoxy)-4-(((3-(2,3-dihydrobenzo[b][1,4]dioxin-6-yl))-2-methylbenzyl)amino)-5-methylbenzyl)-D-serine, and
(5-chloro-2-((5-cyanopyridin-3-yl)methoxy)-4-((3-(2,3-dihydrobenzo[b][1,4]dioxin-6-yl)-2-methylbenzyl)amino)-benzyl)-D-serine.

12. A pharmaceutical composition, which comprises the benzylamine derivative according to claim 1, or a pharmaceutically acceptable stereoisomer, salt, solvate or prodrug thereof, and one or more pharmaceutically acceptable carriers or excipients.

* * * * *